US010481158B2

(12) United States Patent
Heath et al.

(10) Patent No.: US 10,481,158 B2
(45) Date of Patent: Nov. 19, 2019

(54) COMPOSITIONS AND METHODS FOR SCREENING T CELLS WITH ANTIGENS FOR SPECIFIC POPULATIONS

(71) Applicant: CALIFORNIA INSTITUTE OF TECHNOLOGY, Pasadena, CA (US)

(72) Inventors: James R. Heath, South Pasadena, CA (US); Songming Peng, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 369 days.

(21) Appl. No.: 15/170,919

(22) Filed: Jun. 1, 2016

(65) Prior Publication Data
US 2017/0003288 A1 Jan. 5, 2017

Related U.S. Application Data

(60) Provisional application No. 62/169,337, filed on Jun. 1, 2015.

(51) Int. Cl.
| G01N 33/53 | (2006.01) |
| C12Q 1/68 | (2018.01) |
| C07H 21/04 | (2006.01) |
| G01N 33/569 | (2006.01) |
| C12Q 1/6804 | (2018.01) |
| G01N 15/14 | (2006.01) |
| G01N 33/574 | (2006.01) |
| G01N 33/68 | (2006.01) |
| G01N 15/00 | (2006.01) |

(52) U.S. Cl.
CPC ....... *G01N 33/56972* (2013.01); *C07H 21/04* (2013.01); *C12Q 1/6804* (2013.01); *G01N 15/14* (2013.01); *G01N 33/574* (2013.01); *G01N 33/6878* (2013.01); *G01N 2015/008* (2013.01); *G01N 2015/149* (2013.01); *G01N 2333/70539* (2013.01); *G01N 2458/10* (2013.01)

(58) Field of Classification Search
None
See application file for complete search history.

(56) References Cited

U.S. PATENT DOCUMENTS

| 4,818,680 A | 4/1989 | Coffins et al. |
| 6,037,167 A | 3/2000 | Adelman et al. |
| 6,100,079 A | 8/2000 | Tajima |
| 6,387,622 B1 | 5/2002 | Siiman et al. |
| 6,649,378 B1 | 11/2003 | Kozwich et al. |
| 6,730,269 B2 | 5/2004 | Mirkin et al. |
| 6,861,221 B2 | 3/2005 | Mirkin et al. |
| 6,969,761 B2 | 11/2005 | Mirkin et al. |
| 6,974,669 B2 | 12/2005 | Mirkin et al. |
| 7,094,555 B2 | 8/2006 | Kwok et al. |
| 7,098,320 B1 | 8/2006 | Mirkin et al. |
| 7,147,687 B2 | 12/2006 | Mirkin et al. |
| 7,169,556 B2 | 1/2007 | Park et al. |
| 7,186,814 B2 | 3/2007 | Garimella et al. |
| 7,208,587 B2 | 4/2007 | Mirkin et al. |
| 7,250,499 B2 | 7/2007 | Mirkin et al. |
| 7,259,252 B2 | 8/2007 | Mirkin et al. |
| 7,323,309 B2 | 1/2008 | Mirkin et al. |
| 7,381,529 B2 | 6/2008 | Yamakawa et al. |
| 7,531,726 B2 | 5/2009 | Chan et al. |
| 7,625,702 B2 | 12/2009 | Cha |
| 7,807,372 B2 | 10/2010 | Mirkin et al. |
| 8,323,888 B2 | 12/2012 | Mirkin et al. |
| 8,354,231 B2 | 1/2013 | Kwong et al. |
| 8,394,590 B2 | 3/2013 | Kwong et al. |
| 8,617,884 B2 | 12/2013 | Berenson et al. |
| 8,709,722 B2 | 4/2014 | Tan et al. |
| 8,993,714 B2 | 3/2015 | Salemme et al. |
| 8,999,263 B2 | 4/2015 | Peterman et al. |
| 9,011,774 B2 | 4/2015 | Kim et al. |
| 9,023,650 B2 | 5/2015 | Farquar et al. |
| 9,173,840 B2 | 11/2015 | Amiji et al. |
| 2002/0168663 A1 | 11/2002 | Phan et al. |
| 2003/0027234 A1 | 2/2003 | Pandian et al. |
| 2003/0219752 A1 | 11/2003 | Short |
| 2003/0223938 A1 | 12/2003 | Nagy et al. |
| 2004/0072231 A1 | 4/2004 | Mirkin et al. |
| 2004/0102369 A1 | 5/2004 | Wu et al. |
| 2004/0137642 A1 | 7/2004 | Erfle et al. |

(Continued)

FOREIGN PATENT DOCUMENTS

| AU | 2007100888 A4 | 11/2007 |
| AU | 2010202492 A1 | 7/2010 |

(Continued)

OTHER PUBLICATIONS

Andersen, Rikke Sick et al.; "Parallel detection of antigen-specific T cell responses by combinatorial encoding of MHC multimers"; Nature Protocols; vol. 7; No. 5; 2012; pp. 891-902.

Bakker, Arnold H. et al.; "Conditional MHC class I ligands and peptide exchange technology for the human MHC gene products HLA-AL, -A3, -ALL, and -B7"; PNAS; Mar. 11, 2008; vol. 105; No. 10; pp. 3825-3830.

(Continued)

*Primary Examiner* — James Martinell

(74) *Attorney, Agent, or Firm* — Goodwin Procter LLP

(57) ABSTRACT

Compositions and methods for isolating patient-derived antigen-specific T cells include an antigen complex having a polynucleotide barcoded nanoparticle sorting agent complexed with a peptide-loaded streptavidin major histocompatability complex (MHC) tetramer, the barcoding technology allowing for high fidelity screening of a library of the antigen complexes to readily isolate and identify antigen-specific T cells.

19 Claims, 28 Drawing Sheets
(27 of 28 Drawing Sheet(s) Filed in Color)
Specification includes a Sequence Listing.

(56) References Cited

U.S. PATENT DOCUMENTS

| | | |
|---|---|---|
| 2005/0019843 A1 | 1/2005 | Chen et al. |
| 2005/0048546 A1 | 3/2005 | Penn et al. |
| 2005/0287611 A1 | 12/2005 | Nugent, IV et al. |
| 2006/0014172 A1 | 1/2006 | Muller et al. |
| 2006/0040286 A1 | 2/2006 | Mirkin et al. |
| 2006/0240416 A1 | 10/2006 | Banerjee et al. |
| 2007/0264652 A1 | 11/2007 | Upadhyay et al. |
| 2008/0188374 A1 | 8/2008 | Chen et al. |
| 2008/0220982 A1 | 9/2008 | Vu |
| 2009/0036324 A1 | 2/2009 | Fan et al. |
| 2010/0004138 A1 | 1/2010 | Sato et al. |
| 2011/0039717 A1 | 2/2011 | Kwong et al. |
| 2011/0166034 A1 | 7/2011 | Kwong et al. |
| 2011/0171749 A1 | 7/2011 | Alocilja et al. |
| 2011/0237449 A1 | 9/2011 | McMaster et al. |
| 2012/0121649 A1 | 5/2012 | Santamaria |
| 2012/0157329 A1 | 6/2012 | Giraldo Castellano et al. |
| 2012/0276103 A1 | 11/2012 | Fraser et al. |
| 2012/0276109 A1 | 11/2012 | Fraser et al. |
| 2013/0130364 A1 | 5/2013 | Seo et al. |
| 2013/0330414 A1 | 12/2013 | Santamaria |
| 2014/0272972 A1 | 9/2014 | Lee |
| 2015/0044672 A1 | 2/2015 | Stojanovic et al. |
| 2015/0050747 A1 | 2/2015 | Alocilja et al. |
| 2015/0051089 A1 | 2/2015 | Robins et al. |
| 2015/0132758 A1 | 5/2015 | Medina-Llamas et al. |
| 2015/0157737 A1 | 6/2015 | Gu et al. |
| 2015/0166997 A1 | 6/2015 | Messmer |
| 2015/0290611 A1 | 10/2015 | Pine et al. |
| 2015/0322494 A1 | 11/2015 | Navarro Y Garcia et al. |
| 2016/0271237 A1 | 9/2016 | Santamaria |
| 2016/0282255 A1 | 9/2016 | Irimia et al. |
| 2016/0287152 A1 | 10/2016 | Schwartz et al. |

FOREIGN PATENT DOCUMENTS

| | | |
|---|---|---|
| AU | 2016203838 A1 | 6/2016 |
| CN | 1464070 A | 12/2003 |
| CN | 101684503 A | 3/2010 |
| CN | 101852808 A | 10/2010 |
| CN | 102072931 A | 5/2011 |
| CN | 102147414 A | 8/2011 |
| CN | 102168066 A | 8/2011 |
| CN | 102234682 A | 11/2011 |
| CN | 102321762 A | 1/2012 |
| CN | 103266170 A | 8/2013 |
| CN | 103276087 A | 9/2013 |
| CN | 103333967 A | 10/2013 |
| CN | 104962570 A | 10/2015 |
| CN | 105648069 A | 6/2016 |
| CN | 105651992 A | 6/2016 |
| CN | 105755118 A | 7/2016 |
| DE | 102008013715 | 4/2010 |
| EP | 1328540 B1 | 3/2005 |
| EP | 837946 B1 | 3/2009 |
| EP | 1747295 B1 | 1/2012 |
| EP | 2842570 A1 | 3/2015 |
| JP | 2004354164 A | 12/2004 |
| JP | 2006158276 A | 6/2006 |
| JP | 2006328032 A | 12/2006 |
| JP | 2007262114 A | 10/2007 |
| JP | 2009068869 A | 4/2009 |
| JP | 2013092501 A | 5/2013 |
| JP | 2014514331 A | 6/2014 |
| JP | 2015173626 A | 10/2015 |
| KR | 100823684 B1 | 4/2008 |
| KR | 20110133843 A | 12/2011 |
| KR | 20130114932 A | 10/2013 |
| KR | 20130121550 A | 11/2013 |
| KR | 20140097679 A | 8/2014 |
| KR | 20150049697 A | 5/2015 |
| KR | 20150144644 A | 12/2015 |
| WO | WO1991017265 A1 | 11/1991 |
| WO | WO1992007952 A1 | 5/1992 |
| WO | WO1993025660 A1 | 12/1993 |
| WO | WO1995005399 A1 | 2/1995 |
| WO | WO1999002728 A1 | 1/1999 |
| WO | WO2000028088 A1 | 5/2000 |
| WO | WO2000040750 A1 | 7/2000 |
| WO | WO2001096023 A2 | 12/2001 |
| WO | WO2002031501 A1 | 4/2002 |
| WO | WO2002083292 A2 | 10/2002 |
| WO | WO2003035829 A2 | 5/2003 |
| WO | WO2004003142 A2 | 1/2004 |
| WO | WO2004015395 A2 | 2/2004 |
| WO | WO2004033497 A1 | 4/2004 |
| WO | WO2004053163 A1 | 6/2004 |
| WO | WO2004067742 A1 | 8/2004 |
| WO | WO2004106546 A1 | 12/2004 |
| WO | WO2005001113 A2 | 1/2005 |
| WO | WO2005021800 A2 | 3/2005 |
| WO | WO2005108612 A2 | 11/2005 |
| WO | WO2005111624 A2 | 11/2005 |
| WO | WO2006031883 A2 | 3/2006 |
| WO | WO2006076793 A1 | 7/2006 |
| WO | WO2007024676 A2 | 3/2007 |
| WO | WO2007024840 A2 | 3/2007 |
| WO | WO2007133807 A2 | 11/2007 |
| WO | WO2008001376 A2 | 1/2008 |
| WO | WO2008016680 A1 | 2/2008 |
| WO | WO2008017507 A2 | 2/2008 |
| WO | WO2008030071 A1 | 3/2008 |
| WO | WO2008090557 A2 | 7/2008 |
| WO | WO2008091364 A2 | 7/2008 |
| WO | WO2008157649 A1 | 12/2008 |
| WO | WO2009003492 A1 | 1/2009 |
| WO | WO2009055068 A1 | 4/2009 |
| WO | WO2009083856 A2 | 7/2009 |
| WO | WO2009106322 A1 | 9/2009 |
| WO | WO2009124296 A2 | 10/2009 |
| WO | WO2009149091 A1 | 12/2009 |
| WO | WO 2010/037395 A2 | 4/2010 |
| WO | WO2010037397 A1 | 4/2010 |
| WO | WO2011090445 A1 | 7/2011 |
| WO | WO2011100669 A2 | 8/2011 |
| WO | WO2011104497 A1 | 9/2011 |
| WO | WO 2012/044999 A2 | 4/2012 |
| WO | WO2012062904 A2 | 5/2012 |
| WO | WO2012111685 A1 | 8/2012 |
| WO | WO2012111686 A1 | 8/2012 |
| WO | WO2012111687 A1 | 8/2012 |
| WO | WO2012148960 A2 | 11/2012 |
| WO | WO2013071520 A1 | 5/2013 |
| WO | WO2013119793 A1 | 8/2013 |
| WO | WO2014124543 A1 | 8/2014 |
| WO | WO2014144892 A1 | 9/2014 |
| WO | WO2014189257 A1 | 11/2014 |
| WO | WO2014192937 A1 | 12/2014 |
| WO | WO2014197840 A1 | 12/2014 |
| WO | WO2015060417 A1 | 4/2015 |
| WO | WO2015100373 A2 | 7/2015 |
| WO | WO2015135856 A1 | 9/2015 |
| WO | WO2015161173 A1 | 10/2015 |
| WO | WO2015174862 A1 | 11/2015 |
| WO | WO2015200384 A1 | 12/2015 |
| WO | WO2016015027 A1 | 1/2016 |
| WO | WO2016075172 A1 | 5/2016 |
| WO | WO2016090115 A1 | 6/2016 |
| WO | WO2016115500 A1 | 7/2016 |
| WO | WO2016127158 A1 | 8/2016 |
| WO | WO2016160908 A1 | 10/2016 |

OTHER PUBLICATIONS

Coulie, Pierre G. et al.; "Tumour antigens recognized by T lymphocytes: at the core of cancer immunotherapy"; Nature Reviews Cancer; vol. 14; Feb. 2014; pp. 135-146.

Fritsch, Edward F. et al,; "HLA-binding properties of tumor neoepitopes in humans"; Cancer Immunol Res.; Jun. 2014; 2(6); pp. 522-529.

Kwong, Gabriel A. et al.; "Modular nucleic acid assembled p/MHC microarrays for multiplexed sorting of antigen-specific T cells"; J Am Chem Soc.; Jul. 22, 2009; 131(28); pp. 9695-9703.

(56) References Cited

OTHER PUBLICATIONS

Novak, Erik J. et al.; "MHC class II tetramers identify peptide-specific human CD44+T cells proliferating in response to influenza A antigen"; J Clin Invest.; Dec. 5, 1999; 104(12); pp. R63-R67.

Rodenko, Boris et al.; "Generation of peptide-MHC class I complexes through UV-mediated ligand exchange"; Nature Protocols; vol. 1; No. 3; 2006; pp. 1120-1132.

Sano, Takeshi et al.; "Expression of a cloned streptavidin gene in *Escherichia coli*"; Proc Natl Acad Sci USA; Jan. 1990; 87(1); pp. 142-146.

Toebes, Mireille et al.; "Design and use of conditional MHC class I ligands"; Nature Medicine; vol. 12; No. 2; Feb. 2006; pp. 246-251.

International Search Report and Written Opinion dated Nov. 29, 2016 in corresponding International Application No. PCT/US2016/035357, 11pp.

Stoeva, S.I. et al., "Multiplexed Detection of Protein Cancer Markers with Biobarcoded Nanoparticle Probes," Journal of the American Chemical Society, Jul. 5, 2006, vol. 128, No. 26, pp. 8378-8379.

Stone, D.J. et al., "HLA-restricted epitope identification and detection of functional Tcell responses by using MHC-peptide and costimulatory microarrays," Proceedings of the National Academy of Sciences of the United States of America, Mar. 8, 2005, vol. 102, No. 10, pp. 3744-3749.

Extended European Search Report, European Application No. 16804369.3, dated Dec. 13, 2018, 10 pages.

FIG. 4

| # | Name | DNA sequence |
|---|---|---|
| DNA for NP modification (5'-biotin-) | | |
| 1 | D1-D5-D9 | AA AAA AAA A GTG ATG AGT TTC AA ATC AGT CAA GAG AA CTC GTT CAC TAT AA CTG AAT CCT CGG GAT GCC TA |
| 2 | D1-D5-D10 | AA AAA AAA A GTG ATG AGT TTC AA ATC AGT CAA GAG AA CTT ACG AGT GTA AA CTG AAT CCT CGG GAT GCC TA |
| 3 | D1-D5-D11 | AA AAA AAA A GTG ATG AGT TTC AA ATC AGT CAA GAG AA TGT CTC TAA GTG AA CTG AAT CCT CGG GAT GCC TA |
| 4 | D1-D6-D9 | AA AAA AAA A GTG ATG AGT TTC AA GTA TTC GTC ATC AA CTC GTT CAC TAT AA CTG AAT CCT CGG GAT GCC TA |
| 5 | D1-D6-D10 | AA AAA AAA A GTG ATG AGT TTC AA GTA TTC GTC ATC AA CTT ACG AGT GTA AA CTG AAT CCT CGG GAT GCC TA |
| 6 | D1-D6-D11 | AA AAA AAA A GTG ATG AGT TTC AA GTA TTC GTC ATC AA TGT CTC TAA GTG AA CTG AAT CCT CGG GAT GCC TA |
| 7 | D1-D7-D9 | AA AAA AAA A GTG ATG AGT TTC AA GTC AGA TAG TTC AA CTC GTT CAC TAT AA CTG AAT CCT CGG GAT GCC TA |
| 8 | D1-D7-D10 | AA AAA AAA A GTG ATG AGT TTC AA GTC AGA TAG TTC AA CTT ACG AGT GTA AA CTG AAT CCT CGG GAT GCC TA |
| 9 | D1-D7-D11 | AA AAA AAA A GTG ATG AGT TTC AA GTC AGA TAG TTC AA TGT CTC TAA GTG AA CTG AAT CCT CGG GAT GCC TA |
| 10 | D2-D5-D9 | AA AAA AAA A CTA TGT CGA TAC AA ATC AGT CAA GAG AA CTC GTT CAC TAT AA CTG AAT CCT CGG GAT GCC TA |
| 11 | D2-D5-D10 | AA AAA AAA A CTA TGT CGA TAC AA ATC AGT CAA GAG AA CTT ACG AGT GTA AA CTG AAT CCT CGG GAT GCC TA |
| 12 | D2-D5-D11 | AA AAA AAA A CTA TGT CGA TAC AA ATC AGT CAA GAG AA TGT CTC TAA GTG AA CTG AAT CCT CGG GAT GCC TA |
| 13 | D2-D6-D9 | AA AAA AAA A CTA TGT CGA TAC AA GTA TTC GTC ATC AA CTC GTT CAC TAT AA CTG AAT CCT CGG GAT GCC TA |
| 14 | D2-D6-D10 | AA AAA AAA A CTA TGT CGA TAC AA GTA TTC GTC ATC AA CTT ACG AGT GTA AA CTG AAT CCT CGG GAT GCC TA |
| 15 | D2-D6-D11 | AA AAA AAA A CTA TGT CGA TAC AA GTA TTC GTC ATC AA TGT CTC TAA GTG AA CTG AAT CCT CGG GAT GCC TA |
| 16 | D2-D7-D9 | AA AAA AAA A CTA TGT CGA TAC AA GTC AGA TAG TTC AA CTC GTT CAC TAT AA CTG AAT CCT CGG GAT GCC TA |
| 17 | D2-D7-D10 | AA AAA AAA A CTA TGT CGA TAC AA GTC AGA TAG TTC AA CTT ACG AGT GTA AA CTG AAT CCT CGG GAT GCC TA |
| 18 | D2-D7-D11 | AA AAA AAA A CTA TGT CGA TAC AA GTC AGA TAG TTC AA TGT CTC TAA GTG AA CTG AAT CCT CGG GAT GCC TA |
| 19 | D3-D5-D9 | AA AAA AAA A TAC ATC CAA GAC AA ATC AGT CAA GAG AA CTC GTT CAC TAT AA CTG AAT CCT CGG GAT GCC TA |
| 20 | D3-D5-D10 | AA AAA AAA A TAC ATC CAA GAC AA ATC AGT CAA GAG AA CTT ACG AGT GTA AA CTG AAT CCT CGG GAT GCC TA | continued    FIG. 4

| # | Name | DNA sequence |
|---|---|---|
| DNA for NP modification (5'-biotin-) | | |
| 21 | D3-D5-D11 | AA AAA AAA A TAC ATC CAA GAC AA ATC AGT CAA GAG AA TGT CTC TAA GTG AA CTG AAT CCT CGG GAT GCC TA |
| 22 | D3-D6-D9 | AA AAA AAA A TAC ATC CAA GAC AA GTA TTC GTC ATC AA CTC GTT CAC TAT AA CTG AAT CCT CGG GAT GCC TA |
| 23 | D3-D6-D10 | AA AAA AAA A TAC ATC CAA GAC AA GTA TTC GTC ATC AA CTT ACG AGT GTA AA CTG AAT CCT CGG GAT GCC TA |
| 24 | D3-D6-D11 | AA AAA AAA A TAC ATC CAA GAC AA GTA TTC GTC ATC AA TGT CTC TAA GTG AA CTG AAT CCT CGG GAT GCC TA |
| 25 | D3-D7-D9 | AA AAA AAA A TAC ATC CAA GAC AA GTC AGA TAG TTC AA CTC GTT CAC TAT AA CTG AAT CCT CGG GAT GCC TA |
| 26 | D3-D7-D10 | AA AAA AAA A TAC ATC CAA GAC AA GTC AGA TAG TTC AA CTT ACG AGT GTA AA CTG AAT CCT CGG GAT GCC TA |
| 27 | D3-D7-D11 | AA AAA AAA A TAC ATC CAA GAC AA GTC AGA TAG TTC AA TGT CTC TAA GTG AA CTG AAT CCT CGG GAT GCC TA |

| DNA for barcoding | | |
|---|---|---|
| | M1 | 5-Cy5-AGC ACA GGG AAA CTC ATC AC |
| | M2 | 5-Cy3- GCA TCA TCG TAT CGA CAT AG |
| | M3 | 5-Alex488-ATG GTT CGG TCT TGG ATG TA |
| | M5 | 5-Cy5-CGC CAA TGC TCT TGA CTG AT |
| | M6 | 5-Cy3- AGG ACT TCG ATG ACG AAT AC |
| | M7 | 5-Alex488-ATC CTT GCG AAC TAT CTG AC |
| | M9 | 5-Cy5-GCC GTA TCA TAG TGA ACG AG |
| | M10 | 5-Cy3- CCA GCG ATT ACA CTC GTA AG |
| | M11 | 5-Alex488-CAG ACC TGC ACT TAG AGA CA |

FIG. 8B

| DNA for displacement | | |
|---|---|---|
| | M1 comp | GTG ATG AGT TTC CCT GTG CT |
| | M2 comp | CTA TGT CGA TAC GAT GAT GC |
| | M3 comp | TAC ATC CAA GAC CGA ACC AT |
| | M5 comp | ATC AGT CAA GAG CAT TGG CG |
| | M6 comp | GTA TTC GTC ATC GAA GTC CT |
| | M7 comp | GTC AGA TAG TTC GCA AGG AT |
| | M9 comp | CTC GTT CAC TAT GAT ACG GC |
| | M10 comp | CTT ACG AGT GTA ATC GCT GG |
| | M11 comp | TGT CTC TAA GTG CAG GTC TG |

SEQUENCE LISTING

<160> NUMBER OF SEQ ID NOS: 331

<210> SEQ ID NO 1
<211> LENGTH: 9
<212> TYPE: PRT
<213> ORGANISM: Homo sapiens

<400> SEQUENCE: 1

Phe Leu Gly Ser Leu Leu Ile Leu Val
1               5

<210> SEQ ID NO 2
<211> LENGTH: 9
<212> TYPE: PRT

```
<213> ORGANISM: Homo sapiens

<400> SEQUENCE: 2

Arg Leu Ser Ser Cys Phe Asp Tyr Val
1               5

<210> SEQ ID NO 3
<211> LENGTH: 9
<212> TYPE: PRT
<213> ORGANISM: Homo sapiens

<400> SEQUENCE: 3

Ser Leu Met Asn Glu Asp Phe Ile Leu
1               5

<210> SEQ ID NO 4
<211> LENGTH: 10
<212> TYPE: PRT
<213> ORGANISM: Homo sapiens

<400> SEQUENCE: 4

Phe Leu Gly Ser Leu Leu Ile Leu Val Val
1               5                   10

<210> SEQ ID NO 5
<211> LENGTH: 10
<212> TYPE: PRT
<213> ORGANISM: Homo sapiens

<400> SEQUENCE: 5

Ser Leu Met Asn Glu Asp Phe Ile Leu Ala
1               5                   10

<210> SEQ ID NO 6
<211> LENGTH: 9
<212> TYPE: PRT
<213> ORGANISM: Homo sapiens

<400> SEQUENCE: 6

Ser Leu His Asp Leu Thr Asp Gly Val
1               5

<210> SEQ ID NO 7
<211> LENGTH: 9
<212> TYPE: PRT
<213> ORGANISM: Homo sapiens

<400> SEQUENCE: 7

Lys Ala Trp Glu Asn Phe Pro Asn Val
1               5

<210> SEQ ID NO 8
<211> LENGTH: 9
<212> TYPE: PRT
<213> ORGANISM: Homo sapiens

<400> SEQUENCE: 8

Leu Leu Ser Glu Phe Phe Ser Cys Leu
1               5

<210> SEQ ID NO 9
<211> LENGTH: 10
<212> TYPE: PRT
<213> ORGANISM: Homo sapiens
```

```
<400> SEQUENCE: 9

Lys Leu Leu Ser Glu Phe Phe Ser Cys Leu
1               5                   10

<210> SEQ ID NO 10
<211> LENGTH: 10
<212> TYPE: PRT
<213> ORGANISM: Homo sapiens

<400> SEQUENCE: 10

Leu Gln Asp Ser Gly Leu Trp Phe Pro Val
1               5                   10

<210> SEQ ID NO 11
<211> LENGTH: 11
<212> TYPE: PRT
<213> ORGANISM: Homo sapiens

<400> SEQUENCE: 11

Ser Leu Met Asn Glu Asp Phe Ile Leu Ala Val
1               5                   10

<210> SEQ ID NO 12
<211> LENGTH: 9
<212> TYPE: PRT
<213> ORGANISM: Homo sapiens

<400> SEQUENCE: 12

Tyr Leu Tyr His Arg Val Asp Val Ile
1               5

<210> SEQ ID NO 13
<211> LENGTH: 10
<212> TYPE: PRT
<213> ORGANISM: Homo sapiens

<400> SEQUENCE: 13

Phe Val Ala Asn Leu Phe Asn Thr Tyr Leu
1               5                   10

<210> SEQ ID NO 14
<211> LENGTH: 10
<212> TYPE: PRT
<213> ORGANISM: Homo sapiens

<400> SEQUENCE: 14

Gly Leu Phe His Ser Leu Tyr Arg Ser Val
1               5                   10

<210> SEQ ID NO 15
<211> LENGTH: 9
<212> TYPE: PRT
<213> ORGANISM: Homo sapiens

<400> SEQUENCE: 15

Gly Leu Ser Glu Lys Cys Ser Leu Val
1               5

<210> SEQ ID NO 16
<211> LENGTH: 11
<212> TYPE: PRT
<213> ORGANISM: Homo sapiens

<400> SEQUENCE: 16
```

His Leu Gln Asp Ser Gly Leu Trp Phe Pro Val
1               5                   10

<210> SEQ ID NO 17
<211> LENGTH: 9
<212> TYPE: PRT
<213> ORGANISM: Homo sapiens

<400> SEQUENCE: 17

Thr Leu Ala Asn Arg Phe Ser Ala Val
1               5

<210> SEQ ID NO 18
<211> LENGTH: 10
<212> TYPE: PRT
<213> ORGANISM: Homo sapiens

<400> SEQUENCE: 18

Phe Leu Val Ile Val Pro Leu Ser Thr Ile
1               5                   10

<210> SEQ ID NO 19
<211> LENGTH: 10
<212> TYPE: PRT
<213> ORGANISM: Homo sapiens

<400> SEQUENCE: 19

Gly Leu Ser Glu Lys Cys Ser Leu Val Val
1               5                   10

<210> SEQ ID NO 20
<211> LENGTH: 11
<212> TYPE: PRT
<213> ORGANISM: Homo sapiens

<400> SEQUENCE: 20

Phe Leu His Gly Asn Ser Leu Tyr Gln Lys Val
1               5                   10

<210> SEQ ID NO 21
<211> LENGTH: 9
<212> TYPE: PRT
<213> ORGANISM: Homo sapiens

<400> SEQUENCE: 21

Phe Leu Arg Glu Ser Gln Glu Thr Leu
1               5

<210> SEQ ID NO 22
<211> LENGTH: 10
<212> TYPE: PRT
<213> ORGANISM: Homo sapiens

<400> SEQUENCE: 22

Leu Leu Ser Glu Phe Phe Ser Cys Leu Ala
1               5                   10

<210> SEQ ID NO 23
<211> LENGTH: 9
<212> TYPE: PRT
<213> ORGANISM: Homo sapiens

<400> SEQUENCE: 23

Gln Leu Asp Ser Gly Thr Leu Ile Val
1               5

```
<210> SEQ ID NO 24
<211> LENGTH: 9
<212> TYPE: PRT
<213> ORGANISM: Homo sapiens

<400> SEQUENCE: 24

Trp Met Gly Leu Leu Asp Leu Glu Val
1               5

<210> SEQ ID NO 25
<211> LENGTH: 9
<212> TYPE: PRT
<213> ORGANISM: Homo sapiens

<400> SEQUENCE: 25

Phe Val Leu Glu His Glu Asp Gly Leu
1               5

<210> SEQ ID NO 26
<211> LENGTH: 10
<212> TYPE: PRT
<213> ORGANISM: Homo sapiens

<400> SEQUENCE: 26

Thr Leu Val Ser Leu Ala Thr Glu Thr Val
1               5                   10

<210> SEQ ID NO 27
<211> LENGTH: 10
<212> TYPE: PRT
<213> ORGANISM: Homo sapiens

<400> SEQUENCE: 27

Lys Met Gly Lys Thr Ile Tyr Lys Tyr Val
1               5                   10

<210> SEQ ID NO 28
<211> LENGTH: 9
<212> TYPE: PRT
<213> ORGANISM: Homo sapiens

<400> SEQUENCE: 28

Asn Leu Phe Asn Thr Tyr Leu Cys Leu
1               5

<210> SEQ ID NO 29
<211> LENGTH: 9
<212> TYPE: PRT
<213> ORGANISM: Homo sapiens

<400> SEQUENCE: 29

Arg Leu Ser Glu Val Met Ala Arg Met
1               5

<210> SEQ ID NO 30
<211> LENGTH: 10
<212> TYPE: PRT
<213> ORGANISM: Homo sapiens

<400> SEQUENCE: 30

Val Leu Thr Glu Ile Phe Leu Gly Ser Leu
1               5                   10
```

```
<210> SEQ ID NO 31
<211> LENGTH: 11
<212> TYPE: PRT
<213> ORGANISM: Homo sapiens

<400> SEQUENCE: 31

Ala Leu Tyr Lys Glu Glu Glu Gln Glu Pro Val
1               5                   10

<210> SEQ ID NO 32
<211> LENGTH: 11
<212> TYPE: PRT
<213> ORGANISM: Homo sapiens

<400> SEQUENCE: 32

Val Leu Ile Asp Leu Ile Gln Arg Thr Lys Val
1               5                   10

<210> SEQ ID NO 33
<211> LENGTH: 10
<212> TYPE: PRT
<213> ORGANISM: Homo sapiens

<400> SEQUENCE: 33

Met Val Cys Thr Phe Cys Pro Pro Pro Leu
1               5                   10

<210> SEQ ID NO 34
<211> LENGTH: 10
<212> TYPE: PRT
<213> ORGANISM: Homo sapiens

<400> SEQUENCE: 34

Leu Leu Phe His Ser Pro Arg Ala His Leu
1               5                   10

<210> SEQ ID NO 35
<211> LENGTH: 11
<212> TYPE: PRT
<213> ORGANISM: Homo sapiens

<400> SEQUENCE: 35

Val Leu Leu His Ala Phe Glu Gly Tyr Asn Val
1               5                   10

<210> SEQ ID NO 36
<211> LENGTH: 9
<212> TYPE: PRT
<213> ORGANISM: Homo sapiens

<400> SEQUENCE: 36

Val Thr Ser Ser Ile Val Thr Leu Val
1               5

<210> SEQ ID NO 37
<211> LENGTH: 10
<212> TYPE: PRT
<213> ORGANISM: Homo sapiens

<400> SEQUENCE: 37

Ser Leu Ala Pro Pro Arg Thr Pro Glu Leu
1               5                   10

<210> SEQ ID NO 38
<211> LENGTH: 9
```

<210> SEQ ID NO 38
<211> LENGTH: 8 (not visible, assumed)
<212> TYPE: PRT
<213> ORGANISM: Homo sapiens

<400> SEQUENCE: 38

Phe Phe Val Glu Ala Ser Met Ser Val
1               5

<210> SEQ ID NO 39
<211> LENGTH: 11
<212> TYPE: PRT
<213> ORGANISM: Homo sapiens

<400> SEQUENCE: 39

Ser Met Leu Thr Ala Arg Ser Trp Asp Ser Val
1               5                   10

<210> SEQ ID NO 40
<211> LENGTH: 11
<212> TYPE: PRT
<213> ORGANISM: Homo sapiens

<400> SEQUENCE: 40

Phe Val Leu Glu His Glu Asp Gly Leu Asn Leu
1               5                   10

<210> SEQ ID NO 41
<211> LENGTH: 9
<212> TYPE: PRT
<213> ORGANISM: Homo sapiens

<400> SEQUENCE: 41

Ser Leu Gln Thr Asn Val Gln Arg Leu
1               5

<210> SEQ ID NO 42
<211> LENGTH: 9
<212> TYPE: PRT
<213> ORGANISM: Homo sapiens

<400> SEQUENCE: 42

Lys Val Lys Cys Ile Pro Phe Ala Val
1               5

<210> SEQ ID NO 43
<211> LENGTH: 10
<212> TYPE: PRT
<213> ORGANISM: Homo sapiens

<400> SEQUENCE: 43

Phe Val Phe Ser Lys Tyr Cys His Arg Ala
1               5                   10

<210> SEQ ID NO 44
<211> LENGTH: 10
<212> TYPE: PRT
<213> ORGANISM: Homo sapiens

<400> SEQUENCE: 44

Ser Leu Val Pro Glu Asp Glu Ala Asn Ile
1               5                   10

<210> SEQ ID NO 45
<211> LENGTH: 10
<212> TYPE: PRT
<213> ORGANISM: Homo sapiens

<400> SEQUENCE: 45

Ile Leu Pro Phe Phe Tyr Leu Gly Ser Ala
1               5                   10

<210> SEQ ID NO 46
<211> LENGTH: 11
<212> TYPE: PRT
<213> ORGANISM: Homo sapiens

<400> SEQUENCE: 46

Arg Ile Ala Gly Glu Glu Val Thr Leu Thr Val
1               5                   10

<210> SEQ ID NO 47
<211> LENGTH: 10
<212> TYPE: PRT
<213> ORGANISM: Homo sapiens

<400> SEQUENCE: 47

Val Leu Thr Arg Leu Ala Leu Leu Gln Leu
1               5                   10

<210> SEQ ID NO 48
<211> LENGTH: 11
<212> TYPE: PRT
<213> ORGANISM: Homo sapiens

<400> SEQUENCE: 48

Leu Leu Glu Tyr Arg Ile Ser Glu Asn Pro Val
1               5                   10

<210> SEQ ID NO 49
<211> LENGTH: 11
<212> TYPE: PRT
<213> ORGANISM: Homo sapiens

<400> SEQUENCE: 49

Met Gln Gln Pro Ser Pro Gln Ile Pro Pro Val
1               5                   10

<210> SEQ ID NO 50
<211> LENGTH: 9
<212> TYPE: PRT
<213> ORGANISM: Homo sapiens

<400> SEQUENCE: 50

Gly Leu Phe His Ser Leu Tyr Arg Ser
1               5

<210> SEQ ID NO 51
<211> LENGTH: 9
<212> TYPE: PRT
<213> ORGANISM: Homo sapiens

<400> SEQUENCE: 51

Ser Leu Gly Ser Leu Leu Ile Leu Val
1               5

<210> SEQ ID NO 52
<211> LENGTH: 9
<212> TYPE: PRT
<213> ORGANISM: Homo sapiens

<400> SEQUENCE: 52

Arg Leu Pro Ser Cys Phe Asp Tyr Val
1               5

<210> SEQ ID NO 53
<211> LENGTH: 9
<212> TYPE: PRT
<213> ORGANISM: Homo sapiens

<400> SEQUENCE: 53

Pro Leu Met Asn Glu Asp Phe Ile Leu
1               5

<210> SEQ ID NO 54
<211> LENGTH: 10
<212> TYPE: PRT
<213> ORGANISM: Homo sapiens

<400> SEQUENCE: 54

Ser Leu Gly Ser Leu Leu Ile Leu Val Val
1               5                   10

<210> SEQ ID NO 55
<211> LENGTH: 10
<212> TYPE: PRT
<213> ORGANISM: Homo sapiens

<400> SEQUENCE: 55

Pro Leu Met Asn Glu Asp Phe Ile Leu Ala
1               5                   10

<210> SEQ ID NO 56
<211> LENGTH: 9
<212> TYPE: PRT
<213> ORGANISM: Homo sapiens

<400> SEQUENCE: 56

Ser Leu His Gly Leu Thr Asp Gly Val
1               5

<210> SEQ ID NO 57
<211> LENGTH: 9
<212> TYPE: PRT
<213> ORGANISM: Homo sapiens

<400> SEQUENCE: 57

Lys Ala Trp Glu Asn Ser Pro Asn Val
1               5

<210> SEQ ID NO 58
<211> LENGTH: 9
<212> TYPE: PRT
<213> ORGANISM: Homo sapiens

<400> SEQUENCE: 58

Leu Leu Ser Glu Phe Ser Ser Cys Leu
1               5

<210> SEQ ID NO 59
<211> LENGTH: 10
<212> TYPE: PRT
<213> ORGANISM: Homo sapiens

<400> SEQUENCE: 59

Lys Leu Leu Ser Glu Phe Ser Ser Cys Leu

<210> SEQ ID NO 60
<211> LENGTH: 10
<212> TYPE: PRT
<213> ORGANISM: Homo sapiens

<400> SEQUENCE: 60

Leu Arg Asp Ser Gly Leu Trp Phe Pro Val
1               5                   10

<210> SEQ ID NO 61
<211> LENGTH: 11
<212> TYPE: PRT
<213> ORGANISM: Homo sapiens

<400> SEQUENCE: 61

Pro Leu Met Asn Glu Asp Phe Ile Leu Ala Val
1               5                   10

<210> SEQ ID NO 62
<211> LENGTH: 9
<212> TYPE: PRT
<213> ORGANISM: Homo sapiens

<400> SEQUENCE: 62

Asp Leu Tyr His Arg Val Asp Val Ile
1               5

<210> SEQ ID NO 63
<211> LENGTH: 10
<212> TYPE: PRT
<213> ORGANISM: Homo sapiens

<400> SEQUENCE: 63

Phe Val Ala Asn Leu Phe Asn Thr Tyr Pro
1               5                   10

<210> SEQ ID NO 64
<211> LENGTH: 10
<212> TYPE: PRT
<213> ORGANISM: Homo sapiens

<400> SEQUENCE: 64

Gly Leu Phe Arg Ser Leu Tyr Arg Ser Val
1               5                   10

<210> SEQ ID NO 65
<211> LENGTH: 9
<212> TYPE: PRT
<213> ORGANISM: Homo sapiens

<400> SEQUENCE: 65

Gly Leu Ser Gly Lys Cys Ser Leu Val
1               5

<210> SEQ ID NO 66
<211> LENGTH: 11
<212> TYPE: PRT
<213> ORGANISM: Homo sapiens

<400> SEQUENCE: 66

His Leu Arg Asp Ser Gly Leu Trp Phe Pro Val
1               5                   10

<210> SEQ ID NO 67
<211> LENGTH: 9
<212> TYPE: PRT
<213> ORGANISM: Homo sapiens

<400> SEQUENCE: 67

Thr Leu Ala Asn Arg Phe Pro Ala Val
1               5

<210> SEQ ID NO 68
<211> LENGTH: 10
<212> TYPE: PRT
<213> ORGANISM: Homo sapiens

<400> SEQUENCE: 68

Phe Leu Val Ile Ala Pro Leu Ser Thr Ile
1               5                   10

<210> SEQ ID NO 69
<211> LENGTH: 10
<212> TYPE: PRT
<213> ORGANISM: Homo sapiens

<400> SEQUENCE: 69

Gly Leu Ser Gly Lys Cys Ser Leu Val Val
1               5                   10

<210> SEQ ID NO 70
<211> LENGTH: 11
<212> TYPE: PRT
<213> ORGANISM: Homo sapiens

<400> SEQUENCE: 70

Pro Leu His Gly Asn Ser Leu Tyr Gln Lys Val
1               5                   10

<210> SEQ ID NO 71
<211> LENGTH: 9
<212> TYPE: PRT
<213> ORGANISM: Homo sapiens

<400> SEQUENCE: 71

Ser Leu Arg Glu Ser Gln Glu Thr Leu
1               5

<210> SEQ ID NO 72
<211> LENGTH: 10
<212> TYPE: PRT
<213> ORGANISM: Homo sapiens

<400> SEQUENCE: 72

Leu Leu Ser Glu Phe Ser Ser Cys Leu Ala
1               5                   10

<210> SEQ ID NO 73
<211> LENGTH: 9
<212> TYPE: PRT
<213> ORGANISM: Homo sapiens

<400> SEQUENCE: 73

Gln Leu Asp Pro Gly Thr Leu Ile Val
1               5

<210> SEQ ID NO 74

```
<211> LENGTH: 9
<212> TYPE: PRT
<213> ORGANISM: Homo sapiens

<400> SEQUENCE: 74

Trp Met Gly Leu Pro Asp Leu Glu Val
1               5

<210> SEQ ID NO 75
<211> LENGTH: 9
<212> TYPE: PRT
<213> ORGANISM: Homo sapiens

<400> SEQUENCE: 75

Phe Val Leu Asp His Glu Asp Gly Leu
1               5

<210> SEQ ID NO 76
<211> LENGTH: 10
<212> TYPE: PRT
<213> ORGANISM: Homo sapiens

<400> SEQUENCE: 76

Thr Pro Val Ser Leu Ala Thr Glu Thr Val
1               5                   10

<210> SEQ ID NO 77
<211> LENGTH: 10
<212> TYPE: PRT
<213> ORGANISM: Homo sapiens

<400> SEQUENCE: 77

Lys Met Gly Lys Thr Ile His Lys Tyr Val
1               5                   10

<210> SEQ ID NO 78
<211> LENGTH: 9
<212> TYPE: PRT
<213> ORGANISM: Homo sapiens

<400> SEQUENCE: 78

Asn Leu Phe Asn Thr Tyr Pro Cys Leu
1               5

<210> SEQ ID NO 79
<211> LENGTH: 9
<212> TYPE: PRT
<213> ORGANISM: Homo sapiens

<400> SEQUENCE: 79

Arg Leu Ser Glu Ala Met Ala Arg Met
1               5

<210> SEQ ID NO 80
<211> LENGTH: 10
<212> TYPE: PRT
<213> ORGANISM: Homo sapiens

<400> SEQUENCE: 80

Val Leu Thr Glu Ile Ser Leu Gly Ser Leu
1               5                   10

<210> SEQ ID NO 81
<211> LENGTH: 11
<212> TYPE: PRT
```

```
<213> ORGANISM: Homo sapiens

<400> SEQUENCE: 81

Ala Leu Tyr Lys Glu Gly Glu Gln Glu Pro Val
1               5                   10

<210> SEQ ID NO 82
<211> LENGTH: 11
<212> TYPE: PRT
<213> ORGANISM: Homo sapiens

<400> SEQUENCE: 82

Val Leu Ile Asp Leu Ile Gln Arg Thr Lys Asp
1               5                   10

<210> SEQ ID NO 83
<211> LENGTH: 10
<212> TYPE: PRT
<213> ORGANISM: Homo sapiens

<400> SEQUENCE: 83

Met Val Arg Thr Phe Cys Pro Pro Pro Leu
1               5                   10

<210> SEQ ID NO 84
<211> LENGTH: 10
<212> TYPE: PRT
<213> ORGANISM: Homo sapiens

<400> SEQUENCE: 84

Leu Leu Phe His Pro Pro Arg Ala His Leu
1               5                   10

<210> SEQ ID NO 85
<211> LENGTH: 11
<212> TYPE: PRT
<213> ORGANISM: Homo sapiens

<400> SEQUENCE: 85

Met Leu Leu His Ala Phe Glu Gly Tyr Asn Val
1               5                   10

<210> SEQ ID NO 86
<211> LENGTH: 9
<212> TYPE: PRT
<213> ORGANISM: Homo sapiens

<400> SEQUENCE: 86

Val Thr Ser Ser Ile Val Thr Pro Val
1               5

<210> SEQ ID NO 87
<211> LENGTH: 10
<212> TYPE: PRT
<213> ORGANISM: Homo sapiens

<400> SEQUENCE: 87

Ser Pro Ala Pro Pro Arg Thr Pro Glu Leu
1               5                   10

<210> SEQ ID NO 88
<211> LENGTH: 9
<212> TYPE: PRT
<213> ORGANISM: Homo sapiens
```

```
<400> SEQUENCE: 88

Ser Phe Val Glu Ala Ser Met Ser Val
1               5

<210> SEQ ID NO 89
<211> LENGTH: 11
<212> TYPE: PRT
<213> ORGANISM: Homo sapiens

<400> SEQUENCE: 89

Cys Met Leu Thr Ala Arg Ser Trp Asp Ser Val
1               5                   10

<210> SEQ ID NO 90
<211> LENGTH: 11
<212> TYPE: PRT
<213> ORGANISM: Homo sapiens

<400> SEQUENCE: 90

Phe Val Leu Asp His Glu Asp Gly Leu Asn Leu
1               5                   10

<210> SEQ ID NO 91
<211> LENGTH: 9
<212> TYPE: PRT
<213> ORGANISM: Homo sapiens

<400> SEQUENCE: 91

Ser Leu Gln Ala Asn Val Gln Arg Leu
1               5

<210> SEQ ID NO 92
<211> LENGTH: 9
<212> TYPE: PRT
<213> ORGANISM: Homo sapiens

<400> SEQUENCE: 92

Lys Val Lys Cys Ile Pro Tyr Ala Val
1               5

<210> SEQ ID NO 93
<211> LENGTH: 10
<212> TYPE: PRT
<213> ORGANISM: Homo sapiens

<400> SEQUENCE: 93

Phe Val Phe Ser Lys Tyr Arg His Arg Ala
1               5                   10

<210> SEQ ID NO 94
<211> LENGTH: 10
<212> TYPE: PRT
<213> ORGANISM: Homo sapiens

<400> SEQUENCE: 94

Asn Leu Val Pro Glu Asp Glu Ala Asn Ile
1               5                   10

<210> SEQ ID NO 95
<211> LENGTH: 10
<212> TYPE: PRT
<213> ORGANISM: Homo sapiens

<400> SEQUENCE: 95
```

```
Ile Leu Pro Phe Leu Tyr Leu Gly Ser Ala
1               5                   10

<210> SEQ ID NO 96
<211> LENGTH: 11
<212> TYPE: PRT
<213> ORGANISM: Homo sapiens

<400> SEQUENCE: 96

Arg Asn Ala Gly Glu Glu Val Thr Leu Thr Val
1               5                   10

<210> SEQ ID NO 97
<211> LENGTH: 10
<212> TYPE: PRT
<213> ORGANISM: Homo sapiens

<400> SEQUENCE: 97

Val Leu Ala Arg Leu Ala Leu Leu Gln Leu
1               5                   10

<210> SEQ ID NO 98
<211> LENGTH: 11
<212> TYPE: PRT
<213> ORGANISM: Homo sapiens

<400> SEQUENCE: 98

Leu Leu Glu Tyr Arg Ser Ser Glu Asn Pro Val
1               5                   10

<210> SEQ ID NO 99
<211> LENGTH: 11
<212> TYPE: PRT
<213> ORGANISM: Homo sapiens

<400> SEQUENCE: 99

Met Gln Gln Pro Ser Pro Pro Ile Pro Pro Val
1               5                   10

<210> SEQ ID NO 100
<211> LENGTH: 9
<212> TYPE: PRT
<213> ORGANISM: Homo sapiens

<400> SEQUENCE: 100

Gly Leu Phe Arg Ser Leu Tyr Arg Ser
1               5

<210> SEQ ID NO 101
<211> LENGTH: 9
<212> TYPE: PRT
<213> ORGANISM: Homo sapiens

<400> SEQUENCE: 101

Leu Leu Thr Asp Leu Leu Phe Leu Ile
1               5

<210> SEQ ID NO 102
<211> LENGTH: 10
<212> TYPE: PRT
<213> ORGANISM: Homo sapiens

<400> SEQUENCE: 102

Arg Leu Met Glu Arg Ser Ile Tyr Ser Ala
1               5                   10
```

```
<210> SEQ ID NO 103
<211> LENGTH: 9
<212> TYPE: PRT
<213> ORGANISM: Homo sapiens

<400> SEQUENCE: 103

Phe Leu Val Asn Asp Trp Leu Leu Val
1               5

<210> SEQ ID NO 104
<211> LENGTH: 10
<212> TYPE: PRT
<213> ORGANISM: Homo sapiens

<400> SEQUENCE: 104

Phe Leu Asp Ser Cys Pro His Leu Pro Leu
1               5                   10

<210> SEQ ID NO 105
<211> LENGTH: 9
<212> TYPE: PRT
<213> ORGANISM: Homo sapiens

<400> SEQUENCE: 105

Lys Met Asn Glu Leu Asn Tyr Cys Ile
1               5

<210> SEQ ID NO 106
<211> LENGTH: 10
<212> TYPE: PRT
<213> ORGANISM: Homo sapiens

<400> SEQUENCE: 106

Arg Leu Leu Thr Asp Leu Leu Phe Leu Ile
1               5                   10

<210> SEQ ID NO 107
<211> LENGTH: 9
<212> TYPE: PRT
<213> ORGANISM: Homo sapiens

<400> SEQUENCE: 107

Arg Leu Ala Asn Leu Ile Trp Arg Ala
1               5

<210> SEQ ID NO 108
<211> LENGTH: 9
<212> TYPE: PRT
<213> ORGANISM: Homo sapiens

<400> SEQUENCE: 108

Arg Leu Leu Thr Asp Leu Leu Phe Leu
1               5

<210> SEQ ID NO 109
<211> LENGTH: 10
<212> TYPE: PRT
<213> ORGANISM: Homo sapiens

<400> SEQUENCE: 109

Arg Ile Tyr Thr Glu Met Cys Phe Thr Val
1               5                   10
```

-continued

```
<210> SEQ ID NO 110
<211> LENGTH: 9
<212> TYPE: PRT
<213> ORGANISM: Homo sapiens

<400> SEQUENCE: 110

Val Leu Phe Glu Lys Lys Asp Phe Val
1               5

<210> SEQ ID NO 111
<211> LENGTH: 9
<212> TYPE: PRT
<213> ORGANISM: Homo sapiens

<400> SEQUENCE: 111

Lys Ile Phe Cys Ala Ser Phe Arg Ile
1               5

<210> SEQ ID NO 112
<211> LENGTH: 9
<212> TYPE: PRT
<213> ORGANISM: Homo sapiens

<400> SEQUENCE: 112

Phe Leu Ile Glu Thr Asp Ile Gln Met
1               5

<210> SEQ ID NO 113
<211> LENGTH: 10
<212> TYPE: PRT
<213> ORGANISM: Homo sapiens

<400> SEQUENCE: 113

Gln Leu Phe Gln Leu Tyr Asn Phe Glu Leu
1               5                   10

<210> SEQ ID NO 114
<211> LENGTH: 10
<212> TYPE: PRT
<213> ORGANISM: Homo sapiens

<400> SEQUENCE: 114

Val Leu Tyr Phe Asn His Tyr Phe Pro Ala
1               5                   10

<210> SEQ ID NO 115
<211> LENGTH: 9
<212> TYPE: PRT
<213> ORGANISM: Homo sapiens

<400> SEQUENCE: 115

Thr Val Leu Gly Thr Pro Phe Glu Val
1               5

<210> SEQ ID NO 116
<211> LENGTH: 10
<212> TYPE: PRT
<213> ORGANISM: Homo sapiens

<400> SEQUENCE: 116

Ser Ile Tyr Ser Ala Arg Tyr Ile Phe Val
1               5                   10

<210> SEQ ID NO 117
<211> LENGTH: 9
```

<212> TYPE: PRT
<213> ORGANISM: Homo sapiens

<400> SEQUENCE: 117

Tyr Leu Ala His Trp Leu Tyr Tyr Tyr
1               5

<210> SEQ ID NO 118
<211> LENGTH: 9
<212> TYPE: PRT
<213> ORGANISM: Homo sapiens

<400> SEQUENCE: 118

Lys Ile Ser Ser Gln Pro Pro Pro Val
1               5

<210> SEQ ID NO 119
<211> LENGTH: 9
<212> TYPE: PRT
<213> ORGANISM: Homo sapiens

<400> SEQUENCE: 119

Lys Leu Ser Thr Phe Leu Met Lys Ala
1               5

<210> SEQ ID NO 120
<211> LENGTH: 9
<212> TYPE: PRT
<213> ORGANISM: Homo sapiens

<400> SEQUENCE: 120

Phe Thr Leu Phe Glu Leu Ala Phe Leu
1               5

<210> SEQ ID NO 121
<211> LENGTH: 10
<212> TYPE: PRT
<213> ORGANISM: Homo sapiens

<400> SEQUENCE: 121

Phe Leu Pro Arg Lys Glu Asn Ile Ser Val
1               5                   10

<210> SEQ ID NO 122
<211> LENGTH: 10
<212> TYPE: PRT
<213> ORGANISM: Homo sapiens

<400> SEQUENCE: 122

Val Leu Gln Gly Cys Leu Pro Cys Pro Val
1               5                   10

<210> SEQ ID NO 123
<211> LENGTH: 9
<212> TYPE: PRT
<213> ORGANISM: Homo sapiens

<400> SEQUENCE: 123

Phe Leu Ala Asn Ser Gly Gly Trp Val
1               5

<210> SEQ ID NO 124
<211> LENGTH: 9
<212> TYPE: PRT
<213> ORGANISM: Homo sapiens

```
<400> SEQUENCE: 124

Tyr Ile Leu Leu Tyr Lys Asn Gly Val
1               5

<210> SEQ ID NO 125
<211> LENGTH: 9
<212> TYPE: PRT
<213> ORGANISM: Homo sapiens

<400> SEQUENCE: 125

Phe Leu Tyr Lys Ser Gln Gly Glu Ile
1               5

<210> SEQ ID NO 126
<211> LENGTH: 9
<212> TYPE: PRT
<213> ORGANISM: Homo sapiens

<400> SEQUENCE: 126

Phe Ile Ser Trp Gly Pro Ala Ser Ile
1               5

<210> SEQ ID NO 127
<211> LENGTH: 9
<212> TYPE: PRT
<213> ORGANISM: Homo sapiens

<400> SEQUENCE: 127

Leu Leu Tyr Glu Leu Gln Pro Gly Thr
1               5

<210> SEQ ID NO 128
<211> LENGTH: 9
<212> TYPE: PRT
<213> ORGANISM: Homo sapiens

<400> SEQUENCE: 128

Asn Leu Tyr Glu Glu Asp Ala Leu Leu
1               5

<210> SEQ ID NO 129
<211> LENGTH: 9
<212> TYPE: PRT
<213> ORGANISM: Homo sapiens

<400> SEQUENCE: 129

Leu Leu Thr Asp Leu Leu Phe Ser Ile
1               5

<210> SEQ ID NO 130
<211> LENGTH: 10
<212> TYPE: PRT
<213> ORGANISM: Homo sapiens

<400> SEQUENCE: 130

Arg Leu Met Glu Arg Ser Ile His Ser Ala
1               5                   10

<210> SEQ ID NO 131
<211> LENGTH: 9
<212> TYPE: PRT
<213> ORGANISM: Homo sapiens

<400> SEQUENCE: 131
```

Phe Leu Val Asn Asp Trp Leu Ser Val
1               5

<210> SEQ ID NO 132
<211> LENGTH: 10
<212> TYPE: PRT
<213> ORGANISM: Homo sapiens

<400> SEQUENCE: 132

Phe Leu Asp Ser Ser Pro His Leu Pro Leu
1               5                   10

<210> SEQ ID NO 133
<211> LENGTH: 9
<212> TYPE: PRT
<213> ORGANISM: Homo sapiens

<400> SEQUENCE: 133

Lys Met Asn Glu Leu Asn His Cys Ile
1               5

<210> SEQ ID NO 134
<211> LENGTH: 10
<212> TYPE: PRT
<213> ORGANISM: Homo sapiens

<400> SEQUENCE: 134

Arg Leu Leu Thr Asp Leu Leu Phe Ser Ile
1               5                   10

<210> SEQ ID NO 135
<211> LENGTH: 9
<212> TYPE: PRT
<213> ORGANISM: Homo sapiens

<400> SEQUENCE: 135

Arg Leu Ala Asn Leu Ile Arg Arg Ala
1               5

<210> SEQ ID NO 136
<211> LENGTH: 9
<212> TYPE: PRT
<213> ORGANISM: Homo sapiens

<400> SEQUENCE: 136

Arg Leu Leu Thr Asp Leu Leu Phe Ser
1               5

<210> SEQ ID NO 137
<211> LENGTH: 10
<212> TYPE: PRT
<213> ORGANISM: Homo sapiens

<400> SEQUENCE: 137

Arg Ile Tyr Thr Glu Met Arg Phe Thr Val
1               5                   10

<210> SEQ ID NO 138
<211> LENGTH: 9
<212> TYPE: PRT
<213> ORGANISM: Homo sapiens

<400> SEQUENCE: 138

Val Pro Phe Glu Lys Lys Asp Phe Val

<210> SEQ ID NO 139
<211> LENGTH: 9
<212> TYPE: PRT
<213> ORGANISM: Homo sapiens

<400> SEQUENCE: 139

Lys Ile Phe Cys Ala Ser Ser Arg Ile
1               5

<210> SEQ ID NO 140
<211> LENGTH: 9
<212> TYPE: PRT
<213> ORGANISM: Homo sapiens

<400> SEQUENCE: 140

Phe Ser Ile Glu Thr Asp Ile Gln Met
1               5

<210> SEQ ID NO 141
<211> LENGTH: 10
<212> TYPE: PRT
<213> ORGANISM: Homo sapiens

<400> SEQUENCE: 141

Gln Leu Phe Gln Pro Tyr Asn Phe Glu Leu
1               5                   10

<210> SEQ ID NO 142
<211> LENGTH: 10
<212> TYPE: PRT
<213> ORGANISM: Homo sapiens

<400> SEQUENCE: 142

Val Leu Tyr Phe His His Tyr Phe Pro Ala
1               5                   10

<210> SEQ ID NO 143
<211> LENGTH: 9
<212> TYPE: PRT
<213> ORGANISM: Homo sapiens

<400> SEQUENCE: 143

Thr Val Leu Gly Thr Pro Ser Glu Val
1               5

<210> SEQ ID NO 144
<211> LENGTH: 10
<212> TYPE: PRT
<213> ORGANISM: Homo sapiens

<400> SEQUENCE: 144

Ser Ile His Ser Ala Arg Tyr Ile Phe Val
1               5                   10

<210> SEQ ID NO 145
<211> LENGTH: 9
<212> TYPE: PRT
<213> ORGANISM: Homo sapiens

<400> SEQUENCE: 145

Tyr Leu Ala His Trp Leu Tyr His Tyr
1               5

<210> SEQ ID NO 146
<211> LENGTH: 9
<212> TYPE: PRT
<213> ORGANISM: Homo sapiens

<400> SEQUENCE: 146

Lys Ile Pro Ser Gln Pro Pro Pro Val
1               5

<210> SEQ ID NO 147
<211> LENGTH: 9
<212> TYPE: PRT
<213> ORGANISM: Homo sapiens

<400> SEQUENCE: 147

Lys Ser Ser Thr Phe Leu Met Lys Ala
1               5

<210> SEQ ID NO 148
<211> LENGTH: 9
<212> TYPE: PRT
<213> ORGANISM: Homo sapiens

<400> SEQUENCE: 148

Phe Thr Leu Phe Glu Leu Ala Ser Leu
1               5

<210> SEQ ID NO 149
<211> LENGTH: 10
<212> TYPE: PRT
<213> ORGANISM: Homo sapiens

<400> SEQUENCE: 149

Phe Leu Pro Arg Lys Glu Asn Ser Ser Val
1               5                   10

<210> SEQ ID NO 150
<211> LENGTH: 10
<212> TYPE: PRT
<213> ORGANISM: Homo sapiens

<400> SEQUENCE: 150

Val Leu Gln Gly Arg Leu Pro Cys Pro Val
1               5                   10

<210> SEQ ID NO 151
<211> LENGTH: 9
<212> TYPE: PRT
<213> ORGANISM: Homo sapiens

<400> SEQUENCE: 151

Ser Leu Ala Asn Ser Gly Gly Trp Val
1               5

<210> SEQ ID NO 152
<211> LENGTH: 9
<212> TYPE: PRT
<213> ORGANISM: Homo sapiens

<400> SEQUENCE: 152

Tyr Ile Leu Leu Tyr Lys Asp Gly Val
1               5

<210> SEQ ID NO 153

```
<211> LENGTH: 9
<212> TYPE: PRT
<213> ORGANISM: Homo sapiens

<400> SEQUENCE: 153

Ser Leu Tyr Lys Ser Gln Gly Glu Ile
1               5

<210> SEQ ID NO 154
<211> LENGTH: 9
<212> TYPE: PRT
<213> ORGANISM: Homo sapiens

<400> SEQUENCE: 154

Phe Ile Pro Trp Gly Pro Ala Ser Ile
1               5

<210> SEQ ID NO 155
<211> LENGTH: 9
<212> TYPE: PRT
<213> ORGANISM: Homo sapiens

<400> SEQUENCE: 155

Leu Ser Tyr Glu Leu Gln Pro Gly Thr
1               5

<210> SEQ ID NO 156
<211> LENGTH: 9
<212> TYPE: PRT
<213> ORGANISM: Homo sapiens

<400> SEQUENCE: 156

Asn Leu His Glu Glu Asp Ala Leu Leu
1               5

<210> SEQ ID NO 157
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
aaaaaaaaaa taggcatccc gaggattcag                                      30

<210> SEQ ID NO 158
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: (S)-3-(Fmoc-amino)-3-(2-nitrophenyl)propionic
      acid

<400> SEQUENCE: 158

Lys Ile Leu Gly Phe Val Phe Xaa Val
1               5

<210> SEQ ID NO 159
<211> LENGTH: 27
<212> TYPE: DNA
<213> ORGANISM: Artificial Sequence
```

<220> FEATURE:
<223> OTHER INFORMATION: Description of Artificial Sequence: Synthetic
      primer

<400> SEQUENCE: 159
gccacagcac tgttgctctt gaagtcc                                       27

<210> SEQ ID NO 160
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
ccaccagctc agctccacgt g                                             21

<210> SEQ ID NO 161
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
tggcctgctt tgtttgccgt ggttacagga agcctcagca                         40

<210> SEQ ID NO 162
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
gccacagcac tgttgctctt gaagtccata g                                  31

<210> SEQ ID NO 163
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
cgggctcctt tgcctaccgt gcctgcagga gggctcggca                         40

<210> SEQ ID NO 164
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
cgtgctgacc ccactgtgca cctccttccc attcacccac cagctcagct ccacgtggtc   60

<210> SEQ ID NO 165
<211> LENGTH: 40
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 165
tacaggaagc ctcagcagga caaagccttg agcagccctc                               40

<210> SEQ ID NO 166
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
tacaggaagc ctcagcagga caaaacattg accagcccac tg                            42

<210> SEQ ID NO 167
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
tacaggaagc ctcagcaaag gaccaagtgt ttcagccttc cac                           43

<210> SEQ ID NO 168
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
tacaggaagc ctcagcagct cagtcagtgg ctcagccgga                               40

<210> SEQ ID NO 169
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
tacaggaagc ctcagcactt gctaagacca cccagcccat c                             41

<210> SEQ ID NO 170
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
tacaggaagc ctcagcagga gaggatgtgg agcagagtct tttcc                         45

<210> SEQ ID NO 171
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 171
tacaggaagc ctcagcaagc caaaagatag aacagaattc cgaggc                46

<210> SEQ ID NO 172
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
tacaggaagc ctcagcagag gccctgaaca ttcaggaggg                       40

<210> SEQ ID NO 173
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
tacaggaagc ctcagcagaa aaccaggtgg agcacagccc                       40

<210> SEQ ID NO 174
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
tacaggaagc ctcagcagcc cagtctgtga gccagcataa cc                    42

<210> SEQ ID NO 175
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
tacaggaagc ctcagcagcc cagtcggtga cccagcttg                        39

<210> SEQ ID NO 176
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
tacaggaagc ctcagcagcc cagtcggtga cccagcttag                       40

<210> SEQ ID NO 177
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 177
tacaggaagc ctcagcagcc cagtcagtga cccagcctg                                   39

<210> SEQ ID NO 178
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
tacaggaagc ctcagcactc ttctggtatg tgcaataccc caacc                            45

<210> SEQ ID NO 179
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
tacaggaagc ctcagcagtt gaaccatatc tcttctggta tgtgcaatac c                     51

<210> SEQ ID NO 180
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
tacaggaagc ctcagcagcc cagtctgtga cccagcttga c                                41

<210> SEQ ID NO 181
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
tacaggaagc ctcagcaacc cagtcggtga cccagcttg                                   39

<210> SEQ ID NO 182
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
tacaggaagc ctcagcagga gattcagtgg tccagacaga aggc                             44

<210> SEQ ID NO 183
<211> LENGTH: 43
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 183
tacaggaagc ctcagcagga aattcagtga cccagatgga agg           43

<210> SEQ ID NO 184
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
tacaggaagc ctcagcagga gattcagtga cccagatgga agg           43

<210> SEQ ID NO 185
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
tacaggaagc ctcagcaaaa aaccaagtgg agcagagtcc tcagtc        46

<210> SEQ ID NO 186
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
tacaggaagc ctcagcacta catacactgg agcagagtcc ttcattcc      48

<210> SEQ ID NO 187
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
tacaggaagc ctcagcacgg aaggaggtgg agcaggatcc              40

<210> SEQ ID NO 188
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
tacaggaagc ctcagcacag aaggaggtgg agcagaattc tgg           43

<210> SEQ ID NO 189
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
```
tacaggaagc ctcagcagga cccctcagtg ttccagaggg                              40

<210> SEQ ID NO 190
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
tacaggaagc ctcagcacag aaggaggtgg agcaggatcc tg                           42

<210> SEQ ID NO 191
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191
tacaggaagc ctcagcagga gagaatgtgg agcagcatcc ttc                          43

<210> SEQ ID NO 192
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192
tacaggaagc ctcagcagga gagagtgtgg ggctgcatct tc                           42

<210> SEQ ID NO 193
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193
tacaggaagc ctcagcagcc cagaagataa ctcaaaccca accag                        45

<210> SEQ ID NO 194
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194
tacaggaagc ctcagcacag aagataactc aaacccaacc aggaatg                      47

<210> SEQ ID NO 195
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 195
tacaggaagc ctcagcagcc cagagagtga ctcagcccga                        40

<210> SEQ ID NO 196
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196
tacaggaagc ctcagcaagt caacagggag aagaggatcc tcagg                  45

<210> SEQ ID NO 197
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 197
tacaggaagc ctcagcagga gactcggtta cccagacaga agg                    43

<210> SEQ ID NO 198
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 198
tacaggaagc ctcagcagct cagaaggtaa ctcaagcgca gactg                  45

<210> SEQ ID NO 199
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 199
tacaggaagc ctcagcagaa gaccaggtga cgcagagtcc c                      41

<210> SEQ ID NO 200
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 200
tacaggaagc ctcagcaaaa caggaggtga cgcagattcc tgc                    43

<210> SEQ ID NO 201
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201
tacaggaagc ctcagcagga atacaagtgg agcagagtcc tcag                   45

```
<210> SEQ ID NO 202
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202
tacaggaagc ctcagcacag cagcaggtga aacaaagtcc tca                    43

<210> SEQ ID NO 203
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 203
tacaggaagc ctcagcacag caggtgaaac aaagtcctca atctttg                47

<210> SEQ ID NO 204
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 204
tacaggaagc ctcagcaata ctgaacgtgg aacaaagtcc tcagtcac               48

<210> SEQ ID NO 205
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 205
tacaggaagc ctcagcagga caacaggtaa tgcaaattcc tcagtacc               48

<210> SEQ ID NO 206
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 206
tacaggaagc ctcagcagat gctaagacca cccagccccc                        40

<210> SEQ ID NO 207
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 207
tacaggaagc ctcagcagat gctaagacca cccagcccac c                      41
```

<210> SEQ ID NO 208
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 208
tacaggaagc ctcagcagat gctaagacca cacagccaaa ttcaatg                47

<210> SEQ ID NO 209
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 209
tacaggaagc ctcagcaacc cagctgctgg agcagagcc                         39

<210> SEQ ID NO 210
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 210
tacaggaagc ctcagcagac cagcaagtta agcaaaattc accatc                 46

<210> SEQ ID NO 211
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 211
tacaggaagc ctcagcacaa caaccagtgc agagtcctca agc                    43

<210> SEQ ID NO 212
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 212
tacaggaagc ctcagcaagc caagaactgg agcagagtcc tcag                   44

<210> SEQ ID NO 213
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 213
tacaggaagc ctcagcaggt caacagctga atcagagtcc tcaatc                 46

-continued

<210> SEQ ID NO 214
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 214
tacaggaagc ctcagcagaa gacaaggtgg tacaaagccc tctatctc                    48

<210> SEQ ID NO 215
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 215
tacaggaagc ctcagcagaa gacaaggtgg tacaaagccc tcaatc                      46

<210> SEQ ID NO 216
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 216
tacaggaagc ctcagcagcc cagacagtca ctcagtctca accag                       45

<210> SEQ ID NO 217
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 217
tacaggaagc ctcagcagcc cagacagtca ctcagtccca gc                          42

<210> SEQ ID NO 218
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 218
tacaggaagc ctcagcagct cagacagtca ctcagtctca accagag                     47

<210> SEQ ID NO 219
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 219
tacaggaagc ctcagcagag ctgaaagtgg aacaaaaccc tctgttc                     47

<210> SEQ ID NO 220

-continued

```
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 220
tacaggaagc ctcagcaagc aattcagtca agcagacggg c                          41

<210> SEQ ID NO 221
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 221
tacaggaagc ctcagcaaaa aatgaagtgg agcagagtcc tcagaac                    47

<210> SEQ ID NO 222
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 222
caggagggct cggcagatac tggaattacc cagacaccaa aatacctg                   48

<210> SEQ ID NO 223
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 223
caggagggct cggcagaacc tgaagtcacc cagactccca g                          41

<210> SEQ ID NO 224
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 224
caggagggct cggcagacac agctgtttcc cagactccaa aatac                      45

<210> SEQ ID NO 225
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 225
caggagggct cggcagacac agccgtttcc cagactcca                             39

<210> SEQ ID NO 226
<211> LENGTH: 45
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 226
caggagggct cggcagacac tgaagttacc cagacaccaa aacac              45

<210> SEQ ID NO 227
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 227
caggagggct cggcacacct ggtcatggga atgacaaata agaag              45

<210> SEQ ID NO 228
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 228
caggagggct cggcagaaac gggagttacg cagacaccaa g                  41

<210> SEQ ID NO 229
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 229
caggagggct cggcaaagaa gtctttgaaa tgtgaacaac atctggg            47

<210> SEQ ID NO 230
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 230
caggagggct cggcaaaggc tggagtcact caaactccaa gatatc             46

<210> SEQ ID NO 231
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 231
caggagggct cggcaagggc tggggtcact caaactcc                      38

<210> SEQ ID NO 232
<211> LENGTH: 39
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 232
caggagggct cggcagaggc tggagtcacc caaagtccc                                39

<210> SEQ ID NO 233
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 233
caggagggct cggcagagac tggagtcacc caaagtccca c                             41

<210> SEQ ID NO 234
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 234
caggagggct cggcacagca agtgacactg agatgctctt ctcag                         45

<210> SEQ ID NO 235
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 235
caggagggct cggcaactgt gtcctggtac aacaggccc t                              41

<210> SEQ ID NO 236
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 236
caggagggct cggcagacgc tggagtcacc caaagtcc                                 38

<210> SEQ ID NO 237
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 237
caggagggct cggcagaggc tggagtcaca caaagtccca c                             41

<210> SEQ ID NO 238
<211> LENGTH: 40
<212> TYPE: DNA
<213> ORGANISM: Artificial Sequence
```

<220> FEATURE:
<223> OTHER INFORMATION: Description of Artificial Sequence: Synthetic
       primer

<400> SEQUENCE: 238
caggagggct cggcaaggac agcaagcgac tctgagatgc                           40

<210> SEQ ID NO 239
<211> LENGTH: 39
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 239
caggagggct cggcaaatgc tggtgtcact cagacccca                            39

<210> SEQ ID NO 240
<211> LENGTH: 37
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 240
caggagggct cggcaattgc tgggatcacc caggcac                              37

<210> SEQ ID NO 241
<211> LENGTH: 37
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 241
caggagggct cggcaactgc tgggatcacc caggcac                              37

<210> SEQ ID NO 242
<211> LENGTH: 39
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 242
caggagggct cggcaggtgc tggagtctcc cagtccctg                            39

<210> SEQ ID NO 243
<211> LENGTH: 38
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 243
caggagggct cggcaggagc tggagtctcc cagtcccc                             38

<210> SEQ ID NO 244
<211> LENGTH: 38
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 244
caggagggct cggcaggagc tggagtttcc cagtcccc                                 38

<210> SEQ ID NO 245
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 245
caggagggct cggcaggtgc tggagtctcc cagaccc                                  37

<210> SEQ ID NO 246
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 246
caggagggct cggcatggga gctcaggtgt gatccaattt c                             41

<210> SEQ ID NO 247
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 247
caggagggct cggcaggtgc tggagtctcc cagtccc                                  37

<210> SEQ ID NO 248
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 248
caggagggct cggcaggtgc tggagtctcc cagtctccc                                39

<210> SEQ ID NO 249
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 249
caggagggct cggcagatac tggagtctcc cagaacccca g                             41

<210> SEQ ID NO 250
<211> LENGTH: 41
<212> TYPE: DNA
<213> ORGANISM: Artificial Sequence
<220> FEATURE:
<223> OTHER INFORMATION: Description of Artificial Sequence: Synthetic
```

```
primer

<400> SEQUENCE: 250
caggagggct cggcagatac tggagtctcc caggacccca g                 41

<210> SEQ ID NO 251
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 251
caggagggct cggcaatatc tggagtctcc cacaacccca gac               43

<210> SEQ ID NO 252
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 252
caggagggct cggcacacaa ccgcctttat tggtaccgac ag                42

<210> SEQ ID NO 253
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 253
caggagggct cggcagattc tggagtcaca caaaccccaa agc               43

<210> SEQ ID NO 254
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 254
caggagggct cggcagatgc tgaaatcacc cagagcccaa g                 41

<210> SEQ ID NO 255
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 255
caggagggct cggcagatgc tggaatcacc cagagccca                    39

<210> SEQ ID NO 256
<211> LENGTH: 41
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 256
caggagggct cggcaaaggc aggtgaccttt gatgtgtcac c                41

<210> SEQ ID NO 257
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 257
caggagggct cggcagaagc tgaagttgcc cagtcccc                    38

<210> SEQ ID NO 258
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 258
caggagggct cggcagaagc tggagttgcc cagtctccca g                41

<210> SEQ ID NO 259
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 259
caggagggct cggcagaagc tggagtggtt cagtctccca ga               42

<210> SEQ ID NO 260
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 260
caggagggct cggcaggtct cccagatata agattataga gaagaaacag c      51

<210> SEQ ID NO 261
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 261
caggagggct cggcagatgc tggtgttatc cagtcaccca gg               42

<210> SEQ ID NO 262
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 262
caggagggct cggcagatgc tggcattatc cagtcaccca ag                    42

<210> SEQ ID NO 263
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 263
caggagggct cggcagatgc tggagttatc cagtcacccc                       40

<210> SEQ ID NO 264
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 264
caggagggct cggcagatgc tagagtcacc cagacaccaa gg                    42

<210> SEQ ID NO 265
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 265
caggagggct cggcagctgc tggagtcatc cagtcccc                         38

<210> SEQ ID NO 266
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 266
caggagggct cggcagaagc tggagttact cagttcccca gc                    42

<210> SEQ ID NO 267
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 267
caggagggct cggcagatgc catggtcatc cagaacccaa g                     41

<210> SEQ ID NO 268
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 268
```
caggagggct cggcaggtga agaagtcgcc cagactcca                          39

<210> SEQ ID NO 269
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 269
caggagggct cggcagagcc tggagtcagc cagaccc                            37

<210> SEQ ID NO 270
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 270
caggagggct cggcaaatgc cggcgtcatg cagaac                             36

<210> SEQ ID NO 271
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 271
caggagggct cggcagatgg tggaatcact cagtccccaa ag                      42

<210> SEQ ID NO 272
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 272
caggagggct cggcaggtgc tgtcgtctct caacatccga g                       41

<210> SEQ ID NO 273
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 273
caggagggct cggcaagtgc tgtcgtctct caacatccga g                       41

<210> SEQ ID NO 274
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 274
caggagggct cggcagacac caaggtcacc cagagaccta gac                43

<210> SEQ ID NO 275
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 275
caggagggct cggcagacac caaggtcacc cagagaccta gatttc              46

<210> SEQ ID NO 276
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 276
caggagggct cggcacatgc caaagtcaca cagactccag g                   41

<210> SEQ ID NO 277
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 277
caggagggct cggcagatgc tgatgttacc cagaccccaa g                   41

<210> SEQ ID NO 278
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 278
caggagggct cggcagaagc tgacatctac cagaccccaa gatac               45

<210> SEQ ID NO 279
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 279
caggagggct cggcagatgc tgtagttaca caattcccaa gacacag             47

<210> SEQ ID NO 280
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 280
caggagggct cggcagatgc tgtagttaca caattctcaa gacacagaat c        51

```
<210> SEQ ID NO 281
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 281
caggagggct cggcagaagc ccaagtgacc cagaaccc                          38

<210> SEQ ID NO 282
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 282
caggagggct cggcagatgt gaaagtaacc cagagctcga gatatc                 46

<210> SEQ ID NO 283
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 283
caggagggct cggcaagtgc tgtcatctct caaaagccaa gc                     42

<210> SEQ ID NO 284
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 284
caggagggct cggcaacgat ccagtgtcaa gtcgatagcc aag                    43

<210> SEQ ID NO 285
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 285
caggagggct cggcatctca gactattcat caatggccag cg                     42

<210> SEQ ID NO 286
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 286
caggagggct cggcaactat tcatcaatgg ccagcgaccc                        40
```

<210> SEQ ID NO 287
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 287
aaaaaaaaag tgatgagttt caaatcagtc aagagaactc gttcactata actgaatcct    60
cgggatgcct a                                                         71

<210> SEQ ID NO 288
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 288
aaaaaaaaag tgatgagttt caaatcagtc aagagaactt acgagtgtaa actgaatcct    60
cgggatgcct a                                                         71

<210> SEQ ID NO 289
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 289
aaaaaaaaag tgatgagttt caaatcagtc aagagaatgt ctctaagtga actgaatcct    60
cgggatgcct a                                                         71

<210> SEQ ID NO 290
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 290
aaaaaaaaag tgatgagttt caagtattcg tcatcaactc gttcactata actgaatcct    60
cgggatgcct a                                                         71

<210> SEQ ID NO 291
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 291
aaaaaaaaag tgatgagttt caagtattcg tcatcaactt acgagtgtaa actgaatcct    60
cgggatgcct a                                                         71

<210> SEQ ID NO 292
<211> LENGTH: 71
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 292
aaaaaaaaag tgatgagttt caagtattcg tcatcaatgt ctctaagtga actgaatcct      60
cgggatgcct a                                                          71

<210> SEQ ID NO 293
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 293
aaaaaaaaag tgatgagttt caagtcagat agttcaactc gttcactata actgaatcct      60
cgggatgcct a                                                          71

<210> SEQ ID NO 294
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 294
aaaaaaaaag tgatgagttt caagtcagat agttcaactt acgagtgtaa actgaatcct      60
cgggatgcct a                                                          71

<210> SEQ ID NO 295
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 295
aaaaaaaaag tgatgagttt caagtcagat agttcaatgt ctctaagtga actgaatcct      60
cgggatgcct a                                                          71

<210> SEQ ID NO 296
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 296
aaaaaaaaac tatgtcgata caaatcagtc aagagaactc gttcactata actgaatcct      60
cgggatgcct a                                                          71

<210> SEQ ID NO 297
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 297
aaaaaaaaac tatgtcgata caaatcagtc aagagaactt acgagtgtaa actgaatcct        60
cgggatgcct a        71

<210> SEQ ID NO 298
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 298
aaaaaaaaac tatgtcgata caaatcagtc aagagaatgt ctctaagtga actgaatcct        60
cgggatgcct a        71

<210> SEQ ID NO 299
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 299
aaaaaaaaac tatgtcgata caagtattcg tcatcaactc gttcactata actgaatcct        60
cgggatgcct a        71

<210> SEQ ID NO 300
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 300
aaaaaaaaac tatgtcgata caagtattcg tcatcaactt acgagtgtaa actgaatcct        60
cgggatgcct a        71

<210> SEQ ID NO 301
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 301
aaaaaaaaac tatgtcgata caagtattcg tcatcaatgt ctctaagtga actgaatcct        60
cgggatgcct a        71

<210> SEQ ID NO 302
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 302
aaaaaaaaac tatgtcgata caagtcagat agttcaactc gttcactata actgaatcct        60

```
cgggatgcct a                                                          71

<210> SEQ ID NO 303
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 303
aaaaaaaaac tatgtcgata caagtcagat agttcaactt acgagtgtaa actgaatcct    60
cgggatgcct a                                                          71

<210> SEQ ID NO 304
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 304
aaaaaaaaac tatgtcgata caagtcagat agttcaatgt ctctaagtga actgaatcct    60
cgggatgcct a                                                          71

<210> SEQ ID NO 305
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 305
aaaaaaaaat acatccaaga caaatcagtc aagagaactc gttcactata actgaatcct    60
cgggatgcct a                                                          71

<210> SEQ ID NO 306
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 306
aaaaaaaaat acatccaaga caaatcagtc aagagaactt acgagtgtaa actgaatcct    60
cgggatgcct a                                                          71

<210> SEQ ID NO 307
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 307
aaaaaaaaat acatccaaga caaatcagtc aagagaatgt ctctaagtga actgaatcct    60
cgggatgcct a                                                          71
```

-continued

```
<210> SEQ ID NO 308
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 308
aaaaaaaaat acatccaaga caagtattcg tcatcaactc gttcactata actgaatcct    60
cgggatgcct a                                                         71

<210> SEQ ID NO 309
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 309
aaaaaaaaat acatccaaga caagtattcg tcatcaactt acgagtgtaa actgaatcct    60
cgggatgcct a                                                         71

<210> SEQ ID NO 310
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 310
aaaaaaaaat acatccaaga caagtattcg tcatcaatgt ctctaagtga actgaatcct    60
cgggatgcct a                                                         71

<210> SEQ ID NO 311
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 311
aaaaaaaaat acatccaaga caagtcagat agttcaactc gttcactata actgaatcct    60
cgggatgcct a                                                         71

<210> SEQ ID NO 312
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 312
aaaaaaaaat acatccaaga caagtcagat agttcaactt acgagtgtaa actgaatcct    60
cgggatgcct a                                                         71

<210> SEQ ID NO 313
<211> LENGTH: 71
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 313
aaaaaaaaat acatccaaga caagtcagat agttcaatgt ctctaagtga actgaatcct    60
cgggatgcct a                                                         71

<210> SEQ ID NO 314
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 314
agcacaggga aactcatcac                                                20

<210> SEQ ID NO 315
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 315
gcatcatcgt atcgacatag                                                20

<210> SEQ ID NO 316
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 316
atggttcggt cttggatgta                                                20

<210> SEQ ID NO 317
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 317
cgccaatgct cttgactgat                                                20

<210> SEQ ID NO 318
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 318
aggacttcga tgacgaatac                                                20

<210> SEQ ID NO 319
<211> LENGTH: 20
<212> TYPE: DNA
```

<213> ORGANISM: Artificial Sequence
<220> FEATURE:
<223> OTHER INFORMATION: Description of Artificial Sequence: Synthetic oligonucleotide

<400> SEQUENCE: 319
atccttgcga actatctgac				20

<210> SEQ ID NO 320
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 320
gccgtatcat agtgaacgag				20

<210> SEQ ID NO 321
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 321
ccagcgatta cactcgtaag				20

<210> SEQ ID NO 322
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 322
cagacctgca cttagagaca				20

<210> SEQ ID NO 323
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 323
gtgatgagtt tccctgtgct				20

<210> SEQ ID NO 324
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 324
ctatgtcgat acgatgatgc				20

<210> SEQ ID NO 325
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 325
tacatccaag accgaaccat                                                    20

<210> SEQ ID NO 326
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 326
atcagtcaag agcattggcg                                                    20

<210> SEQ ID NO 327
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 327
gtattcgtca tcgaagtcct                                                    20

<210> SEQ ID NO 328
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 328
gtcagatagt tcgcaaggat                                                    20

<210> SEQ ID NO 329
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 329
ctcgttcact atgatacggc                                                    20

<210> SEQ ID NO 330
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 330
cttacgagtg taatcgctgg                                                    20

<210> SEQ ID NO 331
<211> LENGTH: 20
<212> TYPE: DNA
<213> ORGANISM: Artificial Sequence
<220> FEATURE:

-continued

```
<223> OTHER INFORMATION: Description of Artificial Sequence: Synthetic
      oligonucleotide

<400> SEQUENCE: 331
tgtctctaag tgcaggtctg                                                    20
```

COMPOSITIONS AND METHODS FOR SCREENING T CELLS WITH ANTIGENS FOR SPECIFIC POPULATIONS

CROSS-REFERENCE TO RELATED APPLICATION(S)

The present application claims priority to and the benefit of U.S. Provisional Application Ser. No. 62/169,337 filed on Jun. 1, 2015, entitled "A Method for Pairing the T Cell Receptor Sequence with Cognate Antigen from Diverse Antigen Specific T Cell Populations," the entire content of which is incorporated herein by reference.

STATEMENT REGARDING FEDERALLY SPONSORED RESEARCH OR DEVELOPMENT

This invention was made with government support under Grant No. CA151819 and CA1710689 awarded by the National Institutes of Health. The government has certain rights in the invention.

INCORPORATION BY REFERENCE

The instant application contains a Sequence Listing which has been submitted electronically in ASCII format and is hereby incorporated by reference in its entirety. Said ASCII copy, created on Sep. 14, 2016, is named 122720US_SL.txt and is 65,986 bytes in size.

BACKGROUND

Neoantigens from tumor cells are peptide fragments of mutated proteins that contain a mutation, and are capable of being presented in the cleft of Major Histocompatibility Complex (MHC) Class I molecules on the surfaces of cells within the tumor, where they can be surveyed by CD8-positive T cells. The tumor-specificity of neoantigens, coupled with the ability of neoantigen-specific T cells to specifically kill cancer cells, has made tumor neoantigens increasingly important for cancer immunotherapy. Additionally, T cell receptors (TCRs) that recognize specific neoantigens are candidates for TCR-engineered cell based therapies for targeting infections that produce neoantigens.

Putative neoantigens have been previously identified by tumor exome analysis, and subsequently rank-ordered according to their MHC binding strength using in silico analysis. However, finding which candidate neoantigens are actually promoting T cell tumor infiltration is challenging for several reasons. First, a patient tumor that has a mutation density of 10 per 1 million expressed DNA base pairs might be predicted to have on the order of 50 putative neoantigens that exhibit a binding constant ($K_d$) to a given human leukocyte antigen (HLA) genotype MHC of 500 nM or lower. Furthermore, any particular neoantigen-specific T cell population is likely to exist in very low abundance in a patient, rendering isolation and/or identification of neoantigen-specific T cells very difficult. Related challenges to these issues include the pairing of neoantigens to their cognate TCRs. Nevertheless, these neoantigen-T cell pairing interactions are at the core of cancer immunotherapy, and so there has been significant effort towards meeting these challenges. Previous approaches for neoantigen-specific T cell pairing have shown to be laborious, non-quantitative, and/or they may only identify one or two T cell populations per HLA genotype due to limited sensitivity.

SUMMARY

In some embodiments of the present invention, an antigen complex includes a nanoparticle sorting agent including a nanoparticle, a polynucleotide detection tag having at least one coding region, the polynucleotide detection tag being conjugated to the nanoparticle, and a first polynucleotide hybridization domain conjugated to the polynucleotide detection tag. The antigen complex also includes a peptide-loaded streptavidin major histocompatability complex (MHC) tetramer, including a modified streptavidin protein, four biotin-modified MHC proteins each independently conjugated to the modified streptavidin protein, an antigen peptide bound to the biotin-modified MHC proteins, and a second polynucleotide hybridization domain different from the first polynucleotide hybridization domain and conjugated to the modified streptavidin protein, where the nanoparticle sorting agent is linked to the peptide-loaded streptavidin MHC tetramer by hybridization of the first polynucleotide hybridization domain to the second polynucleotide hybridization domain.

In some embodiments of the present invention, a library of antigen complexes include a plurality of the antigen complexes disclosed above where each of the antigen complexes has a different antigen peptide and different polynucleotide detection tag than any other of the antigen complexes in the plurality of antigen complexes.

In some embodiments of the present invention, a kit for detecting neoantigen-specific T cells includes a polynucleotide detection tag including at least one coding region, where the polynucleotide detection tag is conjugated to a nanoparticle, the kit also includes a decoding polynucleotide that is capable of hybridizing to the at least one coding region of the polynucleotide detection tag. In some embodiments, the kit also includes a displacement polynucleotide capable of hybridizing to the decoding polynucleotide. In some embodiments, the kit includes at least one of the polynucleotide detection tag sequences of FIG. 4. In some embodiments, the kit includes at least one of the decoding polynucleotide sequences of FIG. 8A. In some embodiments, the kit includes at least one of the displacement polynucleotide sequences of FIG. 8B. In some embodiments, the kit also includes at least one peptide-loaded streptavidin major histocompatability complex (MHC) tetramer, including a modified streptavidin protein, four biotin-modified MHC proteins each independently conjugated to the modified streptavidin protein, and an antigen peptide bound to the biotin-modified MHC proteins.

In some embodiments of the present invention, a method for isolating neo-antigen-specific T cells for a tumor in a subject includes identifying candidate T cell epitopes for the tumor using a major histocompatiblity complex (MHC) binding algorithm, synthesizing antigen peptides corresponding to the candidate T cell epitopes, preparing the library of antigen complexes using the antigen peptides, incubating the library of antigen complexes with TILs or PBMCs from the subject, and separating paired T cells from unpaired T cells, the paired T cells comprising those T cells that have paired with any of the antigen peptides of any of the antigen complexes in the library of antigen complexes.

In some embodiments of the present invention, the method for isolating neo-antigen-specific T cells for a tumor in a subject as above, also includes adding the paired T cells to a microfluidic device to separate the paired T cells into individual paired T cells, and detecting the sequence of the at least one coding region of the polynucleotide detection tag of the antigen complex of each individual paired T cell. In some embodiments, the detecting the sequence of the at least one coding region of the polynucleotide detection tag of the antigen complex of each individual paired T cell includes incubating the polynucleotide detection tag of each individual paired T cell with at least two labeled decoding polynucleotides, and detecting presence of a hybridized labeled decoding polynucleotide to thereby determine the sequence of the at least one coding region of the polynucleotide detection tag.

In some embodiments of the present invention, the method for isolating neo-antigen-specific T cells for a tumor in a subject is as above, in which the least one coding region of the polynucleotide detection tag of the antigen complex includes at least two coding regions, and detecting the sequence of the at least two coding regions of the polynucleotide detection tag of the antigen complex of each individual paired T cell includes incubating the polynucleotide detection tag of each individual paired T cell with at least two first labeled decoding polynucleotides, detecting presence of one or more first hybridized labeled decoding polynucleotides to thereby determine the sequence of a first one of the at least two coding regions of the polynucleotide detection tag, incubating the one or more first hybridized labeled decoding polynucleotides with one or more displacement polynucleotides to remove the first hybridized labeled decoding polynucleotides from the first hybridized labeled decoding polynucleotide to yield a partially decoded polynucleotide detection tag, incubating the partially decoded polynucleotide detection tag with one or more second labeled decoding polynucleotides, and detecting presence of a second hybridized labeled decoding polynucleotide to thereby determine the sequence of a second one of the at least two coding regions of the polynucleotide detection tag of the antigen complex of each individual paired T cell.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 4 is a table listing examples of 3-position DNA barcode (polynucleotide detection tag) (red, green, or yellow) sequences (SEQ ID NOS 287-313, respectively, in order of appearance) for preparing a library of barcoded NP-antigen-MHC complexes for identification of antigen-specific T cells, according to embodiments of the present invention.

FIG. 5B is an antigen barcode key showing the corresponding readout for each antigen with the corresponding coding region sequence (D1, D2, D3, D5, D6, D7, D9, D10, or D11) identified along with the corresponding fluorescent dye for the decoding sequence (red, yellow or green), according to embodiments of the present invention.

FIG. 8A is a list of fluorescent dye labeled DNA (polynucleotide decoding sequences) (M1 (SEQ ID NO: 314), M2 (SEQ ID NO: 315), M3 (SEQ ID NO: 316), M5 (SEQ ID NO: 317), M6 (SEQ ID NO: 318), M7 (SEQ ID NO: 319), M9 (SEQ ID NO: 320), M10 (SEQ ID NO: 321), and M11 (SEQ ID NO: 322)) with the sequence shown in the color of the attached dye (red, yellow, or green) for decoding each of the coding regions of FIG. 4 and FIG. 5B, according to embodiments of the present invention.

FIG. 8B is a list of displacement DNA (polynucleotide displacement sequences) (M1 comp (SEQ ID NO: 323), M2 comp (SEQ ID NO: 324), M3 comp (SEQ ID NO: 325), M5 comp (SEQ ID NO: 326), M6 comp (SEQ ID NO: 327), M7 comp (SEQ ID NO: 328), M9 comp (SEQ ID NO: 329), M10 comp (SEQ ID NO: 330), and M11 comp (SEQ ID NO: 331)) for displacing each the decoding sequences listed in FIG. 9A, according to embodiments of the present invention.

DETAILED DESCRIPTION

Figure 1:
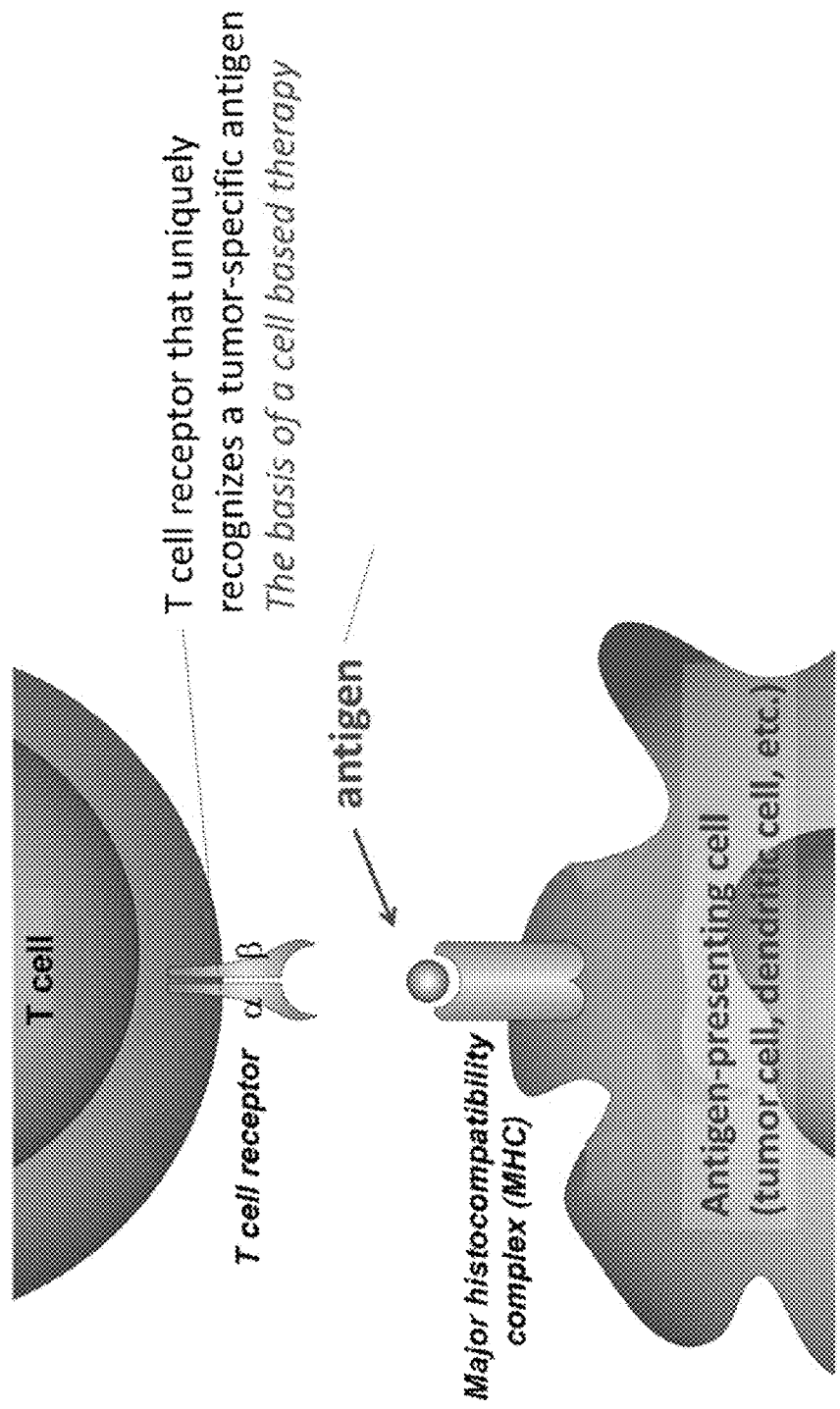
FIG. 1 is a schematic depicting the interaction between a T cell receptor (TCR) on a T cell (shown in blue) and an antigen presented by the Major Histocompatibility Complex (MHC) on an antigen presenting cell (APC) (shown in red) as described by Coulie et al., 2014, *Nat Rev Cancer* 14: 135-146, the entire contents of which are herein incorporated by reference.
Figure 2B:
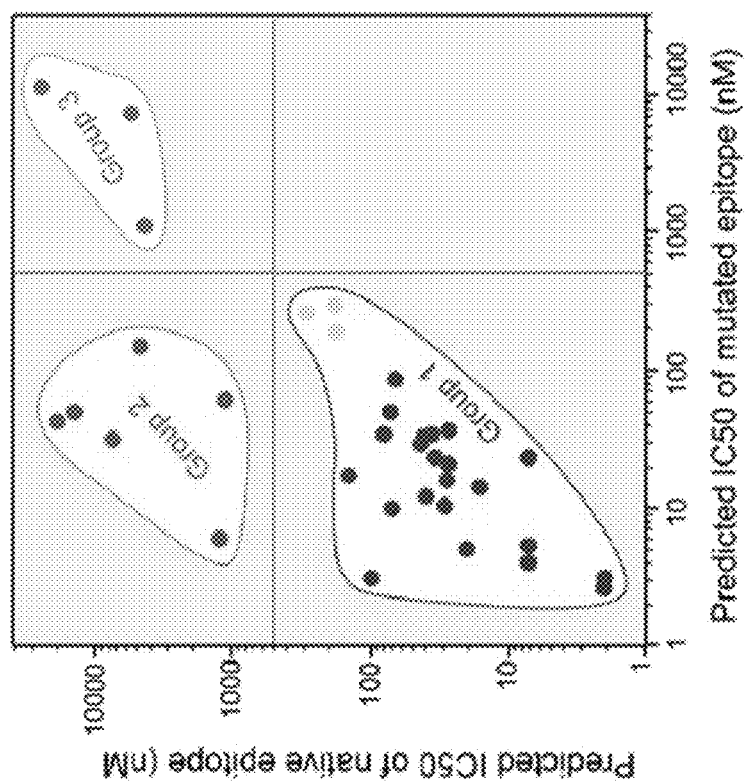
FIGS. 2A-2B show the specific binding interactions between the peptide antigen (yellow) in the MHC molecule (green) interacting with the TCR (purple), and the predicted $IC_{50}$ binding of mutated epitope residues compared to native epitope residues, as described by Fritsch et al., 2014, *Cancer Immunol Res.*, 2:522-529, the entire contents of which are herein incorporated by reference.
Figure 2A:
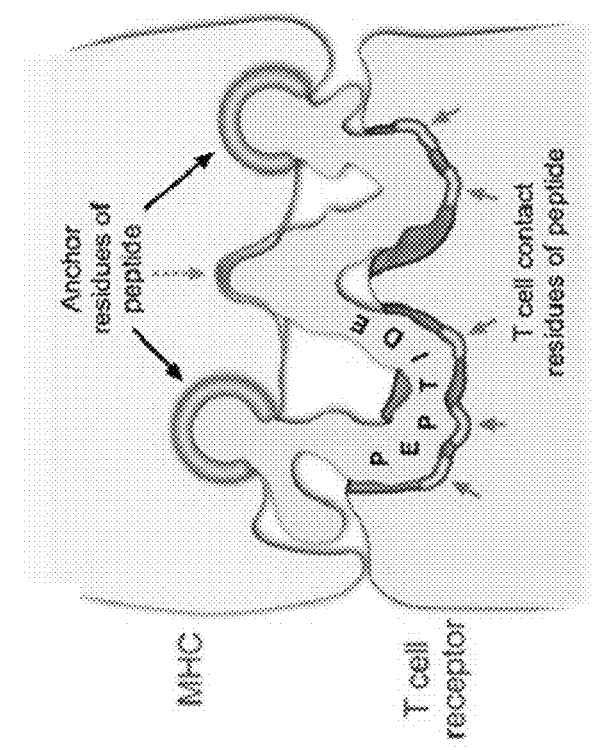

T-cell mediated immunity is characterized by the activation of antigen-specific cytotoxic T cells that are able to induce apoptosis in cells that display epitopes of foreign antigen in a major histocompatibility complex (MHC) on their surface, as depicted in FIG. 1. These cells displaying an MHC complex loaded with foreign antigen include virus-infected cells, cells with intracellular bacteria, and cancer cells displaying tumor antigens. In order to utilize the T-cell mediated immunity process, e.g., for patient-specific cancer immunotherapy, one of the initial steps includes identification of the patient's tumor-specific antigens (i.e., neoantigens). For identification of a patient's putative neoantigens (tumor or pathogen), in silico predictive algorithmic programs are utilized that analyze the tumor, viral, or bacterial sequencing data to identify somatic mutations corresponding to putatively expressed neoantigens. Additionally, human leukocyte antigen (HLA) typing is determined from a tumor or blood sample of the patient, and this HLA information is utilized together with the identified putative neoantigen peptide sequences in a predictive algorithm for MHC binding, as verified by Fritsch et al., 2014, supra, and depicted in FIG. 2A-2B. These in silico analyses result in a ranked list of the patient's candidate neoantigen peptides which can be readily synthesized for screening of cognate antigen-specific T cells. As used herein, "antigen-specific T cells" refer to cells that are distinguished from one another by their T cell receptors (TCRs), which give them their antigen specificity.

Currently known methods for screening neoantigen-specific T cells are time consuming and/or have low sensitivity, and most methods identify only a few T cells per HLA genotype. Embodiments of the present invention include recombinant antigen-loaded MHC compositions and facile decoding methods for high fidelity, rapid, and non-destructive isolation and identification of patient-specific T cell populations targeted to patient-specific antigens, e.g., neoantigens. Embodiments of the present invention include a nanoparticle (NP) having a unique polynucleotide barcode (NP) linked to a unique recombinant antigen-MHC complex. Utilizing the barcoded nanoparticle-antigen-MHC complex, T cells that pair with the antigen-MHC complex are then isolated in this antigen-MHC-T cell complex by selective isolation of the nanoparticle. The isolated antigen-MHC-T cell complex may then be transferred to a cell trapping platform to separate individual antigen-MHC complex-T cells. According to embodiments of the present invention, the unique barcode for each isolated NP is identified by in situ amplification or using fluorescently labeled barcode sense strand "readers". Using this nanoparticle isolation and barcode identification methodology, the individual antigen-MHC-T cell complex is identified, but is not destroyed. Accordingly, the isolated T cell is available after identification as a valuable source for further characterization (e.g., tumor biomarker analysis) or for further propagation. Further growth of the T cell results in an enriched population of patient-derived T cells targeted to the patient-specific antigens. This population of patient-derived T cells targeted to the patient-specific antigens may be used for adoptive cell transfer into the patient as a means of immunotherapy targeting the tumor or pathogen.

Figure 3A:
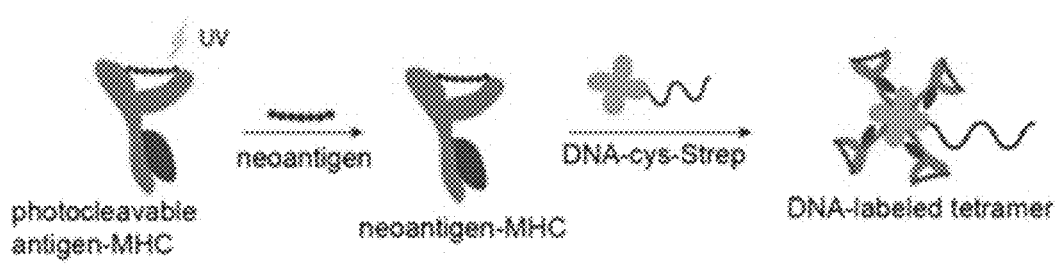
FIG. 3A is a schematic showing construction of a conditional antigen MHC molecule (green and purple) for loading different candidate antigen peptides using DNA-labeled (black) and cysteine-modified streptavidin (brown) bound by four biotin-MHC molecules to form a library of DNA-labeled antigen-MHC complexes, according to embodiments of the present invention.
Figure 3B:
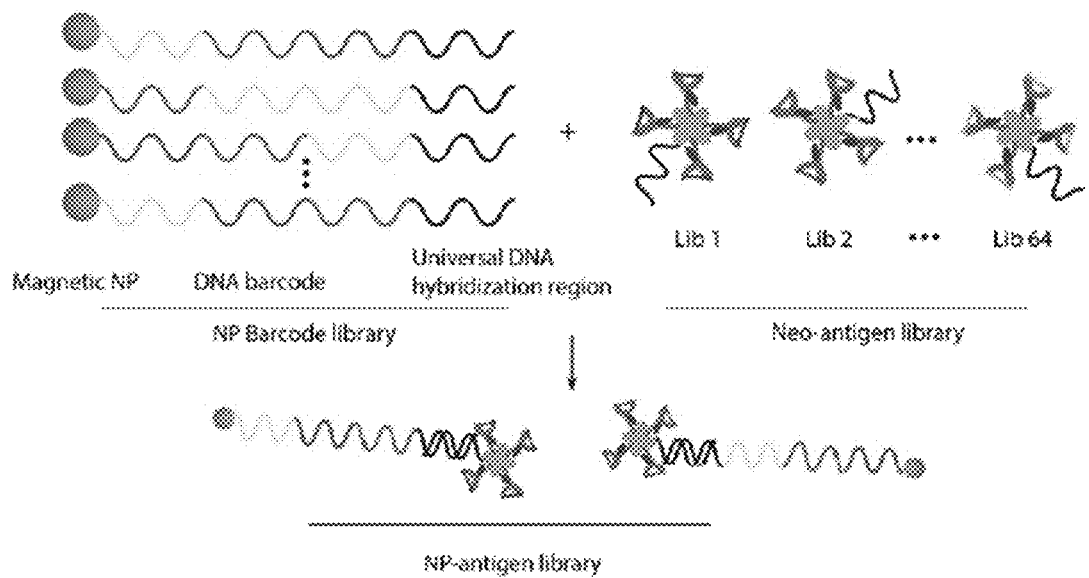
FIG. 3B is a schematic showing the assembly and linking of DNA barcoded nanoparticles (NP) with DNA-labeled antigen-MHC complexes to form a library of barcoded NP-antigen-MHC complexes, in which the DNA barcode (i.e., polynucleotide detection tag) includes three distinct coding regions (red, green, or yellow) attached to the nanoparticle and with a hybridization DNA (black) at the 3' end of the barcode that complexes with the hybridization DNA of the DNA-labeled antigen-MHC complexes to form a barcoded NP-antigen-MHC complex library, according to embodiments of the present invention.
Figure 3C:
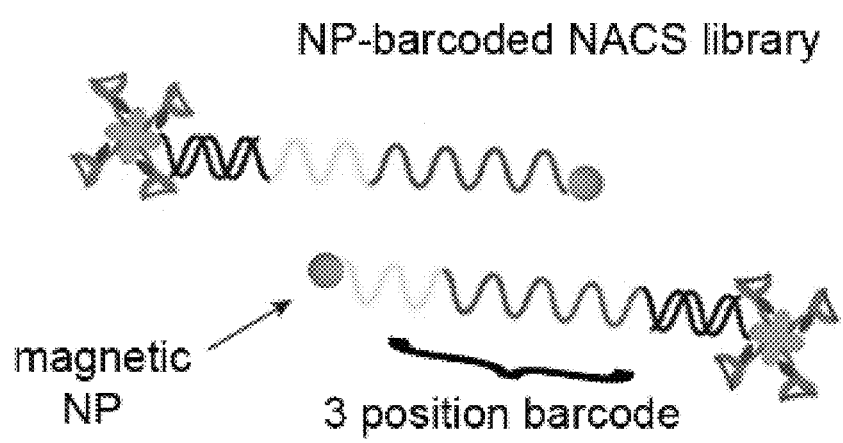
FIG. 3C is a schematic showing an example of a 3-position coding region barcode, (red, green, or yellow) according to embodiments of the present invention.

Compositions according to embodiments of the present invention include a recombinant antigen-MHC complexed with a barcoded nanoparticle (NP) sorting agent to form a barcoded NP-antigen-MHC complex. The barcoded NP-antigen-MHC complex is modular in form as schematically shown in FIGS. 3A and 3B. The barcoded NP-antigen-MHC complex is made of an antigen-MHC complex and a barcoded NP complex linked together by polynucleotide hybridization domains (shown in black in FIG. 3B). The modular form of the barcoded-NP-antigen-MHC complex allows for the barcoded coding regions to be easily modified to add specificity and to increase the number of different complexes that can be assayed together and subsequently isolated and identified. With the barcoded coding region forming a polynucleotide detection tag, each antigen is associated with a unique n-position barcode polynucleotide sequence allowing for n possible sequences per position. An example of a 3-position barcode is shown as different colors (yellow, red, or green) in FIGS. 3B and 3C. This 3-position barcode yields a $3^3$, or 27-plex antigen library with each of the 27 different antigens having a specific barcode that can be readily determined upon isolation of the complex. The ability to screen 27 different antigens with one T cell suspension is a significant advantage over the current more time consuming methods. Each of the modular components of the barcoded NP-antigen-MHC complex is described in more detail below.

In silico analysis can be used to identify neoantigens. The in silico analysis for identifying putative neoantigens requires the genomic (DNA) or exomic (RNA) sequence of the tumor, virus, or bacteria in the patient. As the majority of viruses and bacteria found in patients are not unique to one patient, the genome sequences of these pathogens may be known and the available sequence data may be used. Nonetheless, both unknown (new) and previously identified viruses and bacteria may be isolated from a patient (e.g., from a blood sample) for DNA or RNA sequencing.

As tumor cancers include patient-specific mutations, DNA or RNA sequencing of tumor cells from a patient's tumor biopsy or blood sample is carried out as an initial step. Using the example of tumor neoantigens, according to embodiments of the present invention, identification of tumor neoantigens specific to a patient includes DNA and/or RNA sequencing as well as HLA-typing of tumor cells from a tumor biopsy or a blood sample of the patient. For somatic mutation identification (i.e., somatic mutation calling), DNA or RNA sequencing is also performed on a matched normal patient tumor or blood sample. The collective tumor-normal sequencing data are then input into at least one (e.g., two or three) algorithmic program (e.g., MuTect v1.1.7, Varscan2 Somatic (V2.3.6), and/or the GATK-HaplotypeCaller (HC, v3.3)) to identify somatic mutations that putatively express (correspond to) neoantigens. In some embodiments of the present invention, for patients having a tumor with low mutation burden, all of the in silico identified somatic mutations may be utilized to form a set of candidate tumor neoantigens for T cell screening. Alternatively, while all identified somatic mutations may be assayed, numerous somatic mutations may be identified in patients having a tumor with a high mutation burden, and therefore, it may not be efficient or necessarily effective to screen all of the identified mutations. Accordingly, in some embodiments of the present invention, the somatic mutations identified in silico are ranked with the highest ranked somatic mutations being observed by at least three algorithmic programs, followed by at least 2 algorithmic programs. In order to screen a manageable number of candidate neoantigen peptides, the patient's HLA type is determined from the tumor exome sequencing data using software for HLA typing (e.g., ATHLATES). Using software (e.g., the NetMHC3.4 server) for the patient-specific HLA type, putative neoantigenic sequences from the patent's biopsied tumor or blood sample are identified.

Embodiments of the present invention include a recombinant antigen-MHC complex that is capable of pairing with cognate T cells. As used herein, "antigen complex," "antigen-MHC," "antigen-MHC complex," "recombinant antigen-MHC complex," "peptide MHC," and "p/MHC," are used interchangeably to refer to a recombinant major histocompatibility complex with a peptide in the antigen binding groove. As used herein, "antigen" includes any antigen including patient-specific neoantigens.

A recombinant antigen-MHC complex according to embodiments of the present invention includes a recombinant MHC molecule. In some embodiments of the present invention, the MHC complex may be an MHC Class I (MHC I) complex that pairs with CD8-positive (CD8+) T "killer" cells. In other embodiments of the present invention, the MHC complex may be an MHC Class II (MHC II) complex that pairs with CD4+ "helper" T cells. The antigens presented by MHC Class I complexes are cytosolic proteins, while antigens presented by MHC Class II complexes are derived from extracellular proteins. As tumor cells are endogenously derived cells expressing mutations, tumor antigens are commonly presented by MHC Class I molecules, thereby pairing with CD8+ T cells. Similarly, viral proteins are endogenously expressed from a patient's cells, and are also presented by MHC Class I molecules to CD8+ T cells. Bacterial cells, however, express proteins using their own cellular machinery, which upon infection in a patient, are considered exogenously expressed and are presented by the patient's MHC Class II molecules to CD4+ T helper cells. MHC class III molecules include other immune components, such as complement components (e.g., C2, C4, factor B) and some that encode cytokines (e.g., TNF-a) and also heat shock proteins (hsps).

According to embodiments of the present invention, the MHC I or MHC II molecule of the recombinant antigen MHC complex is synthesized to correspond to the patient's HLA type. Polymorphisms are found in both MHC I and MHC II molecules. The MHC Class I molecules are heterodimers made of two polypeptide chains, α and β2-microglobulin (b2m). The α chain has three domains including α1, α2, and α3. The α and b2m chains are linked noncovalently via interaction of b2m and the α3 domain of the α chain. The α chain is polymorphic and is encoded by the HLA gene complex while the b2m subunit is not polymorphic and is encoded by the b2m gene. Assembly of the a and b2m chains is stabilized by the presence of a 9-11 amino acid peptide antigen loaded in the antigen binding groove on the surface of the α1 and α2 domains. According to embodiments of the present invention, patient-specific MHC class I antigens are presented on recombinant MHC class I complexes corresponding to the patient's HLA type. For example, the MHC I a chain is encoded by the HLA-A, HLA-B, or HLA-C gene. Each of the HLA-A, HLA-B, and HLA-C genes express allele-specific subtypes some of which are shown in Table 7 in Example 19.

The MHC Class II molecules are heterodimers made of two polypeptide chains, α and β. The α and b chains each have two domains: α1 and α2, and β1 and β2, respectively. Both the α and β chains are polymorphic and are encoded by the HLA gene complex. Assembly of the a and β chains forms an antigen binding groove on the surface of both the α1 and β2 domains with antigen peptide lengths from 11 to 30 amino acids. According to embodiments of the present invention, patient-specific MHC class II antigens are presented on recombinant MHC class II complexes corresponding to the patient's HLA type. For example, the HLA genes include HLA-DM, HLA-DO, HLA-DQ, and HLA in which the MHC II a chain is encoded by the HLA-A-DMA, HLA-DOA, HLA-DPA1, HLA-DQA2, or HLA-DRA gene and the β chain is encoded by HLA-DMB, HLA-DOB, HLA-DPB1, HLA-DQB1, HLA-DQB2, HLA-DRB1, HLA-DRB3, HLA-DRB4, or HLA-DRB5 gene.

In some embodiments of the present invention, the recombinant MHC molecule is an MHC Class II molecule expressed and loaded with a candidate antigen peptide as described in Novak et al., 1999, *J. Clin. Invest.* 104:R63-R67, the entire contents of which are herein incorporated by reference.

In some embodiments of the present invention, the recombinant MHC molecule is an MHC Class I molecule expressed as a conditional ligand. As the MHC class I molecule is unstable in the absence of peptide (i.e. antigen peptide), a recombinant MHC Class I molecule is expressed with a peptide having a cleavable moiety, that upon irradiation with UV light dissociates from the complex and disintegrates. However, if the UV disintegration of the cleavable peptide is performed in the presence of a "rescue peptide," the rescue peptide will readily replace the UV irradiated peptide in the binding groove, as depicted in FIG. 3A and described in Toebes et al., 2006, *Nat. Med.* 12:246-251 and Bakker et al., *PNAS*, 2008, 105:3825-3830, the entire contents of both of which are herein incorporated by reference. Using this technology, several assembled MHC Class I molecules can be easily loaded with candidate neoantigens to form a MHC class I neoantigen library for screening T cells.

In some embodiments of the present invention, the recombinant MHC molecule is a tetramer complex of four MHC molecules each loaded with the same candidate antigen peptide. Since most neoantigens have low binding affinities ($K_d$) for MHC proteins (e.g., 500 nM or lower) a tetrameric MHC complex allows for increased binding avidity, thereby increasing the sensitivity of this antigen-MHC tetrameric probe for pairing with low abundant cognate T cells. In some embodiments of the present invention, an MHC tetramer is formed using modified streptavidin conjugated with four biotin-modified MHC molecules. The streptavidin is modified to enable binding of a polynucleotide (e.g., DNA or RNA) linker. Modification of the streptavidin includes a binding moiety that can pair with (e.g., covalently bind to) a corresponding cognate binding moiety linked to the polynucleotide molecule. Any suitable pair of binding moieties may be used to modify streptavidin and the polynucleotide for linkage. Non-limiting examples of binding moiety pairs include a thiol group (e.g., cysteine) and maleimide, adamantane and cyclodextrin, an amino group and a carboxy group, and an azido group and alkynl group (i.e., click chemistry). An example of a cysteine-modified streptavidin linked to a maleimide-modified DNA hybridization domain (the "DNA-labeled tetramer") is shown in FIG. 3A.

One of the current challenges with screening multiple antigen-MHC-T cell pairings is the isolation and identification of the T cell receptor epitope corresponding to the paired peptide antigen. Embodiments of the present invention include a modified nanoparticle linked to a polynucleotide detection tag (i.e., the barcode), where the polynucleotide detection tag includes at least one coding region. This complex, as well as the method of using the complex, is also referred to as nanoparticle-barcoded nucleic acid cell sorting (NP-barcoded NACS) and a nanoparticle sorting agent. In some embodiments, the nanoparticle is magnetic for isolation using a magnet. In some embodiments, the nanoparticle is a 1 um to 15 um polystyrene particle isolated by gravity. According to embodiments of the present invention, the nanoparticle is modified with a binding moiety for linking to the polynucleotide coding region. Modification of the nanoparticle includes a binding moiety that can pair with (e.g., covalently bind to) a corresponding cognate binding moiety linked to the polynucleotide molecule. Any suitable pair of binding moieties may be used to modify the nanoparticle and the polynucleotide detection tag for linkage. Non-limiting examples of binding moiety pairs include a thiol group (e.g., cysteine) and maleimide, adamantane and cyclodextrin, an amino group and a carboxy group, and an azido group and alkynl group.

Embodiments of the present invention include a barcoded-nanoparticle complex where the barcode is a polynucleotide detection tag made of coding regions that provide a unique antigen-specific sequence for identification after T cell isolation. As used herein, a "coding region" is a set of nucleotides with a unique and specific sequence that is separate from another polynucleotide. In some embodiments, one polynucleotide coding region is made of 5 to 25 nucleotide basepairs. In some embodiments, one polynucleotide coding region is made of 7 to 25 nucleotide basepairs, 8 to 25 nucleotide basepairs, 9 to 25 nucleotide basepairs, 10 to 25 nucleotide basepairs, 10 to 20 nucleotide basepairs, 10 to 19 nucleotide basepairs, 10 to 18 nucleotide basepairs, 10 to 17 nucleotide basepairs, or 10 to 16 nucleotide basepairs. In some embodiments, the barcoded nanoparticle complex has a polynucleotide detection tag with at least one coding region (i.e., a 1-position barcode). As understood by a person skilled in the art, the number of coding regions (n) corresponds to the number of different antigens that can be screened together and subsequently identified. For analysis of the coding regions in situ, the number of different coding regions is only limited by the number of different colored fluorescent dyes. For decoding of the polynucleotide detection tag, the coding regions will be "read" starting with coding region attached to the nanoparticle which is referred to as the first coding region or coding region 1. Any coding region thereafter in the direction away from the nanoparticle is the second coding region (coding region 2), followed by the third coding region (coding region 3) and so on. An example of a nanoparticle linked to a polynucleotide detection tag having three coding regions with a polynucleotide (e.g., ssDNA) hybridization domain (black) is depicted in FIG. 3B as the "NP Barcode library". In a library of barcoded-NP complexes, according to embodiments of the present invention, each polynucleotide detection tag sequence is unique from all other polynucleotide detection tag sequences. In some embodiments of the present invention, while a coding region sequence may be found in more than one detection tag sequence, each coding region sequence may only occur in one coding region position. For example, a 3-position coding region library of ssDNA includes coding regions D1, D2, and D3 in coding region 1, D5, D6, and D7 in coding region 2, and D9, D10, and D11 in coding region 3, resulting in 27 different detection tag sequences as listed in the table of FIG. 4.

According to embodiments of the present invention, a polynucleotide hybridization domain is linked to the 3' end of the polynucleotide detection tag of the barcoded NP, and a second polynucleotide hybridization domain is linked to the streptavidin scaffold of the antigen-MHC complex. Accordingly, the antigen-MHC complex is linked to a barcoded nanoparticle through hybridization of complementary hybridization domains. In some embodiments of the present invention, the first polynucleotide hybridization domain and the second polynucleotide hybridization domain may be single stranded DNA (ssDNA) having a first and a second hybridization sequence, respectively, where the first and second hybridization sequences are complementary, resulting in a linker of hybridized double stranded DNA (dsDNA), shown as overlapping black lines in FIGS. 3B, 3C. In some embodiments, the first and second hybridization domains are "universal" and are the same for all barcoded NP complexes and antigen-MHC complexes in a library. Using a universal hybridization domain allows for synthesis of one streptavidin molecule with the attached hybridization domain. Additionally, using a universal hybridization domain that encodes a restriction site or a UV cleavable sequence allows for rapid cleavage of the antigen-MHC complex from the NP-barcode. In other embodiments of the present invention, the first and second hybridization domains are different for each barcoded NP-antigen-MHC complex.

Figure 5A:
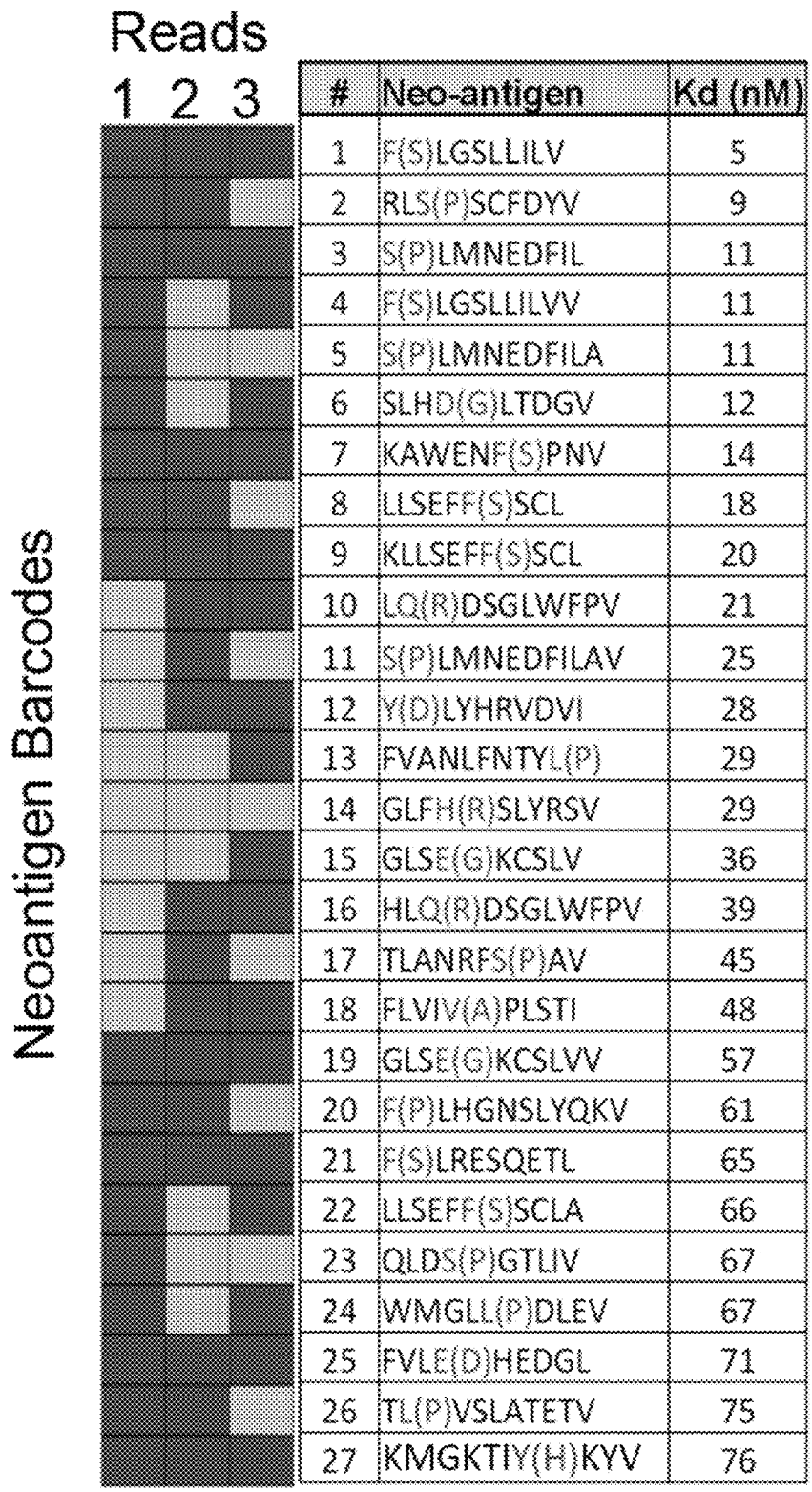
FIG. 5A is an antigen barcode key listing the 27 candidate antigens and corresponding barcode sequences and fluorescent dye color for the decoding sequence (red, yellow, or green) in a barcoded-NP-antigen-MHC complex library, according to embodiments of the present invention. Neo-antigen peptide sequences disclosed as SEQ ID NOS 1-27 and native peptide sequences disclosed as SEQ ID NOS 51-77, all respectively, in order of appearance.
Figure 5B:
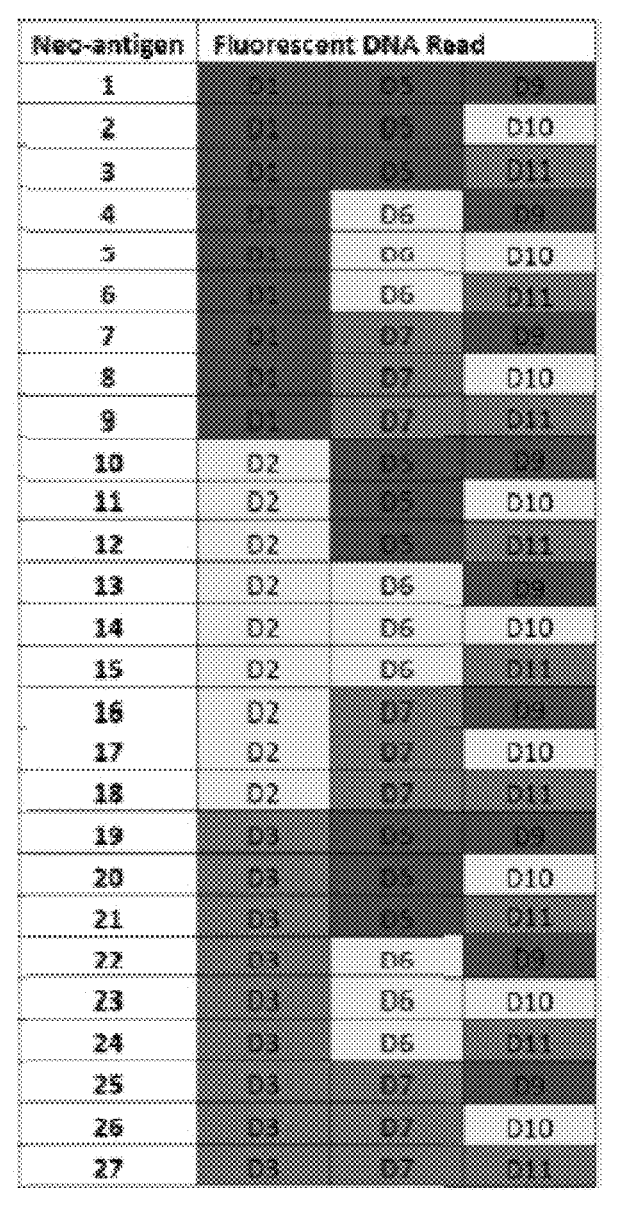

As understood by a person having ordinary skill in the art, each unique antigen-MHC complex is linked (i.e., hybridized) to a unique barcode sequence. In some embodiments of the present invention, the preparation of a barcoded NP-antigen-MHC complex library includes a record (e.g., a key or a legend) of the candidate antigens and their corresponding barcode (i.e., polynucleotide detection tag sequence). This coding key aides in efficiently identifying the specific antigens that pair with T cells. Examples of an antigen and barcode key for the list of candidate antigens (patient-specific candidate neoantigens and MART-1 tumor antigen) of FIG. 4 is shown in FIGS. 5A-5B.

Embodiments of the present invention include a barcoded nanoparticle-antigen-MHC complex for use in screening antigen-specific T cells. As understood by a person skilled in the art, a single antigen may be assayed using the complex in the presence of T cells. However, assaying one candidate antigen is not as efficient as screening multiple candidate antigens. According to embodiments of the present invention, different barcoded NP antigen-MHC complexes are prepared using different candidate antigens with corresponding unique coding regions forming a library of barcoded NP-antigen-MHC complexes. The following methods are described using a library of the barcoded NP-antigen-MHC complexes; however the method may be followed or easily adapted for screening a single candidate antigen.

According to embodiments of the present invention, isolation and identification of patient-derived and antigen-specific T cells using a library of barcoded-NP-antigen-MHC complexes includes incubating the candidate antigen complexes with patient-derived T cells. In some embodiments, the patient-derived T cells are isolated from the patient's peripheral blood mononuclear cells (PBMCs) or tumor infiltrating lymphocytes (TILs). In some embodiments of the present invention, both CD4+ and CD8+ T cells are labeled and sorted from PBMCs or TILS using anti-CD4 and anti-CD8 fluorescent antibodies with live populations of CD4+ and CD8+ single-positive cells sorted using fluorescence-activated cell sorting (FACS), in order to isolate only CD4+ or CD8+ cells. In some embodiments of the present invention, T cells that are positive for both CD4 and CD8 may be isolated using an anti-CD3 fluorescent antibody followed by FACS. A person skilled in the art is able to determine the type of T cells to isolate for the type or types of antigen-MHC complex being used. For example, if the library is made exclusively of MHC I molecules, the T cell population may be only CD8+, whereas MCH II molecules would require CD4+ T cells. In other embodiments, an antigen library having both MHC I and MHC II molecules may be incubated with T cells that are both CD4 and CD8 positive. In still other embodiments, an antigen library having either MHC I or MHC II molecules may be screened with T cells that are positive for both CD4 and CD8.

Figure 6:
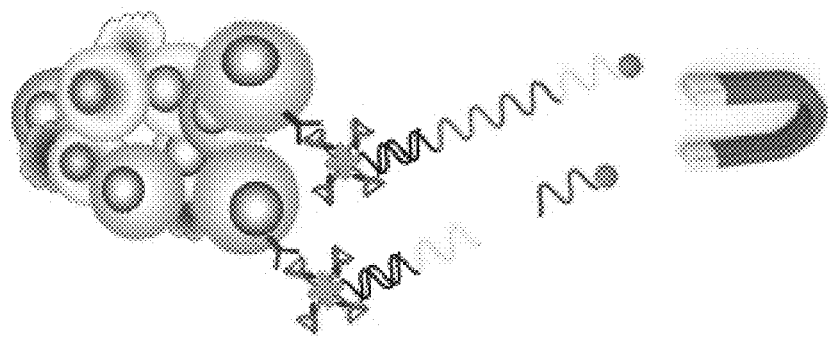
FIG. 6 is a schematic depicting a barcoded magnetic NP-antigen-MHC complex paired with a cognate T cell receptor (TCR) on a T cell, and isolation of the magnetic NP with a magnet, according to embodiments of the present invention.

Embodiments of the present invention include incubating a barcoded NP-antigen-MHC complex library with a suspension of CD4+, CD8+ or CD4+/CD8+ T cells. Incubation of the nanoparticle library with the T cell suspension allows for a complete and thorough exposure of the nanoparticle-bound antigen to the various T-cell receptors. This method may include rocking or rotation of the cells. Following incubation of the antigen complex and the T cells, the nanoparticle is selectively isolated or selectively collected. For example, if the nanoparticle is magnetic, applying a magnet to the suspension allows for separation of nanoparticles in a complex with antigen paired T cells and removal of unpaired T cells. An example of isolated magnetic nanoparticles with paired T cells is shown schematically in FIG. 6. Alternatively, if the nanoparticle is a polystyrene nanoparticle, the unpaired T cells may be separated by gravity (e.g., centrifugation). After separation of unpaired T cells, in some embodiments, the isolated nanoparticles are washed at least once to remove any non-specifically associated T cells.

For analysis of the paired T cells isolated with the nanoparticle complex, the cells are loaded into a microfluidic device that separates and posits single cells in individual locations ("traps") in the channels of the device.

Figure 7:
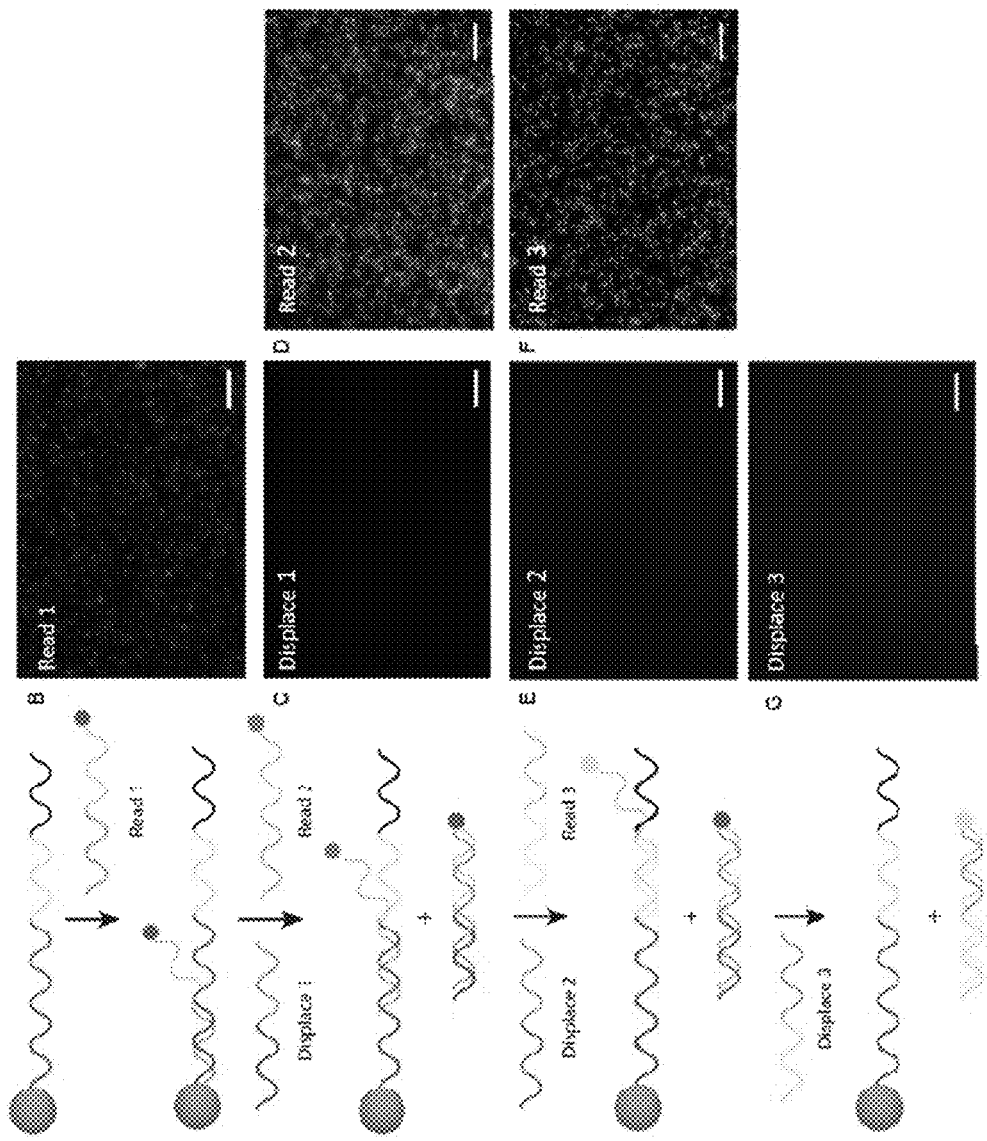
FIG. 7 shows a schematic (A) and fluorescent images (B-G) of DNA sequential barcode readouts, in which NP-DNA is first hybridized to Read 1 DNA to give red fluorescence as shown in image B; Displace 1 DNA and Read 2 DNA are introduced to remove Read 1 DNA as shown in image C and yield green fluorescence as show in image D; a similar process is followed to remove Read 2 DNA as shown in image E and generate the third yellow fluorescence signal as shown in image F, with a scale bar of 50 um, according to embodiments of the present invention.

As used herein with respect to the barcoded nanoparticle antigen-MHC complex, "a paired T cell" and "a T cell paired antigen MHC complex" refers to the complex of a T cell having a T cell receptor epitope that binds to an antigen peptide in a barcoded nanoparticle antigen-MHC complex. Accordingly, with the paired T cells separated in the cell trapping device, the coding regions (barcodes) of the paired antigen-MHC complex are identified in situ to determine the sequence of the cognate peptide antigen. Accordingly, each coding region is read starting with coding region 1. All possible complementary polynucleotide sequences for coding region 1 are linked to a distinguishable fluorescent dye forming a dye-polynucleotide decoder sequence that hybridizes the fluorescence to the complementary coding region on the nanoparticle, thereby "reading" coding region 1. As used herein, a "distinguishable fluorescent dye," and "distinguishable dye" refer to a dye of a color that is visually distinct from another dye. Any suitable dye may be used that is capable of being linked to a polynucleotide. In order to read the second coding region, a "displacement" polynucleotide is added to remove the dye-polynucleotide decoder of coding region 1 followed by or together with all of the possible dye-polynucleotide decoder sequences corresponding to coding region 2. In the decoding of more than one coding region, after coding region 1 is read, the polynucleotide detection tag is partially decoded." That is, a "partially decoded polynucleotide detection tag" has at least one, but not all coding regions decoded. Subsequent coding regions are read using this read-displace/read-displace/read format. This step-wise readout technology was validated using barcoded particles as depicted and shown in FIG. 7. As understood by those skilled in the art, for this fluorescent reading of the coding regions in a library of barcoded nanoparticles, one distinguishable fluorescent dye may only be associated with one decoder sequence for each coding region position. For example, for reading coding region 2, a red fluorescent dye may only correspond to one specific decoding sequence for decoding coding region 2. In some embodiments of the present invention, the polynucleotide decoder sequences are ssDNA or RNA. For example, as listed in the table in FIG. 8A, ssDNA decoding sequences M1, M2, M3, M5, M6, M7, M9, M10, and M11 are fluorescent dye-linked decoding sequences that hybridize to respective coding region of D1, D2, D3, D5, D6, D7, D9, D10, and D11 (FIG. 4), with each decoding sequence shown in the color of the corresponding fluorescent dye. Example displacement ssDNA sequences corresponding to (i.e., that hybridize with) each decoding sequence in FIG. 8A include the ssDNA sequences M1 comp, M2 comp, M3 comp, M5 comp, M6 comp, M7 comp, M9 comp, M10 comp, and M11 comp as listed in the table of FIG. 8B.

Figure 9:
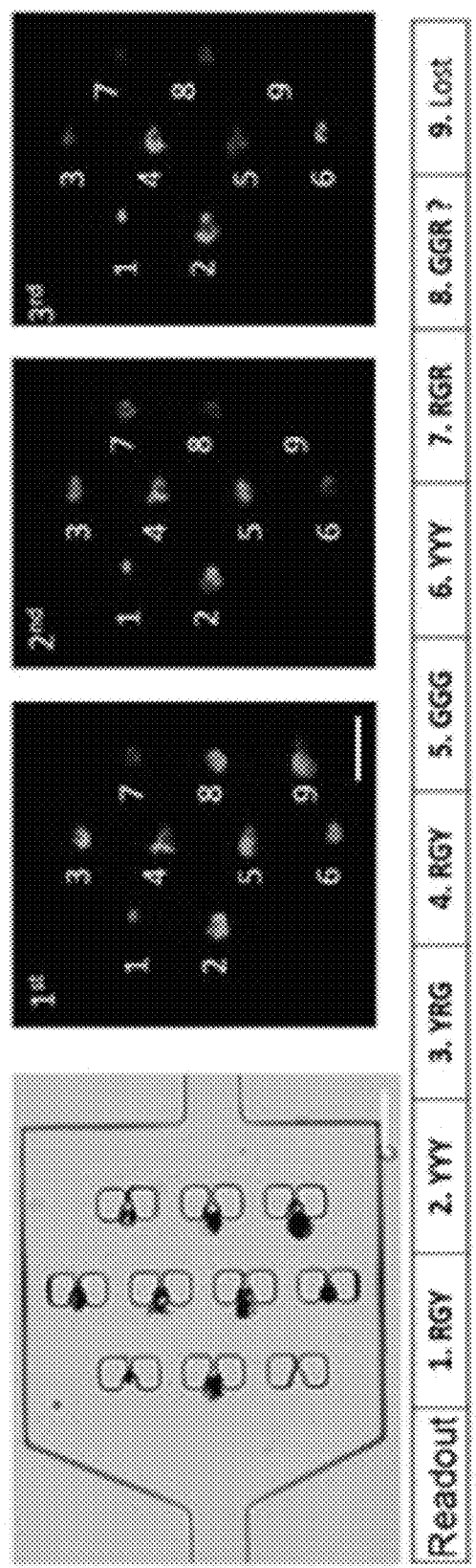
FIG. 9 shows single cell analysis of barcoded and precipitated neoantigen-specific T cells collected from a sample of expanded tumor infiltrating lymphocytes (TILs) from a patient (patient #1), in which the far left image is an optical micrograph of a microfluidic chamber equipped with 10 cell traps, 9 of which contain single barcoded T cells; with the fluorescent images (left to right), showing the readout of coding region 1 (1st), the readout of coding region 2 (2nd), and the readout of coding region 3, with the results of the readouts shown below the images with R=red, Y=yellow, and G=green, according to embodiments of the present invention.

In some embodiments of the present invention, the coding regions (barcodes) of the T cell paired-antigen MHC complex are identified in situ using the fluorescent dye-polynucleotide decoding "reader" sequences in combination with the "displacement" polynucleotide sequences. This method was carried out using a barcoded NP-antigen-MHC library of the 27 antigens in FIG. 5A, having the NP barcode (detection tag) sequences as listed in FIG. 4. After incubation with T cells derived from the patient's tumor infiltrating lymphocytes (TILs), the cells associated with the isolated magnetic nanoparticle were separated in a microfluidic cell trapping device as shown on the left in FIG. 9 in an optical micrograph of a microfluidic chamber equipped with 10 cell traps. As shown, only 9 of the cell traps contain single barcoded T cells. These 9 barcoded T cells were read and displaced using the fluorescent dye-linked decoding ssDNA sequences listed in FIGS. 8A and 8B, respectively. The fluorescent images for each coding region read are shown left to right in FIG. 9 with the coding region 1 image labeled as 1st, coding region 2 image labeled as 2nd, and coding region 3 labeled as 3rd. The colorimetric read outs for the 9 trapped cells is provided below the images (R=red, G=green, Y=yellow). It is noted that the cell at position 8 does not provide a clean read, and the cell at position 9 was lost. Using this method according to embodiments of the present invention, only the trapped cells providing clear unambiguous readouts are considered, thereby allowing for control of the fidelity of the screening process. Using the barcode key of FIG. 5, the corresponding neoantigens and the tumor antigen MART-1 were determined. For example, the cell at position 3 in FIG. 9 reads YRG corresponding to neoantigen 12 listed in FIG. 5A, and the cell at position 4 reads RGY corresponding to the MART-1 tumor antigen.

Embodiments of the present invention include a kit for preparing a library of barcoded nanoparticles, the kit including barcodes (polynucleotide detection tag) sequences, the corresponding fluorescent dye-linked polynucleotide decoder sequences for reading the barcodes, and the corresponding displacement polynucleotide sequences for removing the decoder sequences. The polynucleotide sequences include ssDNA or RNA. In some embodiments of the present invention the polynucleotide sequences are ssDNA.

In some embodiments of the present invention, the polynucleotide detection tag sequences are modified at their 5' end to a binding moiety for attachment to a nanoparticle. For example, the polynucleotide detection tag (ssDNA barcode) sequences in FIG. 4 are conjugated to a biotin molecule for binding to a streptavidin-nanoparticle; however any suitable binding moiety may be used. As described herein and as understood by a person skilled in the art, suitable binding moiety pairs are known in the art. Non-limiting examples of binding moieties include thiol, maleimide, adamantane, cyclodextrin, amine, carboxy, azide, and alkyne. In some embodiments of the present invention, the kit may also include modified nanoparticles modified with the cognate binding moiety corresponding to the binding moiety on the modified polynucleotide detection tags.

In some embodiments of the present invention, a kit for preparing a library of barcoded nanoparticles also includes a recombinant conditional MHC tetramer complex capable of being loaded with any MHC antigen peptide. The MHC may be MHC Class I or MHC Class II and includes any specific haplotype corresponding to the patient's haplotype. For example, the kit may include MHC Class I molecules corresponding to an HLA type listed in Table 7. For example, the kit may include MHC Class II molecules corresponding to HLA-DM, HLA-DO, HLA-DQ, and HLA in which the MHC II α chain is encoded by the HLA-A-DMA, HLA-DOA, HLA-DPA1, HLA-DQA2, or HLA-DRA gene and the β chain is encoded by HLA-DMB, HLA-DOB, HLA-DPB1, HLA-DQB1, HLA-DQB2, HLA-DRB1, HLA-DRB3, HLA-DRB4, or HLA-DRB5 gene.

In some embodiments of the present invention, a kit for preparing a library of barcoded nanoparticles includes modified polynucleotide detection tag sequences for attachment to nanoparticles. Alternative methods for identifying the trapped barcoded T cell may be used. For example, the polynucleotide detection tag sequences may be amplified and sequenced from the microfluidic device.

Using the in situ decoding readout method for identifying the polynucleotide detection tag and the corresponding antigen paired with the trapped T cell, does not destroy or adversely affect the T cell. Accordingly, after the antigen has been identified, the trapped T cell may be removed from the microfluidic device for further analysis and/or growth.

The following Examples are presented for illustrative purposes only, and do not limit the scope or content of the present application.

EXAMPLES

Example 1. Capture Efficiency of Antigen-Specific T Cells

Figure 10A:
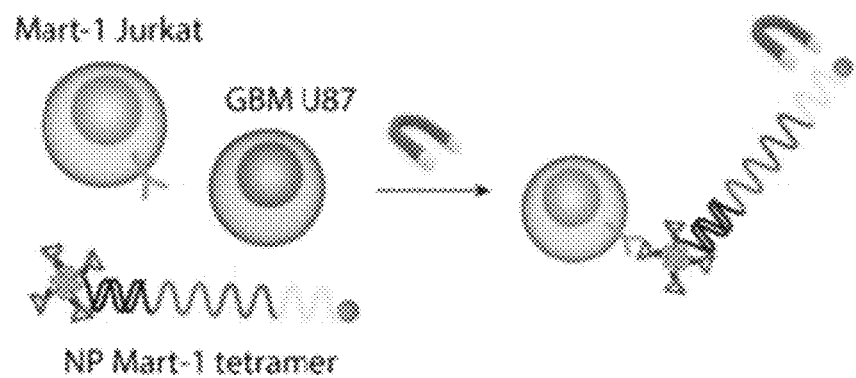
FIG. 10A is a schematic illustration of a barcoded NP-Mart-1 MHC tetramer for capture of Jurkats cells transduced with a Mart-1 specific T-cell receptor (green cell) from a mix of Jurkat and GBM U876 cells (blue cell), according to embodiments of the present invention.
Figure 10B:
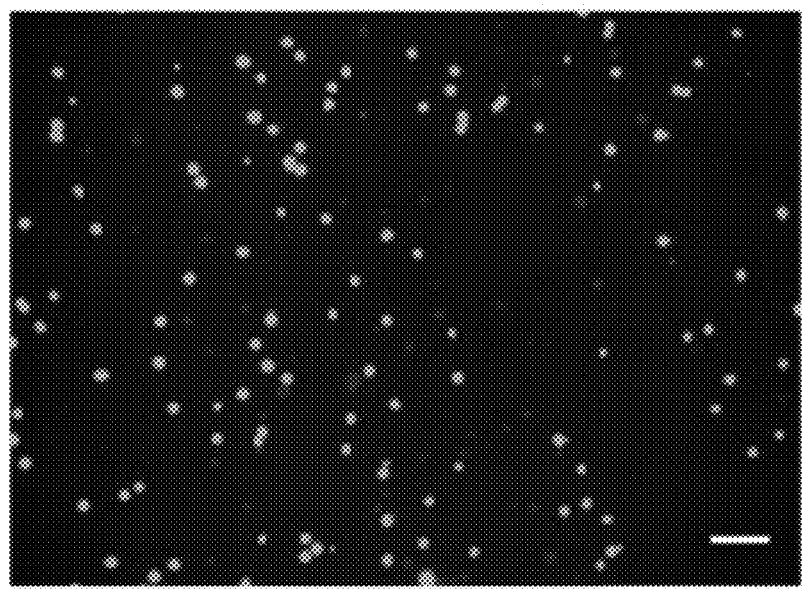
FIG. 10B shows a fluorescence image of mixed Jurkat cells (stained green) and GBM U87 cells (stained blue), according to embodiments of the present invention.
Figure 10C:
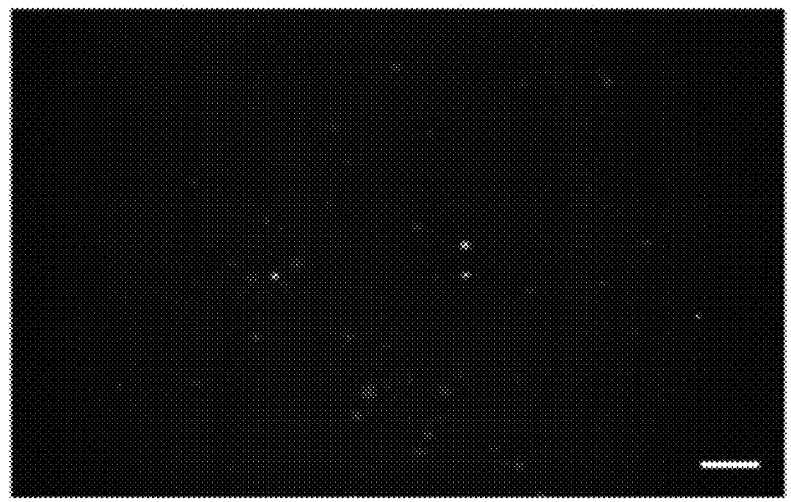
FIG. 10C shows an image of the cell supernatant after isolation of the barcoded NP-Mart-1 MHC tetramer from the Jurkat (green cells) and GBM U876 (blue cells) cell mixture of FIG. 10B, according to embodiments of the present invention.
Figure 10D:
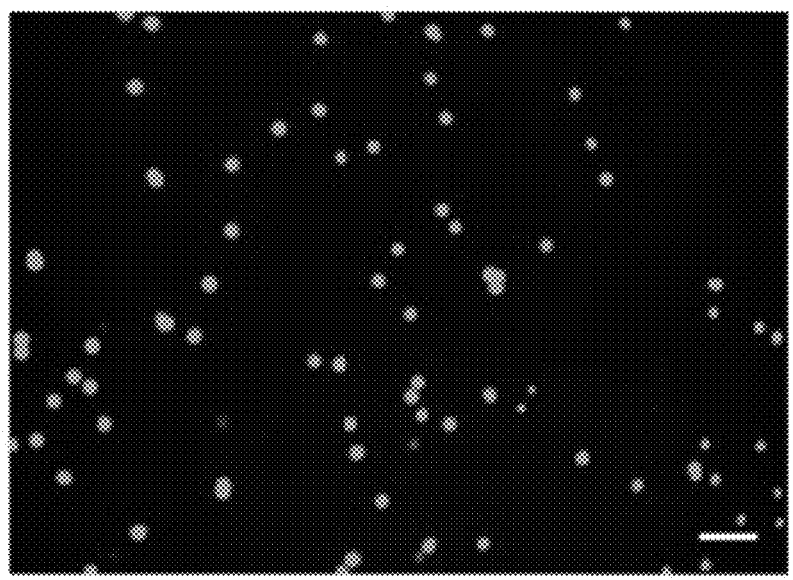
FIG. 10D shows an image of the cells associated with the magnetic pulldown of the barcoded NP-Mart-1 MHC tetramer from the Jurkat (green cells) and GBM U876 (blue cells) cell mixture of FIG. 10B, according to embodiments of the present invention.

The barcoded NP-antigen-MHC complex library was validated by employing selective capture of Mart-1 antigen specific T cells from a mixture of cells. FIG. 10A shows a schematic illustration of NP-Mart-1 tetramer for capture of Jurkat cells transduced with a Mart-1 specific T-cell receptor. FIG. 10B shows mixed Jurkat (stained green) and GBM U87 cells (stained blue). The NP-Mart-1 tetramer is incubated with the mixed cell population and magnetically enriched with cells from the supernatant shown in FIG. 10C, and from the magnetic pulldown shown in FIG. 10D.

Example 2. Use of Barcoded NP-Antigen-MHC Complex Library

Figure 11:
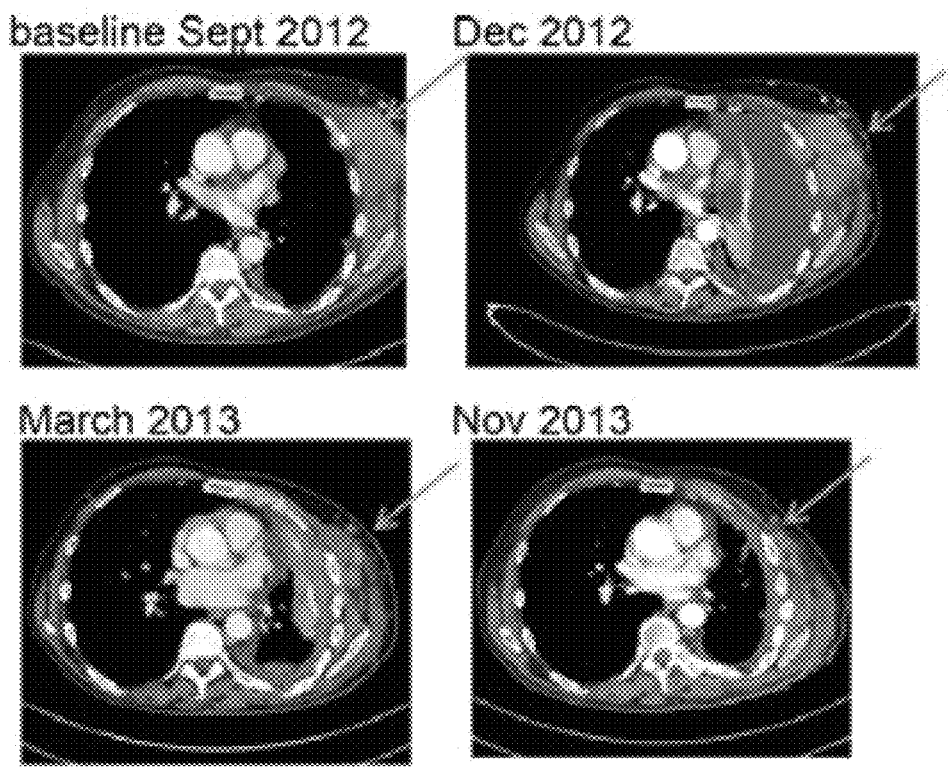
FIG. 11 shows a computerized axial tomography (CAT) scan of the melanoma tumor in the chest wall, pleura and lungs of patient #1.

The NP-antigen-MHC complex library tool was used to analyze CD8+ cells expanded from tumor infiltrating lymphocytes (TILs) collected from on-treatment tumor biopsies of two metastatic melanoma cancer patients who were positively responding to anti-PD-1 checkpoint inhibitor therapy at the time of biopsy as shown in FIG. 11. These two patients were treated with the anti-PD-1 antibody pembrolizumab within a phase I trial, and responses to this therapy are known to be mediated by tumor infiltrating CD8+ cells. For each patient, a pre-treatment biopsy was also collected (FIG. 11), and analyzed for both the tumor exome and gene expression. In silico analysis was carried out to prepare lists of putative neoantigens, rank ordered according to predicted Kd for HLA A*02.01 (Tables 1-4 below). Those lists, which were unique for each patient, informed the construction of the NP-barcoded NACS libraries constructed to present the top 27 putative neoantigens plus the MART-1 melanosomal antigen (neo-antigen #8 was excluded as it results in NP aggregation). For patient #1, the transcripts of the mutated proteins corresponding to neoantigen numbers 3, 5, 11, 26, 31, 34, 36, 37, 46 and 48 yielded zero mutation reads (Table 3) and were included in all assays as controls that spanned the sampled range of neoantigen/MHC binding affinities. from the microfluidic device for further analysis and/or growth.

TABLE 1

Putative neo-antigens for Patient #1.
Letter in the bracket indicates the native peptide.

| # | Neo-antigen | SEQ ID NOS (Neo-antigen & native) | $K_d$ (nM) |
|---|---|---|---|
| 1 | F(S)LGSLLILV | 1 & 51 | 5 |
| 2 | RLS(P)SCFDYV | 2 & 52 | 9 |
| 3 | S(P)LMNEDFIL | 3 & 53 | 11 |
| 4 | F(S)LGSLLILVV | 4 & 54 | 11 |
| 5 | S(P)LMNEDFILA | 5 & 55 | 11 |
| 6 | SLHD(G)LTDGV | 6 & 56 | 12 |
| 7 | KAWENF(S)PNV | 7 & 57 | 14 |
| 8 | LLSEFF(S)SCL | 8 & 58 | 18 |
| 9 | KLLSEFF(S)SCL | 9 & 59 | 20 |
| 10 | LQ(R)DSGLWFPV | 10 & 60 | 21 |
| 11 | S(P)LMNEDFILAV | 11 & 61 | 25 |
| 12 | Y(D)LYHRVDVI | 12 & 62 | 28 |
| 13 | FVANLFNTYL(P) | 13 & 63 | 29 |
| 14 | GLFH(R)SLYRSV | 14 & 64 | 29 |
| 15 | GLSE(G)KCSLV | 15 & 65 | 36 |
| 16 | HLQ(R)DSGLWFPV | 16 & 66 | 39 |
| 17 | TLANRFS(P)AV | 17 & 67 | 45 |
| 18 | FLVIV(A)PLSTI | 18 & 68 | 48 |
| 19 | GLSE(G)KCSLVV | 19 & 69 | 57 |
| 20 | F(P)LHGNSLYQKV | 20 & 70 | 61 |
| 21 | F(S)LRESQETL | 21 & 71 | 65 |

TABLE 1-continued

Putative neo-antigens for Patient #1. Letter in the bracket indicates the native peptide.

| # | Neo-antigen | SEQ ID NOS (Neo-antigen & native) | $K_d$ (nM) |
|---|---|---|---|
| 22 | LLSEFF(S)SCLA | 22 & 72 | 66 |
| 23 | QLDS(P)GTLIV | 23 & 73 | 67 |
| 24 | WMGLL(P)DLEV | 24 & 74 | 67 |
| 25 | FVLE(D)HEDGL | 25 & 75 | 71 |
| 26 | TL(P)VSLATETV | 26 & 76 | 75 |
| 27 | KMGKTIY(H)KYV | 27 & 77 | 76 |
| 28 | NLFNTYL(P)CL | 28 & 78 | 77 |
| 29 | RLSEV(A)MARM | 29 & 79 | 82 |
| 30 | VLTEIF(S)LGSL | 30 & 80 | 105 |
| 31 | ALYKEE(G)EQEPV | 31 & 81 | 133 |
| 32 | VLIDLIQRTKV(D) | 32 & 82 | 134 |
| 33 | MVC(R)TFCPPPL | 33 & 83 | 138 |
| 34 | LLFHS(P)PRAHL | 34 & 84 | 139 |
| 35 | V(M)LLHAFEGYNV | 35 & 85 | 147 |
| 36 | VTSSIVTL(P)V | 36 & 86 | 158 |
| 37 | SL(P)APPRTPEL | 37 & 87 | 212 |
| 38 | F(S)FVEASMSV | 38 & 88 | 223 |
| 39 | S(C)MLTARSWDSV | 39 & 89 | 248 |
| 40 | FVLE(D)HEDGLNL | 40 & 90 | 261 |
| 41 | SLQT(A)NVQRL | 41 & 91 | 273 |
| 42 | KVKCIPF(Y)AV | 42 & 92 | 313 |
| 43 | FVFSKYC(R)HRA | 43 & 93 | 366 |
| 44 | S(N)LVPEDEANI | 44 & 94 | 368 |
| 45 | ILPFF(L)YLGSA | 45 & 95 | 380 |
| 46 | RI(N)AGEEVTLTV | 46 & 96 | 416 |
| 47 | VLT(A)RLALLQL | 47 & 97 | 418 |
| 48 | LLEYRI(S)SENPV | 48 & 98 | 440 |
| 49 | MQQPSPQ(P)IPPV | 49 & 99 | 449 |
| 50 | GLFH(R)SLYRS | 50 & 100 | 463 |

TABLE 2

Putative neo-antigens for Patient #2. Letter in the bracket indicates the native peptide.

| # | Neo-antigen | SEQ ID NOS (Neo-antigen & native) | $K_d$ (nM) |
|---|---|---|---|
| 1 | LLTDLLFL(S)I | 101 & 129 | 4 |
| 2 | RLMERSIY(H)SA | 102 & 130 | 7 |
| 3 | FLVNDWLL(S)V | 103 & 131 | 8 |
| 4 | FLDSC(S)PHLPL | 104 & 132 | 8 |
| 5 | KMNELNY(H)CI | 105 & 133 | 10 |
| 6 | RLLTDLLFL(S)I | 106 & 134 | 10 |
| 7 | RLANLIW(R)RA | 107 & 135 | 11 |
| 8 | RLLTDLLFL(S) | 108 & 136 | 12 |
| 9 | RIYTEMC(R)FTV | 109 & 137 | 13 |
| 10 | VL(P)FEKKDFV | 110 & 138 | 16 |
| 11 | KIFCASF(S)RI | 111 & 139 | 17 |
| 12 | FL(S)IETDIQM | 112 & 140 | 17 |
| 13 | QLFQL(P)YNFEL | 113 & 141 | 23 |
| 14 | VLYFN(H)HYFPA | 114 & 142 | 24 |
| 15 | TVLGTPF(S)EV | 115 & 143 | 26 |
| 16 | SIY(H)SARYIFV | 116 & 144 | 26 |
| 17 | YALHWLYY(H)Y | 117 & 145 | 27 |
| 18 | KIS(P)SQPPPV | 118 & 146 | 28 |
| 19 | KL(S)STFLMKA | 119 & 147 | 29 |
| 20 | FTLFELAF(S)L | 120 & 148 | 31 |
| 21 | FLPRKENI(S)SV | 121 & 149 | 31 |
| 22 | VLQGC(R)LPCPV | 122 & 150 | 31 |
| 23 | F(S)LANSGGWV | 123 & 151 | 33 |
| 24 | YILLYKN(D)GV | 124 & 152 | 37 |
| 25 | F(S)LYKSQGEI | 125 & 153 | 40 |
| 26 | FIS(P)WGPASI | 126 & 154 | 44 |
| 27 | LL(S)YELQPGT | 127 & 155 | 44 |
| 28 | NLY(H)EEDALL | 128 & 156 | 45 |

TABLE 3

Full analysis of neoantigens and mutated genes for Patient #1. Table 3 discloses "peptide Tumor" sequences as SEQ ID NOS 1-50 and "peptide Normal" sequences as SEQ ID NOS 51-100, all respectively, in order of appearance.

| neo-antigen | Gene | Protein_Change | FPKM | Mut_RNA_Reads | pepLen | mutantpep Position | peptide Tumor | Affinity (nM) | peptide Normal | Affinity (nM) | DeltaAbs |
|---|---|---|---|---|---|---|---|---|---|---|---|
| 1 | DYM | p.S434F | 20.5835 | 53 | 9 | 1 | FLGSLLILV | 5 | SLGSLLILV | 13 | -8 |
| 2 | SLC8A2 | p.P719S | 0.025223 | 4 | 9 | 3 | RLSSCFDYV | 9 | RLPSCFDYV | 15 | -6 |
| 3 | IFNA7 | p.P133S | 0 | 0 | 9 | 1 | SLMNEDFIL | 11 | PLMNEDFIL | 820 | -809 |
| 4 | DYM | p.S434F | 20.5835 | 53 | 10 | 1 | FLGSLLILVV | 11 | SLGSLLILVV | 33 | -22 |
| 5 | IFNA7 | p.P133S | 0 | 0 | 10 | 1 | SLMNEDFILA | 11 | PLMNEDFILA | 550 | -539 |
| 6 | RFTN1 | p.G348D | 5.27924 | 36 | 9 | 4 | SLHDLTDGV | 12 | SLHGLTDGV | 36 | -24 |
| 7 | PRRC2C | p.S2260F | 27.70395 | 179 | 9 | 6 | KAWENFPNV | 14 | KAWENSPNV | 22 | -8 |
| 8 | FASTKD1 | p.S159F | 10.8846 | 26 | 9 | 6 | LLSEFFSCL | 18 | LLSEFSSCL | 26 | -8 |
| 9 | FASTKD1 | p.S159F | 10.8846 | 26 | 10 | 7 | KLLSEFFSCL | 20 | KLLSEFSSCL | 32 | -12 |
| 10 | LDHD | p.R148Q | 4.41145 | 20 | 10 | 2 | LQDSGLWFPV | 21 | LRDSGLWFPV | 2629 | -2608 |
| 11 | IFNA7 | p.P133S | 0 | 0 | 11 | 1 | SLMNEDFILAV | 25 | PLMNEDFILAV | 94 | -69 |
| 12 | USP7 | p.D789Y | 41.2267 | 259 | 9 | 1 | YLYHRVDVI | 28 | DLYHRVDVI | 10865 | -10837 |
| 13 | PLS1 | p.P376L | 4.53658 | 19 | 10 | 10 | FVANLFNTYL | 29 | FVANLFNTYP | 3399 | -3370 |
| 14 | CPVL | p.R25H | 5.87024 | 2 | 10 | 4 | GLFHSLYRSV | 29 | GLFRSLYRSV | 49 | -20 |
| 15 | PCDHB6 | p.G327E | 11.7725 | 91 | 9 | 4 | GLSEKCSLV | 36 | GLSGKCSLV | 132 | -96 |
| 16 | LDHD | p.R148Q | 4.41145 | 20 | 11 | 3 | HLQDSGLWFPV | 39 | HLRDSGLWFPV | 126 | -87 |
| 17 | GOSR1 | p.P213S | 14.3655 | 84 | 9 | 7 | TLANRFSAV | 45 | TLANRFPAV | 13 | 32 |
| 18 | CHD8 | p.A866V | 10.04205 | 64 | 10 | 5 | FLVIVPLSTI | 48 | FLVIAPLSTI | 38 | 10 |
| 19 | PCDHB6 | p.G327E | 11.7725 | 91 | 10 | 4 | GLSEKCSLVV | 57 | GLSGKCSLVV | 107 | -50 |
| 20 | ENTHD2 | p.P110F | 2.401075 | 47 | 11 | 1 | FLHGNSLYQKV | 61 | PLHGNSLYQKV | 1934 | -1873 |
| 21 | PPFIA4 | p.S43F | 0.305613 | 6 | 9 | 1 | FLRESQETL | 65 | SLRESQETL | 522 | -457 |
| 22 | FASTKD1 | p.S159F | 10.8846 | 26 | 10 | 6 | LLSEFFSCLA | 66 | LLSEFSSCLA | 133 | -67 |
| 23 | LGALS8 | p.P29S | 11.86285 | 6 | 9 | 4 | QLDSGTLIV | 67 | QLDPGTLIV | 70 | -3 |
| 24 | OSGIN1 | p.P233L | 7.949295 | 84 | 9 | 5 | WMGLLDLEV | 67 | WMGLPDLEV | 202 | -135 |

TABLE 3-continued

Full analysis of neoantigens and mutated genes for Patient #1. Table 3 discloses "peptide Tumor" sequences as SEQ ID NOS 1-50 and "peptide Normal" sequences as SEQ ID NOS 51-100, all respectively, in order of appearance.

| neo-antigen | Gene | Protein_Change | FPKM | Mut_RNA_Reads | pepLen | mutantpep Position | peptide Tumor | Affinity (nM) | peptide Normal | Affinity (nM) | DeltaAbs |
|---|---|---|---|---|---|---|---|---|---|---|---|
| 25 | NUMA1 | p.D136E | 29.5143 | 144 | 9 | 4 | FVLEHEDGL | 71 | FVLDHEDGL | 79 | -8 |
| 26 | PCLO | p.P2787L | 0.07751 | 0 | 10 | 2 | TLVSLATETV | 75 | TPVSLATETV | 20558 | -20483 |
| 27 | SNRNP200 | p.H1175Y | 51.15825 | 540 | 10 | 7 | KMGKTIYKYV | 76 | KMGKTIHKYV | 117 | -41 |
| 28 | PLS1 | p.P376L | 4.53658 | 19 | 9 | 7 | NLFNTYLCL | 77 | NLFNTYPCL | 42 | 35 |
| 29 | MCM6 | p.A630V | 11.7303 | 33 | 9 | 5 | RLSEVMARM | 82 | RLSEAMARM | 117 | -35 |
| 30 | DYM | p.S434F | 20.5835 | 53 | 10 | 6 | VLTEIFLGSL | 105 | VLTEISLGSL | 185 | -80 |
| 31 | IGSF1 | p.G718E | 0.029302 | 0 | 11 | 6 | ALYKEEEQEPV | 133 | ALYKEGEQEPV | 133 | 0 |
| 32 | TAOK1 | p.D299V | 9.740685 | 32 | 11 | 11 | VLIDLIQRTKV | 134 | VLIDLIQRTKD | 21537 | -21403 |
| 33 | QSER1 | p.R1185C | 9.301975 | 41 | 10 | 3 | MVCTFCPPPL | 138 | MVRTFCPPPL | 1307 | -1169 |
| 34 | FAM83B | p.P127S | 0.003497 | 0 | 10 | 5 | LLFHSPRAHL | 139 | LLFHPPRAHL | 222 | -83 |
| 35 | KIF1C | p.M81V | 26.47415 | 744 | 11 | 1 | VLLHAFEGYNV | 147 | MLLHAFEGYNV | 73 | 74 |
| 36 | PCLO | p.P2787L | 0.07751 | 0 | 9 | 8 | VTSSIVTLV | 158 | VTSSIVTPV | 57 | 101 |
| 37 | C8orf86 | p.P192L | 0 | 0 | 10 | 2 | SLAPPRTPEL | 212 | SPAPPRTPEL | 26625 | -26413 |
| 38 | RETSAT | p.S492F | 55.40045 | 200 | 9 | 1 | FFVEASMSV | 223 | SFVEASMSV | 2721 | -2498 |
| 39 | ADCK1 | p.C379S | 4.45008 | 22 | 11 | 1 | SMLTARSWDSV | 248 | CMLTARSWDSV | 729 | -481 |
| 40 | NUMA1 | p.D136E | 29.5143 | 144 | 11 | 4 | FVLEHEDGLNL | 261 | FVLDHEDGLNL | 358 | -97 |
| 41 | RPL13 | p.A112T | 403.4245 | 23 | 9 | 4 | SLQTNVQRL | 273 | SLQANVQRL | 152 | 121 |
| 42 | COPS7A | p.Y113F | 48.0616 | 372 | 9 | 7 | KVKCIPFAV | 313 | KVKCIPYAV | 465 | -152 |
| 43 | LYST | p.R395C | 36.5952 | 55 | 10 | 7 | FVFSKYCHRA | 366 | FVFSKYRHRA | 1426 | -1060 |
| 44 | SLC39A10 | p.N393S | 20.23725 | 86 | 10 | 1 | SLVPEDEANI | 368 | NLVPEDEANI | 1530 | -1162 |
| 45 | DUSP4 | p.L203F | 54.64275 | 803 | 10 | 5 | ILPFFYLGSA | 380 | ILPFLYLGSA | 786 | -406 |
| 46 | SNTG1 | p.N127I | 0 | 0 | 11 | 2 | RIAGEEVTLTV | 416 | RNAGEEVTLTV | 7235 | -6819 |
| 47 | TTC34 | p.A88T | 0.016071 | 1089 | 10 | 3 | VLTRLALLQL | 418 | VLARLALLQL | 146 | 272 |
| 48 | F13A1 | p.S305I | 0.51986 | 0 | 11 | 6 | LLEYRISENPV | 440 | LLEYRSSENPV | 813 | -373 |

TABLE 3-continued

Full analysis of neoantigens and mutated genes for Patient #1. Table 3 discloses "peptide Tumor" sequences as SEQ ID NOS 1-50 and "peptide Normal" sequences as SEQ ID NOS 51-100, all respectively, in order of appearance.

| neo-antigen | Gene | Protein Change | FPKM | Mut_RNA Reads | pepLen | mutantpep Position | peptide Tumor | Affinity (nM) | peptide Normal | Affinity (nM) | (nM) DeltaAbs |
|---|---|---|---|---|---|---|---|---|---|---|---|
| 49 | PIAS2 | p.P138Q | 7.271005 | 27 | 11 | 7 | MQQPSPQIPPV | 449 | MQQPSPPIPPV | 367 | 82 |
| 50 | CPVL | p.R25H | 5.87024 | 2 | 9 | 4 | GLFHSLYRS | 463 | GLFRSLYRS | 1048 | -585 |

TABLE 4

Full analysis of neoantigens and mutated genes for Patient #2. Table 4 discloses "peptide Tumor" sequences as SEQ ID NOS 101-128 and "peptide Normal" sequences as SEQ ID NOS 129-156, all respectively, in order of appearance.

| neo-antigen | Gene | Protein Change | FPKM | Mut_RNA Reads | pepLen | mutantpep Position | peptide Tumor | Affinity (nM) | peptide Normal | Affinity (nM) | (nM) DeltaAbs |
|---|---|---|---|---|---|---|---|---|---|---|---|
| 1 | LRBA | p.S1325L | 1.881915 | 6 | 9 | 8 | LLTDLLFLI | 4 | LLTDLLFSI | 4 | 0 |
| 2 | TK2 | p.H137Y | 4.86209 | 18 | 10 | 8 | RLMERSIYSA | 7 | RLMERSIHSA | 19 | -12 |
| 3 | PKD1 | p.S3220L | 6.81945 | 7 | 9 | 8 | FLVNDWLLV | 8 | FLVNDWLSV | 7 | 1 |
| 4 | ATMIN | p.S715C | 8.58103 | 43 | 10 | 5 | FLDSCPHLPL | 8 | FLDSSPHLPL | 9 | -1 |
| 5 | CASK | p.H512Y | 2.38613 | 9 | 9 | 7 | KMNELNYCI | 10 | KMNELNHCI | 24 | -14 |
| 6 | LRBA | p.S1325L | 1.88192 | 6 | 10 | 9 | RLLTDLLFLI | 10 | RLLTDLLFSI | 8 | 2 |
| 7 | PIGT | p.R570W | 161.945 | 228 | 9 | 7 | RLANLIWRA | 11 | RLANLIRRA | 763 | -752 |
| 8 | LRBA | p.S1325L | 1.881915 | 6 | 9 | 9 | RLLTDLLFL | 12 | RLLTDLLFS | 909 | -897 |
| 9 | EPHB1 | p.R90C | 1.78296 | 2 | 10 | 7 | RIYTEMCFTV | 13 | RIYTEMRFTV | 41 | -28 |
| 10 | TRAPPC9 | p.P181L | 5.145625 | 5 | 9 | 2 | VLFEKKDFV | 16 | VPFEKKDFV | 18017 | -18001 |
| 11 | MROH2A | p.S1064F | 0.257644 | 18 | 9 | 7 | KIFCASFRI | 17 | KIFCASSRI | 261 | -244 |
| 12 | LRBA | p.S1325L | 1.881915 | 6 | 9 | 2 | FLIETDIQM | 17 | FSIETDIQM | 4758 | -4741 |
| 13 | ELOVL3 | p.P17L | 0.64389 | 1 | 10 | 5 | QLFQLYNFEL | 23 | QLFQPYNFEL | 35 | -12 |
| 14 | POMT2 | p.H664N | 8.53243 | 135 | 10 | 5 | VLYFNHYFPA | 24 | VLYFHHYFPA | 22 | 2 |
| 15 | SLC5A8 | p.S76F | 0.112721 | 1 | 9 | 7 | TVLGTPFEV | 26 | TVLGTPSEV | 391 | -365 |
| 16 | TK2 | p.H137Y | 4.86209 | 18 | 10 | 3 | SIYSARYIFV | 26 | SIHSARYIFV | 205 | -179 |
| 17 | DYDC2 | p.H39Y | 0.328192 | 1 | 9 | 8 | YLAHWLYYY | 27 | YLAHWLYHY | 99 | -72 |
| 18 | SASH1 | p.P981S | 3.694035 | 10 | 9 | 3 | KISSQPPPV | 28 | KIPSQPPPV | 51 | -23 |

TABLE 4-continued

Full analysis of neoantigens and mutated genes for Patient #2. Table 4 discloses "peptide Tumor" sequences as SEQ ID NOS 101-128 and "peptide Normal" sequences as SEQ ID NOS 129-156, all respectively, in order of appearance.

| neo-antigen | Gene | Protein Change | FPKM | Mut_RNA_Reads | pepLen | mutantpep Position | peptide Tumor | peptide Affinity (nM) | peptide Normal | Affinity (nM) | (nM) DeltaAbs |
|---|---|---|---|---|---|---|---|---|---|---|---|
| 19 | TERF1 | p.S252L | 7.794875 | 20 | 9 | 2 | KLSTFLMKA | 29 | KSSTFLMKA | 9473 | -9444 |
| 20 | TTC39B | p.S634F | 1.13525 | 4 | 9 | 8 | FTLFELAFL | 31 | FTLFELASL | 55 | -24 |
| 21 | CDK12 | p.S433I | 3.62697 | 1 | 10 | 8 | FLPRKENISV | 31 | FLPRKENSSV | 75 | -44 |
| 22 | EPB41L4 | p.R127C | 3.31517 | 3 | 10 | 5 | VLQGCLPCPV | 31 | VLQGRLPCPV | 75 | -44 |
| 23 | CCDC61 | p.S469F | 10.9458 | 51 | 9 | 1 | FLANSGGWV | 33 | SLANSGGWV | 300 | -267 |
| 24 | EPDR1 | p.D100N | 18.869 | 27 | 9 | 7 | YILLYKNGV | 37 | YILLYKDGV | 59 | -22 |
| 25 | TTC39B | p.S634F | 1.13525 | 4 | 9 | 1 | FLYKSQGEI | 40 | SLYKSQGEI | 286 | -246 |
| 26 | TUBG1 | p.P350S | 30.40205 | 39 | 9 | 3 | FISWGPASI | 44 | FIPWGPASI | 74 | -30 |
| 27 | PCDHA4 | p.S608L | 0.590446 | 3 | 9 | 2 | LLYELQPGT | 44 | LSYELQPGT | 11654 | -11610 |
| 28 | B3GALNT | p.H304Y | 5.16678 | 14 | 9 | 3 | NLYEEDALL | 45 | NLHEEDALL | 273 | -228 |

Figure 12:
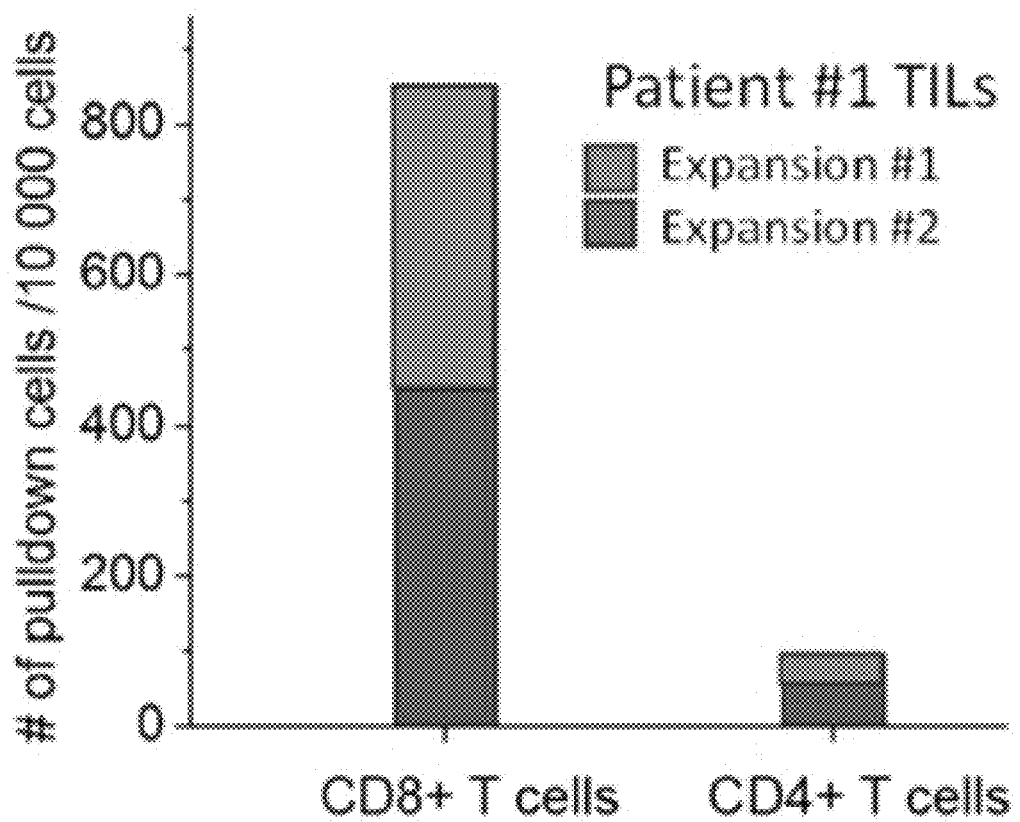
FIG. 12 is a graph showing the capture percentage of neoantigen-specific CD8+ T cells for patient #1 using two independent cell captures (expansion #1 in orange and expansion #2 in blue) with barcoded NP-antigen-MHC complex library of 27 putative antigens as listed in FIG. 5, with non-selective capture about 0.5% as estimated by the number of CD4+ positive T cells that were captured using the same method, according to embodiments of the present invention.
Figure 13:
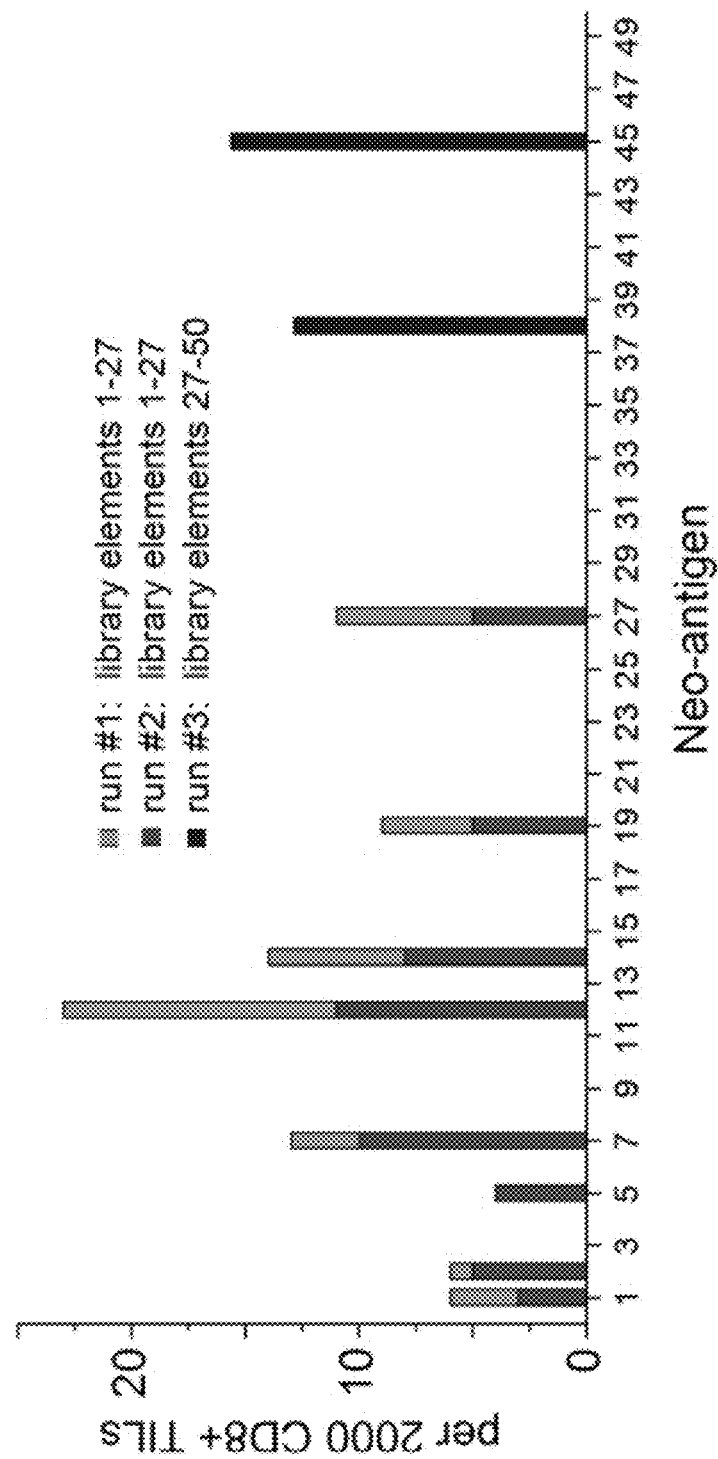
FIG. 13 is a graph showing the neoantigen population detected from expanded TILs from the tumor of patient #1, in which for each run of the three runs shown (Run #1=green, Run #2=red, and Run #3=blue), approximately 10,000 CD8+ TILs were analyzed and isolated within the cell capture chambers of the microfluidic chip for fluorescence-based readouts of the attached NP-barcodes; where Runs #1 and #2 utilized the same 27-element NP barcoded antigen-MHC library with the 27 neoantigens of FIG. 5 and Run #3 utilized a NP-barcoded antigen-MHC library designed to capture CD8+ T cells specific to neoantigens having a rank order of 28-50, according to embodiments of the present invention.
Figure 14A:
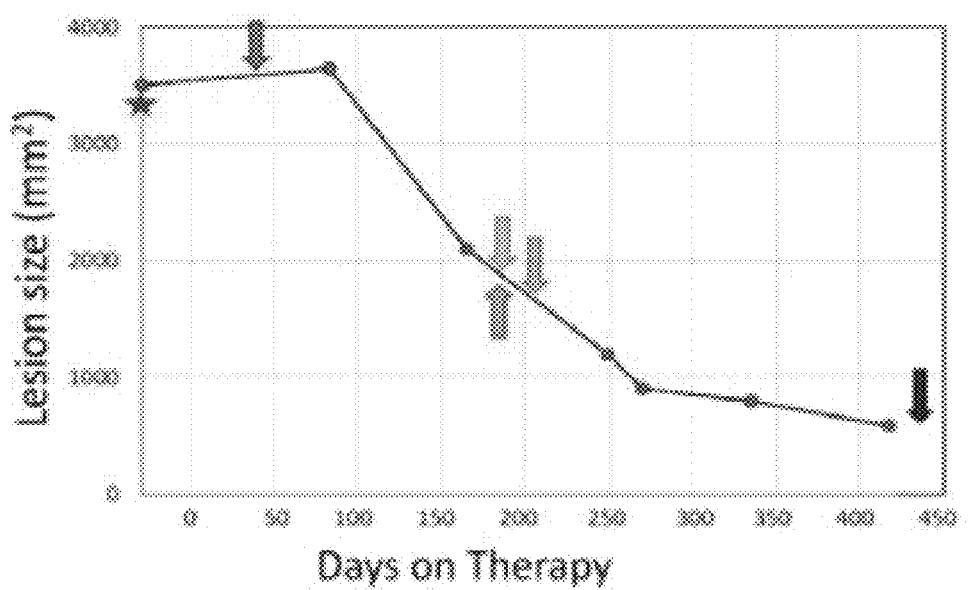
FIG. 14A shows a timeline of lesion size in Patient #1, where Day 0 corresponds to the start of anti-PD1 therapy and a baseline tumor biopsy (indicated by the red star) was collected for genomic and transcriptomic analysis at day 28 with the black dots corresponding to the CT scan measurement dates as shown in FIG. 11, with colored arrows (orange, purple/pink, blue, green, and black corresponding to same colored data bars in FIG. 14B, according to embodiments of the present invention.
Figure 14B:
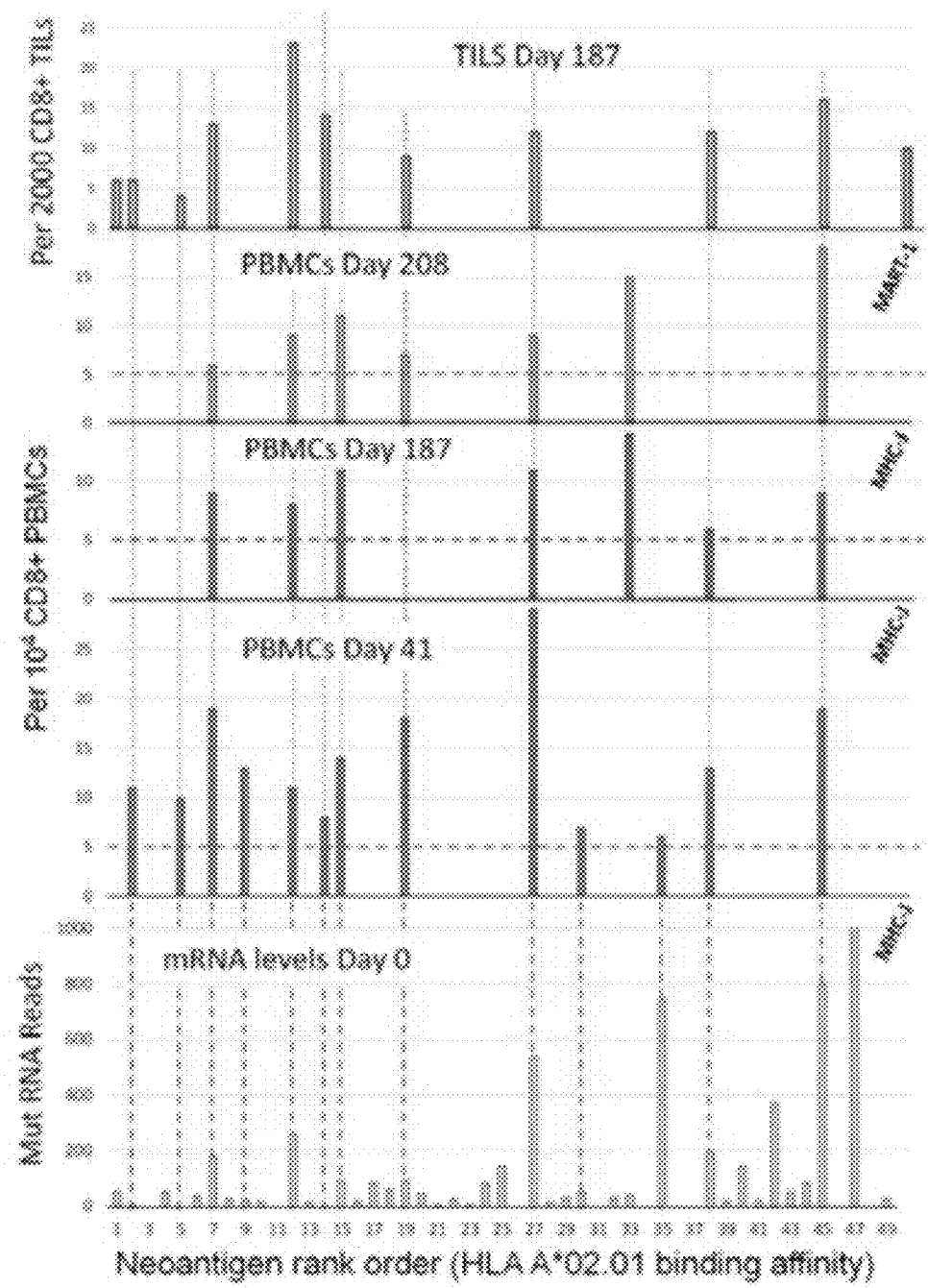
FIG. 14B shows graphs of neoantigen-specific T cell populations detected from TILs collected at Day 187 (top graph)(purple/pink bars) and PBMCs over the course of the therapy for Patient #1 (with the corresponding lesion size shown in FIG. 14A with orange, green, and blue bars matching same colored arrows), along with mutation-containing mRNA read counts for the mutant proteins (bottom graph) from the baseline RNA-sequencing, where the horizontal dashed lines in the PBMC analysis graphs represent the signal threshold above which the identification of a T cell population is statistically significant; the vertical gray dashed lines indicate T cell populations detected across the different time points and patient materials, while the vertical orange dashed lines correspond to transcripts and corresponding T cell populations detected at day 41; and for the TILs analysis, the MART-1 tumor antigen was included as library element #50, while for the PBMCs, the library element containing the conditional antigen (MHC-J) was included as that element, according to embodiments of the present invention.

The strongest binding 27 neoantigens for patient #1 are listed in FIG. 5A. For patient #1, the corresponding NP-barcoded NACS libraries captured 4.5-5% of the CD8+ TILs with a 0.5% non-selective capture, as gauged by testing the library against CD4+ T cells from the same patient tumors (FIG. 12). For the patient #1 sample, in two separate runs on two separate vials of expanded TILs, the barcoded T cells were loaded into the microfluidic chip and sequential fluorescent reads were performed to identify, in parallel, the same 8 neoantigen-specific T cell populations (plus MART-1 specific cells) (FIG. 13). All but very low-abundance populations (1 or 2 incidents per analysis) were detected in both assays. The most abundant population was specific for neoantigen #12, and accounted for about 12 cells per 1000 expanded TILs. For patient #1, the NP-barcoded NACS library was further expanded to analyze the TILS for specificities against neoantigens ranked 28-50 (Kd values up to 500 nM). Two additional populations were detected (#'s 38 and 45). The value of the barcoded, fluorescent read-out approach is that for each T cell captured, there is either a high fidelity read, or, occasionally, a nonsense read (see, for example, cell #8 in FIG. 9). Thus, the noise level of this approach is very low. The detected neoantigen-specific T cell populations are defined as those that were identified by 3 or more unambiguous reads, or were detected in both analyses of Patient #1 TILs. The summed analysis of Patient #1 TILS for the 50-element library is provided in FIG. 14B with the corresponding lesion analysis shown in FIG. 14A.

Example 3

Figure 15A:
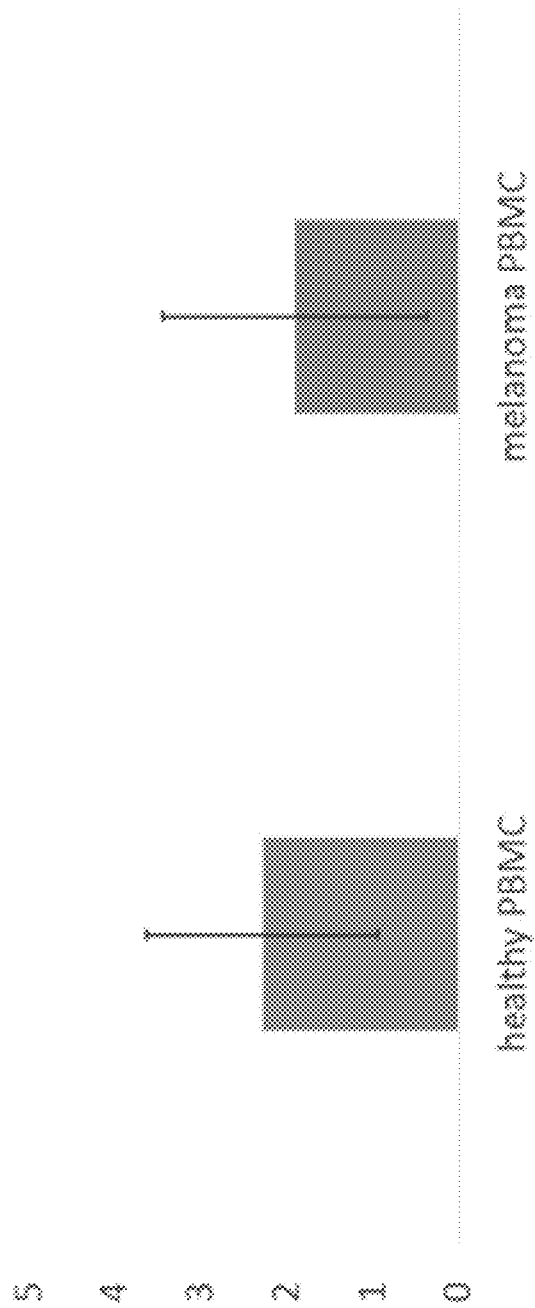
FIG. 15A is a graph of a control experiment showing the average number of T cells isolated using the NP-barcoded antigen-MHC library designed for patient #1 to capture CD8+ T cells from a healthy donor PBMCs (orange) and PBMCs from an unrelated melanoma patient (blue) on the same clinical trial, according to embodiments of the present invention.
Figure 15B:
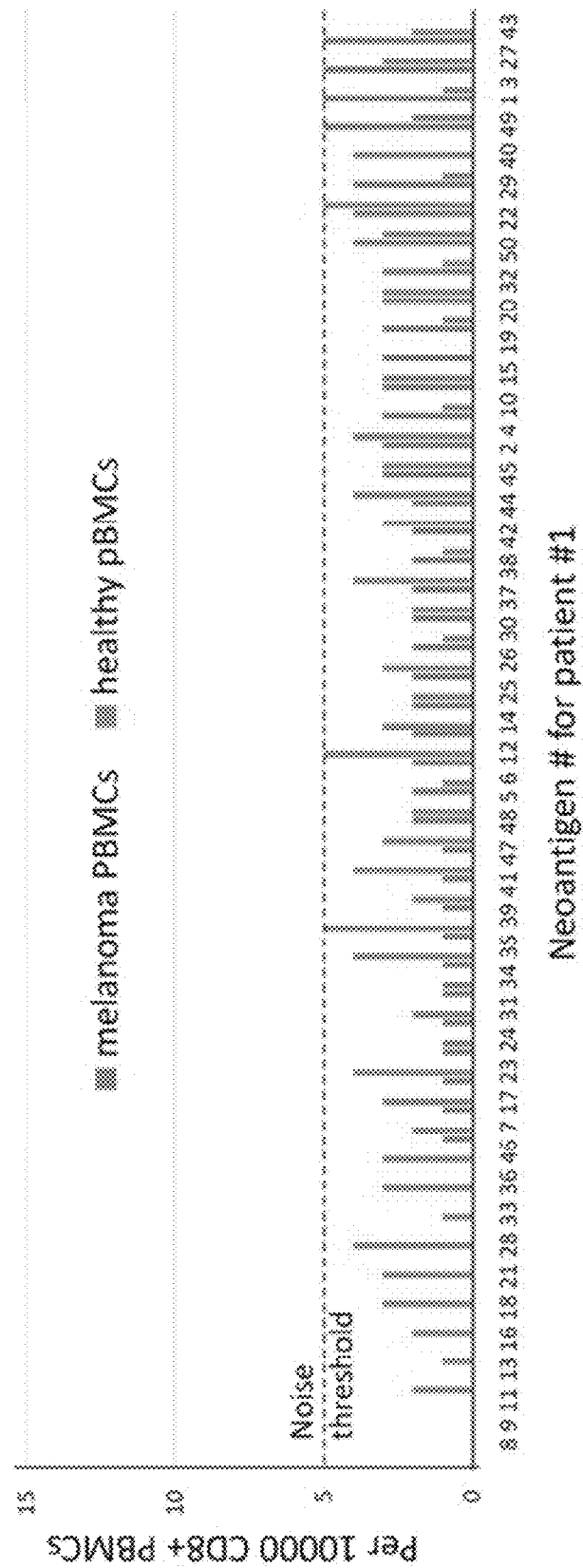
FIG. 15B is a graph in which the numerical labels on the x-axis correspond to the rank-order of the putative neoantigens, illustrating that there is no correlation between the two controls in FIG. 15A, with orange bars representing healthy PMBCs and blue bars representing melanoma PMBCs from a different patient (not Patient #1), according to embodiments of the present invention.
Figure 16:
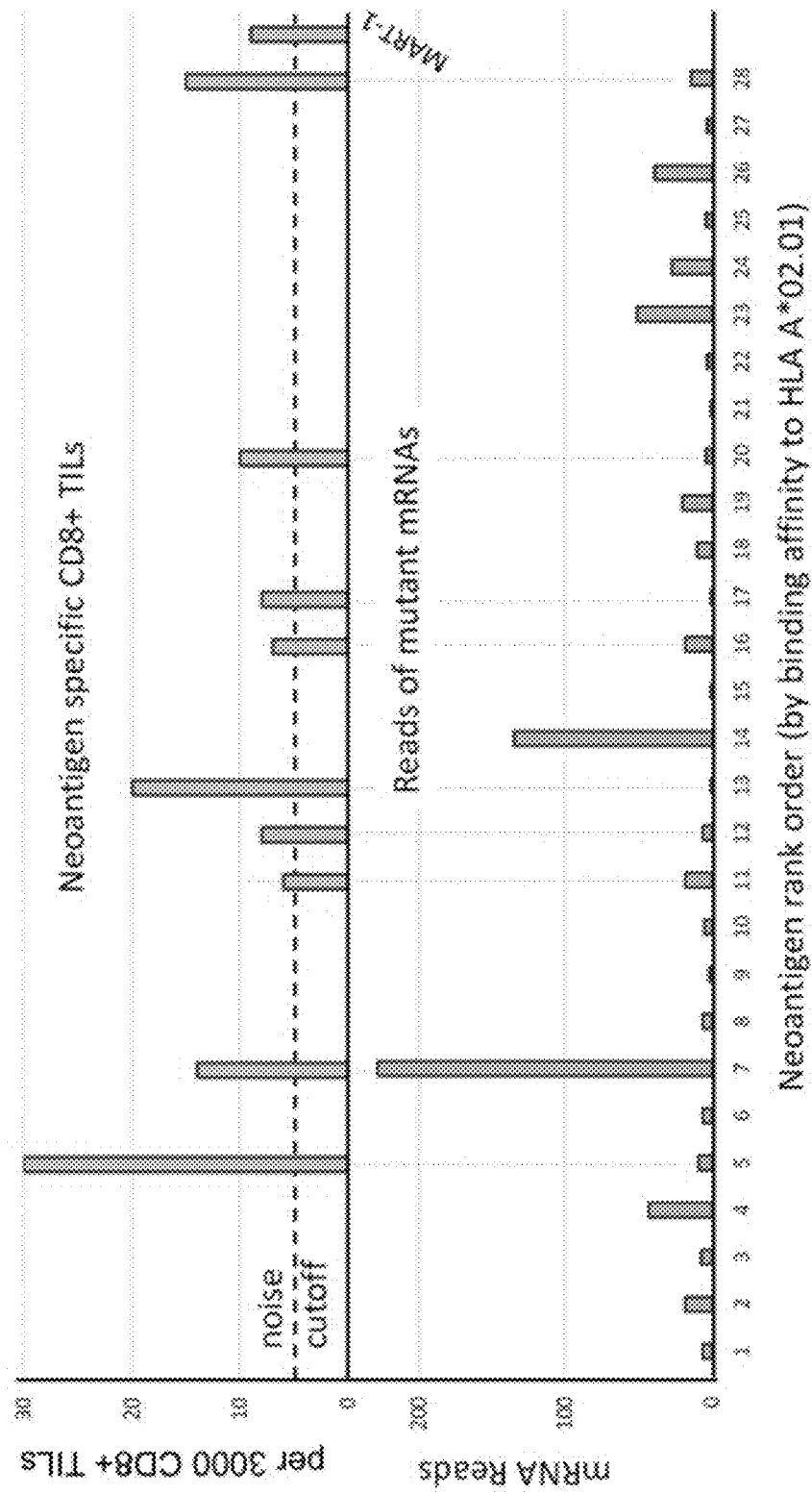
FIG. 16 shows graphical analysis of patient #2 TILs (upper graph with green bars) for neoantigen-specific CD8+ T cell populations using a NP-barcode NACS library based upon the top 28 putative neoantigens predicted for patient #2, plus the MART-1 tumor antigen in which only the T cell populations detected at more than 5 cells per 3000 TILs were considered statistically significant, and the bottom graph (gray bars) shows the mRNA copies measured for the mutated proteins from which the neoantigens were derived, according to embodiments of the present invention.

Screening the Barcoded NP-Antigen-MHC Complex Library in PBMCs Some biospecimens were analyzed using a serial approach, in which each NP-barcoded NACS library element was used to query for a specific T cell population. This method is most useful for analysis of PBMCs, where neoantigen-specific T cell populations particularly rare scarce, and it can be challenging to remove all of the unbound magnetic NPs, which can interfere with the fluorescence read-out. To characterize the non-specific pulldown rate of this approach, the NP-barcoded NACS library designed for patient #1 was used to analyze expanded TILs from an additional unrelated melanoma patient on the same clinical trial, as well as PBMCs from a healthy volunteer. The list of neoantigens is unique for every patient, and so the library designed for patient #1 should not capture T cell populations for the two control patient samples. The results for both controls were similar: The patient #1 neo-antigen library captured on average 2 cells per library element, with a standard deviation of 1.4 as shown in FIG. 15. Accordingly, a noise level was set at 5 cells (2 standard deviations above the mean). In the analysis of the two controls, no library element captured more than 5 cells, and there was no correlation between the controls (FIG. 15), indicating that none of the patient #1 library elements are intrinsically low-selectivity. Using the 5-cell cut-off the NP-barcoded NACS library for patient #2, serial analysis of that patient's TILs yielded a similar number of neoantigen-specific T cell populations as were found for the corresponding analysis of patient #1's TILs as shown in FIG. 16.

Example 4

Figure 17:
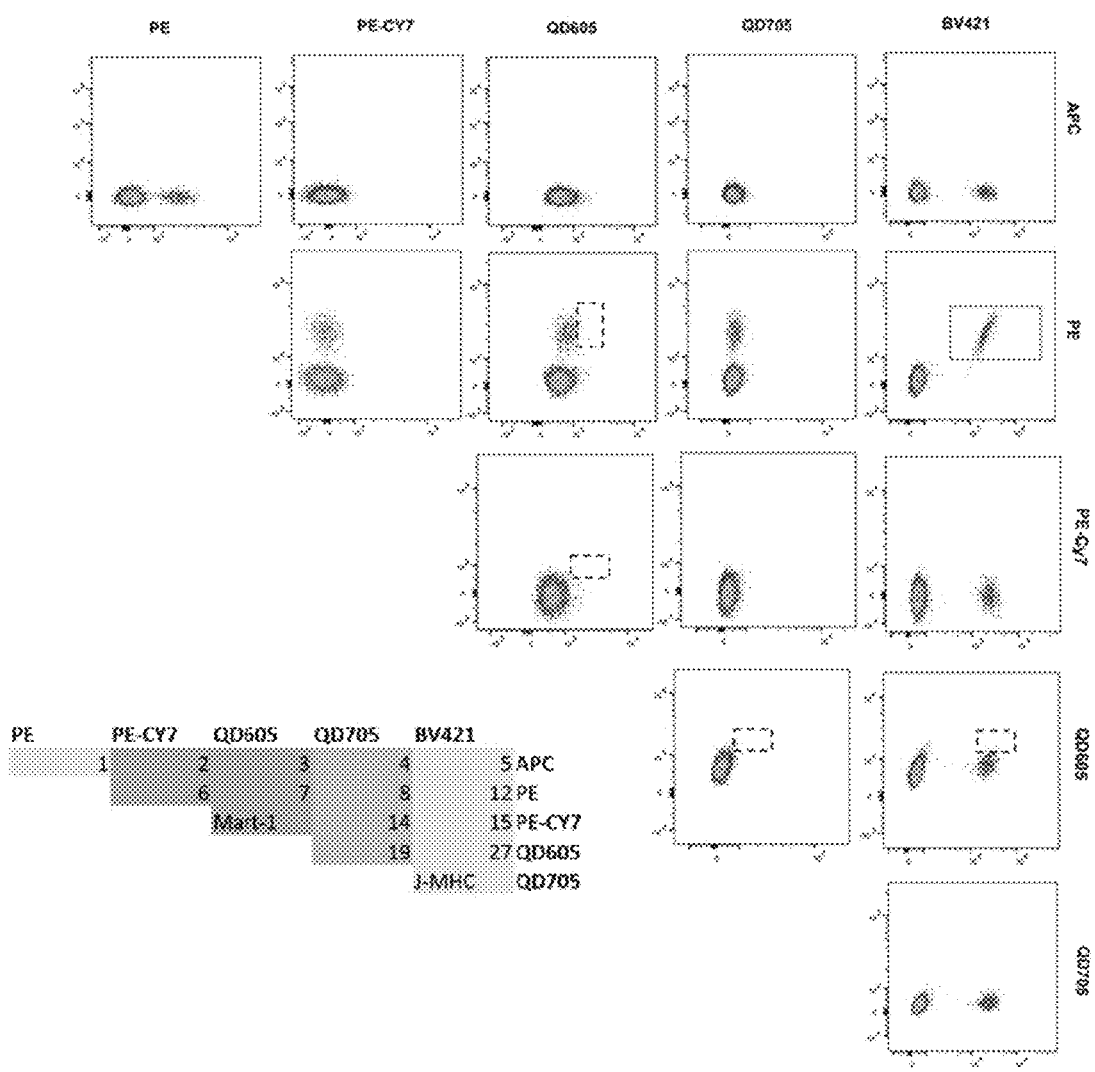
FIG. 17 shows data from a multiplex flow analysis of patient #1 TILs in which the T cells are stained with fluorescent-streptavidin conjugated neo-antigen multimers, with two-color barcodes as indicated in the legend, with the flow data positively confirming that neoantigen #12, is in only two colors in >10 cells, and that with this multiplex method, other neo-antigens, such as #7, Mart-1, #19 and #27 (dashed boxes), were ambiguous, due to the fact that the flow data cannot resolve individual cells.

Comparison with Multiplex Flow Analysis. The analysis of both patient's TILs revealed a larger number neoantigen-specific T cell populations than have been reported using multiplex flow analysis of similar patient samples. The expanded patient #1 TILs was analyzed using the multiplex flow method as described in Andersen et al., 2012, *Nat. Protocols,* 7:891-902, the entire contents of which are herein incorporated by reference. For this analysis, a 14-element tetramer library was prepared presenting putative neoantigens 1-8, 12, 14, 15, 19, 27 and Mart-1 (8 of which were detected using NP-barcoded NACS). Only T cells specific to neoantigen #12 were detected in only two colors and in >10 cells (FIG. 17). This was the most abundant population from TILs analyzed by the NP-barcoded NACS method. However, the results for other neo-antigens, such as #7, #19, #27 and Mart-1, are ambiguous, due to the fact that the flow data cannot resolve individual cells which is now possible with the NP-NACS technology according to embodiments of the present invention.

Example 5

Figure 18:
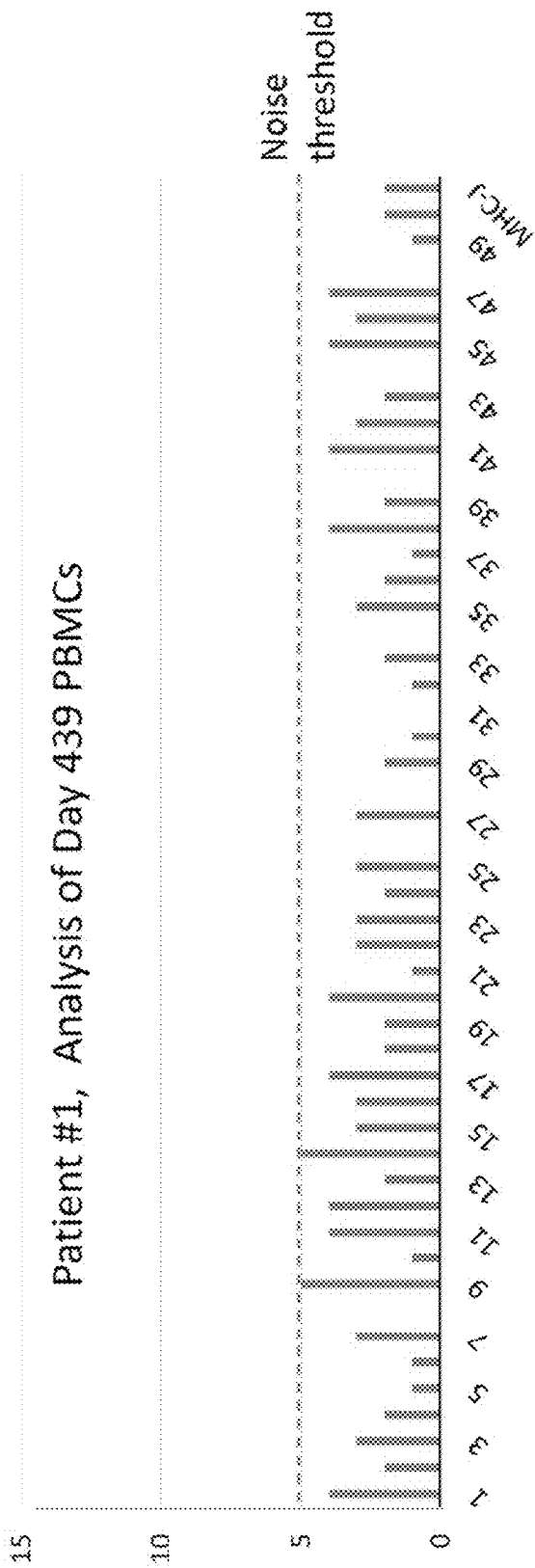
FIG. 18 is a graph showing the number of T cells analyzed in Patient #1 PBMCs using the Patient #1 specific barcoded NP-antigen-MHC library screened with a blood draw collected 439 days following the start of anti-PD-1 therapy, in which no T cell populations were isolated above two standard deviations of the mean (2.2±1.4 cells per library element) were recorded, according to embodiments of the present invention.

Analysis with PMBCs from Patient #1. The Sensitivity of the NP-Barcoded NACS method prompted analysis of peripheral blood from patient #1 for neoantigen-specific T cell populations. These T cells were not expanded in vitro, so as to avoid any population bias that can accompany such expansion. For the blood analysis, the full 50-element neoantigen library was used to interrogate PBMCs collected at four time points. Two time points (Days 187 and 208, FIG. 11) were collected during response to therapy while tumors were shrinking, and corresponded closely to the date of the tumor biopsy (Day 187) from which the TILs were collected. For those 2 PBMC samples, the neoantigen-specific T cell levels were below those found in the TILs (1% vs 7% of all CD8+ T cells), but several populations at levels >0.05% were positively detected. Most populations coincided with those detected from the TILs, with two new populations (specific to neoantigens #15 and #33) identified. Analysis of PBMCs at Day 439 detected zero neoantigen-specific populations as shown in FIG. 18.

Day 41 PBMCs correspond to a time close to the biopsy from which the exome and transcriptome measurements were taken, but also during a period of pseudo-progression for patient #1 prior to response (FIG. 11). T cells were observed at this early time point, and those populations were present in substantially higher numbers (about 2% of CD8+ PBMCs) relative to later time points when the tumors were regressing. The same populations detected at Days 187 and 208 were also detected at Day 41, as well as additional populations.

Several of the detected neoantigen-specific T cell populations from PBMCs correspond to relatively weak (Kd>100 nM) neoantigen/MHC binding affinities. The number of mutation-containing reads from the mRNAs associated with the mutated proteins from the pre-treatment transcriptome analysis are provided in the bottom graph of FIG. 14. There is a striking correspondence between the appearance of T cell populations specific to the weaker binding neoantigens, and the expression levels of the corresponding mutated proteins. For example, 8 of the top 12 neoantigens, as ranked by mRNA expression level, were detected (Table 3). Further, for the 10 neoantigens in the panel for which corresponding mRNA levels were measured to be zero, only the strong binding neoantigen #5 was associated with any detected populations (TILs and Day 41 PBMCs).

Example 6

Captured T cells are Not Destroyed. An advantage to the NP-barcoded NACS method is that the process is non-destructive and single T-cells, now with known antigen-specificity, are individually isolated by the microfluidic device and available for further analysis, including TCR α and β gene sequencing. To this end, paired TCRα and TCRβ genes from a single T cell from patient #1 were cloned, both as proof of capability and validation of the barcoded neoantigen specificity. A CD8+ T cell was captured in the single microfluidic trapping device (FIGS. 19A, 19B) and barcoded to identify the neo-antigen identity (FIG. 20A). The captured single T cell was punched out to perform RT-PCR to obtain TCR α and β gene sequences. Jurkat cells transduced to express that TCR were found to bind to the cognate neoantigen tetramer (FIG. 20B).

Analysis of T cells collected from two tumors of immunotherapy patients responding to anti-PD1 therapy reveals that around 20% of the top 50 predicted neoantigens account for a large fraction (~7% for the HLA A*02.01) of CD8+ T cells in the tumor. The two patients analyzed here each express 6 HLA genotypes. Although the actual representation of additional HLA genotypes still needs to be tested, the implication is that 40% or more of the CD8+ TILs within these patient tumors are neoantigen specific. This number is significantly larger than would have been inferred using alternative analytic methods, and emphatically highlights the importance of neoantigen-specific T cell populations as major effectors in anti-PD-1 cancer immunotherapy. A second observation is that the measured spectrum of neoantigen-specific T cell populations only correlates loosely with the predicted rank-order of putative neoantigens. However, an additional correlation with mRNA expression levels was found, especially for the weaker binding neoantigens. A third observation is that the same neoantigen-specific populations detected in the tumor are also detected in the blood, albeit at a lower relative abundance to all CD8+ PBMCs. In the analysis reported here for patient #1, those populations are detected a full 2 months prior to traditional clinical measures (via in vivo imaging) of actual tumor shrinkage.

Example 7

Patients, Treatment, and Specimen Collection Patients with metastatic melanoma were selected for the current analysis by being HLA-A*02:01 positive, having an adequate baseline biopsy as well as an on-treatment biopsy, and exhibiting an objective tumor response while participating in a phase 1 trial of pembrolizumab. Patients #1 and #2 received single agent pembrolizumab intravenously 10 mg/kg every 3 weeks (10Q3W). Tumor responses were evaluated starting at 12 weeks, confirmed 4 weeks after first response, and imaged every 12 weeks thereafter. Response was characterized by both the Response Evaluation Criteria in Solid Tumors (RECIST) and the immune-related response criteria (irRC). Tumour biopsy and peripheral blood cell collection and analyses were approved by UCLA IRBs 11-001918 and 11-003066. Tumor biopsies from the patients analyzed were obtained at baseline and on therapy and were processed with one aliquot immediately fixed in formalin followed by paraffin embedding for pathological analyses, a second aliquot snap frozen by immediate immersion in liquid nitrogen for genetic analyses, and a third aliquot minced fresh under sterile condition followed by DNAse/collagenase digestion to create single cell suspensions (s.c.s) before cryopreservation in liquid nitrogen. Peripheral blood mononuclear cells (PBMCs) were prepared from fresh whole blood by Ficoll-Paque density gradient centrifugation and cryopreserved.

Example 8. TIL Isolation and Expansion

Tumor infiltrating lymphocytes were expanded from cryopreserved s.c.s using anti-CD3 antibody (OKT3, 50 ng/mL, 48 hr exposure) and IL-2 (300 IU/mL) and re-cyropreserved at 5×106 cells/mL after 2-4 weeks. TILs were thawed and treated with DNAse for 45 min the morning of use, and stained with antibodies to CD4 (BV510, BioLegend, San Diego, Calif.) and CD8+ (BV605, BioLegend, San Diego, Calif.). Live (7AAD-negative) populations of CD4 and CD8+ single-positive cells were sorted using a FACS Cell Sorter (BD Biosciences, San Jose, Calif.).

Example 9

Whole Exome Sequencing (WES), Mutation Calling and HLA-Typing Both DNA and RNA were extracted simultaneously from snap-frozen tumor biopsies (Qiagen AllPrep Kit). DNA from tumors and matched normal blood samples were sequenced at the UCLA Clinical Microarray Core. Paired-end 2×100 bp sequencing was carried out on the Hi Seq 2000 platform (Illumina, San Diego, Calif.) following exon capture using the Nimblegen SeqCap EZ Human Exome Library v3.0 (Roche), which targets 65 Mb of genome. Sequencing generated 6-10 billion reads per sample, with each targeted base covered by an average of 90-150 reads. Sequences were aligned to the UCSC hg19 human genome reference using BWA-mem algorithm (v0.7.9). Preprocessing followed the GATK Best Practices Workflow v3, including duplicate removal (Picard Tools), indel realignment, and base quality score recalibration. Somatic mutations were called with methods modified from 1, using MuTect (v1.1.7)2, Varscan2 Somatic (v2.3.6)3, and the GATK-HaplotypeCaller (HC, v3.3). Only high-confidence mutations were retained, defined as those identified by at least two out of three programs. For the GATK-HC, somatic variants were determined using one-sided Fisher's Exact Test (P value cut-off ≤0.01) between tumor/normal pairs. Variants were annotated by Oncotator4, with non-synonymous mutations being those classified as Nonsense, Missense, Splice_Site, or Nonstop Mutations, as well as Frame_Shift, In_Frame, or Start_Codon altering insertions/deletions. HLA-typing was performed by ATHLATES from the whole exome sequencing data.

Example 10. RNA Sequencing

RNA sequencing was performed using the Illumina HiSeq 2500 platform on 100-bp paired-end libraries prepared using the IlluminaTruSeq RNA sample preparation kit per the manufacturer's instructions. Reads were mapped to hg19 using TopHat2 v2.0,5 and were quantified and normalized using Cufflinks v2.2.16 program and CuffNorm to generate normalized expression tables by library size (fragments per kilobase of exon per million fragments mapped, FPKM) using the geometric normalization method. Mutation-containing RNA reads were identified by a custom Python (v2.7.3) script utilizing the Biopython and pysam packages, and verified by visual inspection in the Integrated Genomics Viewer (IGV).

Example 11

Peptide HLA Binding Prediction and Neoantigen Candidate Identification Peptide binding predictions to HLA-A02:01 were generated by netMHC3.47 for 9-mer and 10-mer peptides in a sliding window around each non-synonymous amino acid-altering mutation. (Peptide sequences were derived from Ensembl GRCh37 release 74.) Candidate peptides were binned by 1) those with mutations-containing reads identified by RNA-seq, 2) those with RNA expression (FPKM>0) but no identified mutated reads, and 3) all others without detectable RNA-seq expression. Peptides were ranked and sorted by HLA binding affinity within each bin.

Example 12. Production of ssDNA-SAC Conjugates

The ssDNA-SAC (strepatavidin antigen complex) conjugate was produced following previous published protocol as described in Kwong et al., 2009, *J. Am. Chem Soc.,* 131: 9695-9703, the entire contents of which are herein incorporated by reference. Briefly, SAC was first expressed from the pTSA-C plasmid containing the SAC gene (Addgene), as described in Sano et al., 1990, *PNAS,* 87:142-146, the entire content of which is herein incorporated by reference. Before conjugation to DNA, SAC (1 mg/ml) was buffer exchanged to PBS containing Tris(2-Carboxyethyl) phosphine Hydrochloride (TCEP, 5 mM) using zeba desalting columns (Pierce). Then MHPH (3-N-Maleimido-6-hydraziniumpyridine hydrochloride, 100 mM, Solulink) in DMF was added to SAC at a molar excess of 300:1. In the meantime, SFB (succinimidyl 4-formylbenzoate, 100 mM, Solulink) in DMF was added to 5'-amine modified ssDNA (500 uM) (5'-$NH_2$-AAA AAA AAA A TAG GCA TCC CGA GGA TTC AG (SEQ ID NO: 157)) in a 40:1 molar ratio. After reacting at rt for 4 hours, MHPH-labeled SAC and SFB-labeled DNA were buffer exchanged to citrated (50 mM sodium citrate, 150 mM NaCl, pH 6.0), and then mixed in a 20:1 ratio of DNA to SAC to react at rt overnight. DNA-SAC conjugate was purified using the Superdex 200 gel filtration column (GE health) and concentrated with 10K MWCO ultra-centrifuge filters (Millipore).

Example 13. Human MHC Class I Neo-Antigen Library Construction

MHC library was generated using the UV-mediated peptide exchange method as described in Rodenko et al., 2006, *Nat. Protoc.* 1:1120-1132, the entire content of which is herein incorporated by reference. The photo-labile peptide KILGFVFJV (SEQ ID NO: 158) and other neo-antigen peptides were synthesized with standard automated Fmoc-peptide synthesis methodology (J, (S)-3-(Fmoc-amino)-3-(2-nitrophenyl)propionic acid, is the photo-labile amino acid residue). Plasmids encoding human MHC class I heavy chain and human b2m containing bacterial strain were kind gifts from Ton N M Schumacher. MHC photo-labile protein was folded from MHC heavy chain inclusion body, b2m inclusion body and photo-labile peptide according to the previously published protocol 11 and then biotinylated using the BirA biotin ligase. Mixture of MHC photo-labile protein (0.5 uM) and neo-antigen peptide (50 uM) was exposed to 365 nm UV light for 1 hour to generate the MHC neo-antigen library.

Example 14

NP MHC Neo-Antigen Library Construction Streptavidin magnetic NP (1 um, ThermoFisher scientific) was mixed with biotin-DNA at 1:20 ratio to obtain NP-DNA. Excess DNA was removed by washing the magnetic NP for 3 times. In parallel, MHC neo-antigen library was added to ssDNA-SAC at 4:1 ratio to form the DNA-MHC tetramer. Equal amount (in terms of DNA ratio) of NP-DNA and DNA-MHC tetramer were hybridized at 37° C. for 30 min to generate the NP MHC neo-antigen library.

Example 15. Cell-Trapping Microfluidic Device Fabrication

First, a master mold with cell traps (multiple traps or single traps) was prepared using the SU-8 2025 photoresist. Sylgard 184 (A:B=10:1) mixture was then poured onto the mold, degassed and cured at 80° C. for 2 hours. In the meantime, a thin layer of PDMS was spun coated onto a glass slide at 2000 rpm/min and cured at 80° C. for 1 hour. The PDMS device and PDMS-coated glass were treated with O2 plasma for 1 min and bound together to get the final cell-trapping microfluidic device.

Example 16. TIL Pulldown and Barcode

NP MHC neo-antigen library was added to CD8+ human T cells for 30 min at rt. The NP-bound T cells were magnetically enriched and washed with PBS to remove any non-specifically pulled T cells. The cells were then loaded into costar transwell polycarbonate membrane (5 um pore) to remove free NPs. Then, the cells were loaded into the cell-trapping microfluidic device and sequentially barcoded. First, 3 different DNA-dyes (cy3, cy5 and Alex 488) were loaded to the device to hybridize with the DNA on the NP at 37° C. for 15 min. After a brief washing, fluorescent images were taken to obtain the first round barcode. Displacement DNAs were added to the device at 37° C. for 15 min to remove the first round DNA dyes. Similar procedures were employed to obtain the second and third round barcoding images.

Example 17. CD8+ T Cell Pulldown from PBMC

CD8+ T cells from PBMC were sorted by FACS. CD8+ T cells were then (10K) stained with Calcein AM (Thermo-Fisher) and incubated with each individual NP-NACS library at rt for 30 min. Neo-antigen specific cells were enriched by magnet pulldown. The non-captured T cells in the supernatant was collected for further incubation with other NP-NACS library element. The enriched T cells were washed by PBS once to remove any non-specific cell pulldown. Cells were then loaded into the cell hemocytometer. The whole area in the hemocytometer chip was imaged to obtain the total pulldown cell number. Healthy donor PBMC and PBMC from an unrelated male melanoma patient were used as control to obtain the background.

Example 18. Single Cell TCR Cloning

Figure 19A:
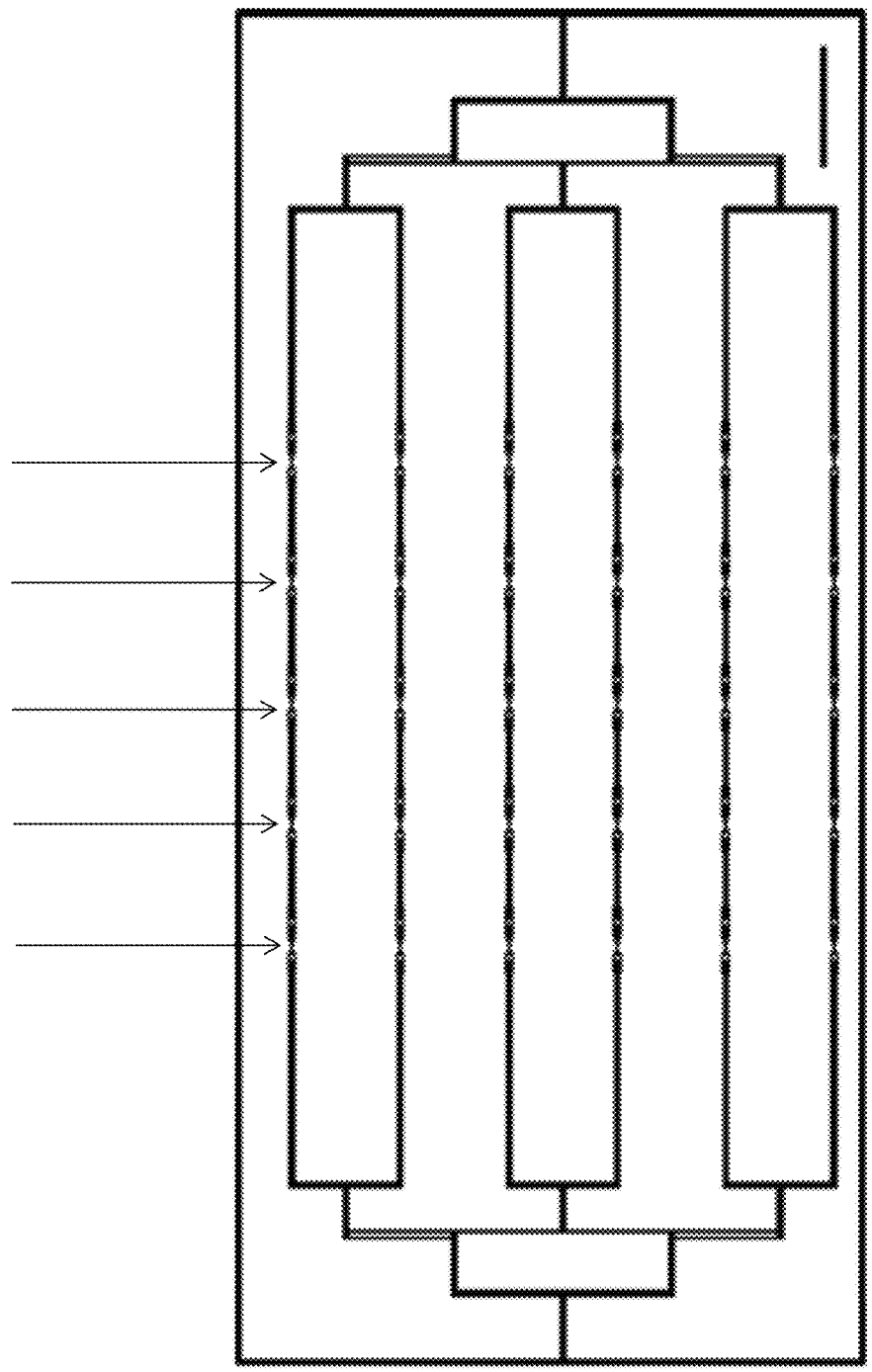
FIG. 19A is a schematic illustration of a single cell trap device with single cell traps designed to be 2 mm apart from each other (indicated in the top channel with black arrows), allowing for the isolation of specific trapped cells by 1 mm cell puncher without disturbing other trapped cells with a scale bar showing 2 mm, according to embodiments of the present invention.
Figure 19B:
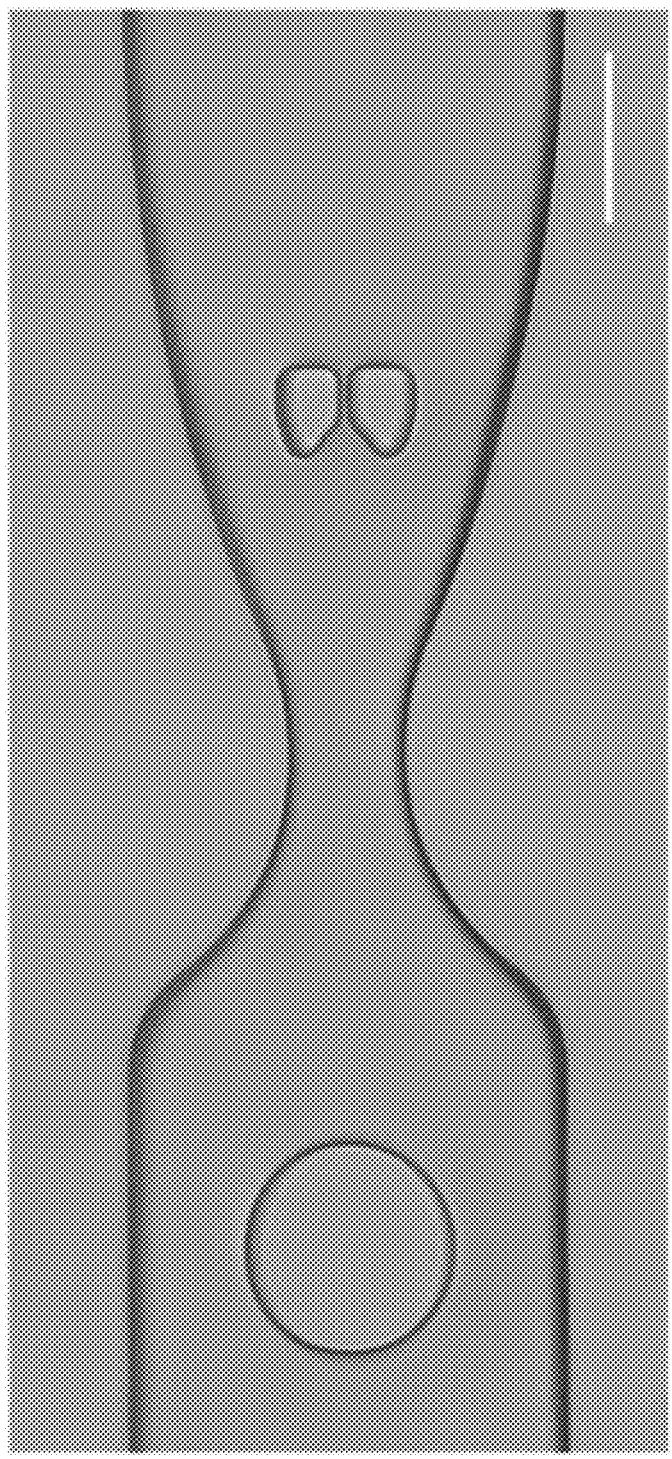
FIG. 19B is a microscope image of a single cell trap with a scale bar showing 50 um, according to embodiments of the present invention.
Figure 20A:
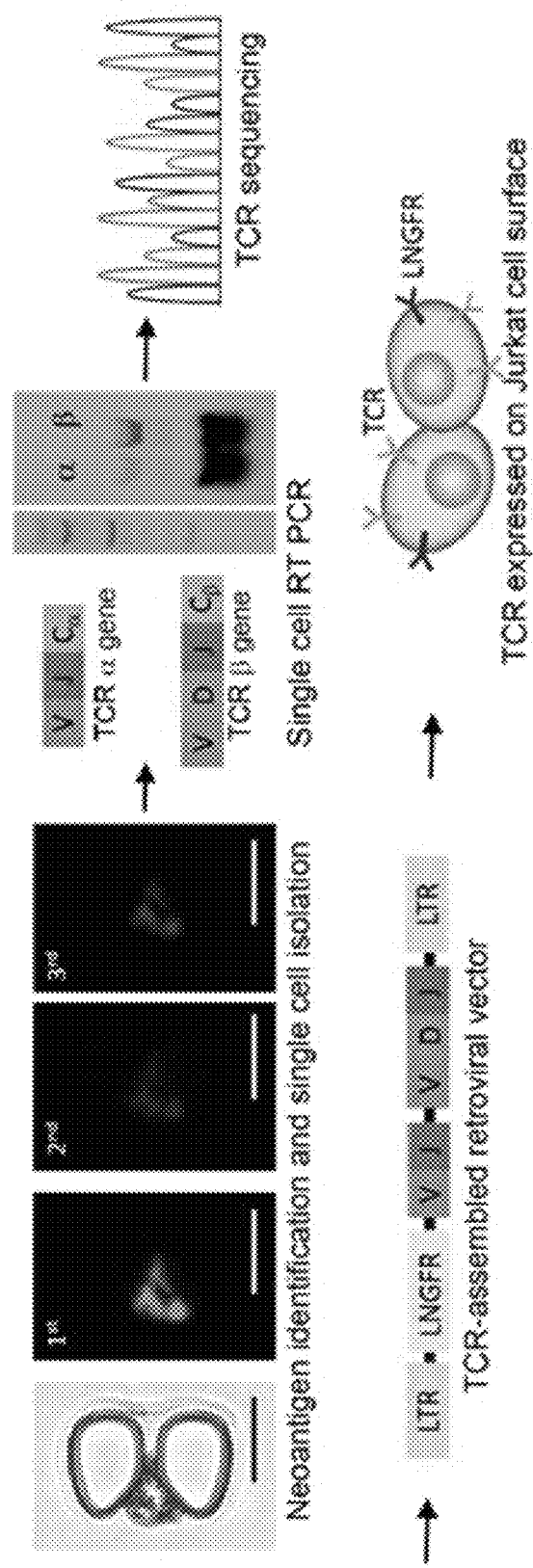
FIG. 20A depicts optical micrographs showing (left to right) a captured barcoded T cell from patient #1, followed by the 3 sequential fluorescent readout steps (yellow, red, and green, respectively) to identify specificity against neoantigen #12, with scale bars at 20 um; with the captured single T cell subsequently punched out to perform RT-PCR to obtain TCRα and TCRβ gene sequences (DNA ladder: 100 bp), and the obtained TCR gene was then assembled and transferred into a retroviral vector (schematic shown) and delivered into Jurkat T cells (schematically shown in green) for analysis by flow cytometry, according to embodiments of the present invention.
Figure 20B:
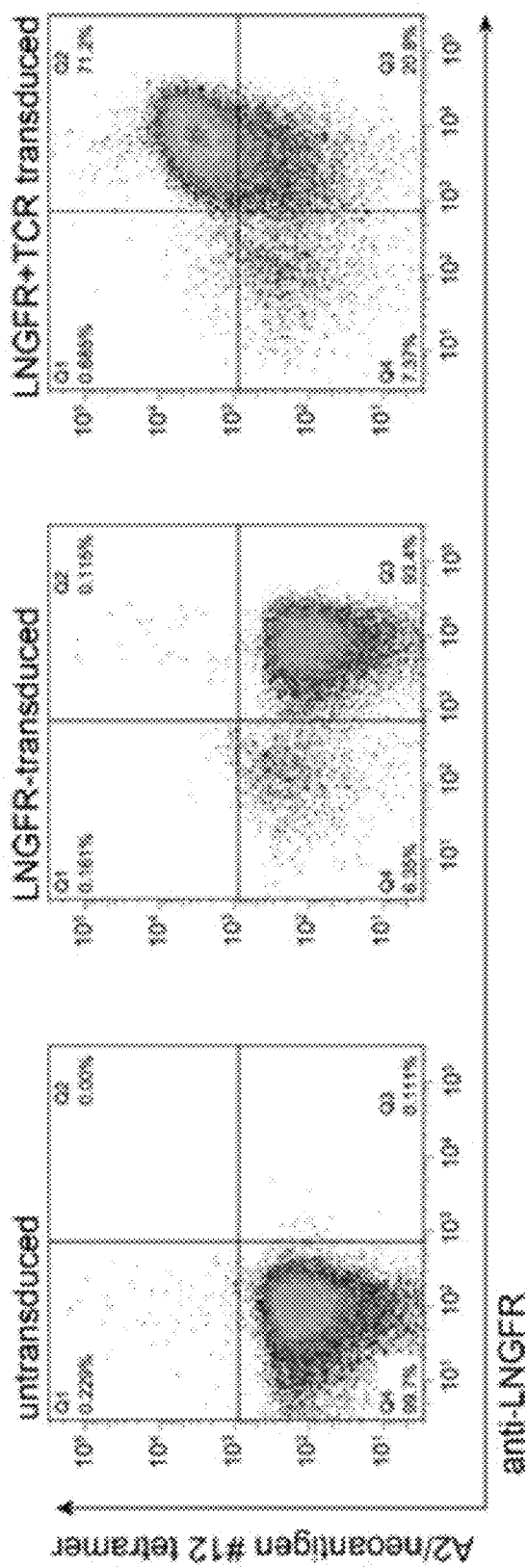
FIG. 20B shows the flow cytometry results for untransduced Jurkat cells (left), Jurkat cells transduced with LNGFR expression reporter (center) and Jurkat cells transduced with both NGFR and the TCR specific for neo-antigen 12 (right), according to embodiments of the present invention.

Neo-antigen specific T cells were trapped in the microfluidic device with single cell traps (FIGS. 19A-19B). The cells were then recovered by PDMS puncher. Brief sonication was applied to release the cell from the punched-out PDMS to cell lysis buffer (10 mM Tris, pH=8, with 1 U/ul RNAse inhibitor, Promega). Rearranged Vα and Vβ domain genes were cloned from single cells using a OneStep RT PCR kit (Qiagen) with multiplexed forward primers that bind TRAV and TRBV gene segments (Tables 5-6) and reverse primers that bind the constant Cα (5'-GCCACAG-CACTGTTGCTCTTGAAGTCC-3' (SEQ ID NO: 159)) and Cβ (5'-CCACCAGCTCAGCTCCACGTG-3' (SEQ ID NO: 160)) domain genes. cDNA products were used as templates in a second semi-nested amplification with a universal set of primers (alpha forward primer: 5'-TGGCCTGCTTTGTTT-GCCGTGGTTACAGGAAGCCTCAGCA-3' (SEQ ID NO: 161), alpha reverse primer: 5'-GCCACAGCACTGTT-GCTCTTGAAGTCCATAG-3' (SEQ ID NO: 162); beta forward primer: 5'-CGGGCTCCTTTGCCTACCGTGCCT-GCAGGAGGGCTCGGCA-3' (SEQ ID NO: 163), beta reverse primer: 5'-CGTGCTGACCCCACTGTGCACCTC-CTTCCCATTCACCCACCAGCTCAGCTCCACGTGGT C-3' (SEQ ID NO: 164)). Vα and Vβ cDNA were sequenced and reamplified using single TRAV/TRBV forward primers to correct mispriming artifacts introduced through multiplexed PCR. Retroviral vectors were constructed for functional testing through PCR assembly. The Vα and Vβ domain genes were assembled with human growth hormone (HGH) signal peptides, constant regions of the TCRα and TCRβ chains, and a 2A ribosomal skipping sequence, then digested with restriction enzymes and ligated into a MSCV-based non-replicative retroviral backbone.

TABLE 5 single cell TCRα cloning primers
Vα-gene-specific primers for cloning TCRα genes

| TRAV gene | Signal peptide sequence | TRAV gene-specific sequence | SEQ ID NO: |
|---|---|---|---|
| TRAV1-1*01 | 5'-TACAGGAAGCCTCAGCA | GGACAAAGCCTTGAGCAGCCCTC-3 | 165 |
| TRAV1-2*01 | 5'-TACAGGAAGCCTCAGCA | GGACAAAACATTGACCAGCCCACTG-3' | 166 |
| TRAV2*01 | 5'-TACAGGAAGCCTCAGCA | AAGGACCAAGTG1TTCAGCCTTCCAC-3' | 167 |
| TRAV3*01 | 5'-TACAGGAAGCCTCAGCA | GCTCAGTCAGTGGCTCAGCCGGA-3' | 168 |
| TRAV4*01 | 5'-TACAGGAAGCCTCAGCA | CTTGCTAAGACCACCCAGCCCATC-3' | 169 |
| TRAV5*01 | 5'-TACAGGAAGCCTCAGCA | GGAGAGGATGTGGAGCAGAGTCTTTTCC-3' | 170 |
| TRAV6*01 | 5'-TACAGGAAGCCTCAGCA | AGCCAAAAGATAGAACAGAATTCCGAGGC-3' | 171 |
| TRAV6*03 | 5'-TACAGGAAGCCTCAGCA | GAGGCCCTGAACATTCAGGAGGG-3' | 172 |
| TRAV7*01 | 5'-TACAGGAAGCCTCAGCA | GAAAACCAGGTGGAGCACAGCCC-3' | 173 |
| TRAV8-1*01 | 5'-TACAGGAAGCCTCAGCA | GCCCAGTCTGTGAGCCAGCATAACC-3' | 174 |

TABLE 5-continued single cell TCRα cloning primers
Vα-gene-specific primers for cloning TCRα genes

| TRAV gene | Signal peptide sequence | TRAV gene-specific sequence | SEQ ID NO: |
|---|---|---|---|
| TRAV8-2*01 | 5'-TACAGGAAGCCTCAGCA | GCCCAGTCGGTGACCCAGCTTG-3' | 175 |
| TRAV8-2*02 | 5'-TACAGGAAGCCTCAGCA | GCCCAGTCGGTGACCCAGCTTAG-3' | 176 |
| TRAV8-3*01 | 5'-TACAGGAAGCCTCAGCA | GCCCAGTCAGTGACCCAGCCTG-3' | 177 |
| TRAV8-4*06 | 5'-TACAGGAAGCCTCAGCA | CTCTTCTGGTATGTGCAATACCCCAACC-3' | 178 |
| TRAV8-4*07 | 5'-TACAGGAAGCCTCAGCA | GTTGAACCATATCTCTTCTGGTATGTGCAATACC-3' | 179 |
| TRAV8-6*01 | 5'-TACAGGAAGCCTCAGCA | GCCCAGTCTGTGACCCAGCTTGAC-3' | 180 |
| TRAV8-7*01 | 5'-TACAGGAAGCCTCAGCA | ACCCAGTCGGTGACCCAGCTTG-3 | 181 |
| TRAV9-1*01 | 5'-TACAGGAAGCCTCAGCA | GGAGATTCAGTGGTCCAGACAGAAGGC-3' | 182 |
| TRAV9-2*01 | 5'-TACAGGAAGCCTCAGCA | GGAAATTCAGTGACCCAGATGGAAGG-3' | 183 |
| TRAV9-2*02 | 5'-TACAGGAAGCCTCAGCA | GGAGATTCAGTGACCCAGATGGAAGG-3' | 184 |
| TRAV10*01 | 5'-TACAGGAAGCCTCAGCA | AAAAACCAAGTGGAGCAGAGTCCTCAGTC-3' | 185 |
| TRAV11*01 | 5'-TACAGGAAGCCTCAGCA | CTACATACACTGGAGCAGAGTCCTTCATTCC-3' | 186 |
| TRAV12-1*01 | 5'-TACAGGAAGCCTCAGCA | CGGAAGGAGGTGGAGCAGGATCC-3' | 187 |
| TRAV12-2*01 | 5'-TACAGGAAGCCTCAGCA | CAGAAGGAGGTGGAGCAGAATTCTGG-3' | 188 |
| TRAV12-2*03 | 5'-TACAGGAAGCCTCAGCA | GGACCCCTCAGTGTTCCAGAGGG-3' | 189 |
| TRAV12-3*01 | 5'-TACAGGAAGCCTCAGCA | CAGAAGGAGGTGGAGCAGGATCCTG-3' | 190 |
| TRAV13-1*02 | 5'-TACAGGAAGCCTCAGCA | GGAGAGAATGTGGAGCAGCATCCTTC-3' | 191 |
| TRAV13-2*01 | 5'-TACAGGAAGCCTCAGCA | GGAGAGAGTGTGGGGCTGCATCTTC-3' | 192 |
| TRAV14/DV4*01 | 5'-TACAGGAAGCCTCAGCA | GCCCAGAAGATAACTCAAACCCAACCAG-3' | 193 |
| TRAV14/DV4*04 | 5'-TACAGGAAGCCTCAGCA | CAGAAGATAACTCAAACCCAACCAGGAATG-3' | 194 |
| TRAV16*01 | 5'-TACAGGAAGCCTCAGCA | GCCCAGAGAGTGACTCAGCCCGA-3' | 195 |
| TRAV17*01 | 5'-TACAGGAAGCCTCAGCA | AGTCAACAGGGAGAAGAGGATCCTCAGG-3' | 196 |
| TRAV18*01 | 5'-TACAGGAAGCCTCAGCA | GGAGACTCGGTTACCCAGACAGAAGG-3' | 197 |
| TRAV19*01 | 5'-TACAGGAAGCCTCAGCA | GCTCAGAAGGTAACTCAAGCGCAGACTG-3' | 198 |
| TRAV20*01 | 5'-TACAGGAAGCCTCAGCA | GAAGACCAGGTGACGCAGAGTCCC-3' | 199 |
| TRAV21*01 | 5'-TACAGGAAGCCTCAGCA | AAACAGGAGGTGACGCAGATTCCTGC-3' | 200 |
| TRAV22*01 | 5'-TACAGGAAGCCTCAGCA | GGAATACAAGTGGAGCAGAGTCCTCCAG-3' | 201 |
| TRAV23/DV6*01 | 5'-TACAGGAAGCCTCAGCA | CAGCAGCAGGTGAAACAAAGTCCTCA-3' | 202 |
| TRAV23/DV6*04 | 5'-TACAGGAAGCCTCAGCA | CAGCAGGTGAAACAAAGTCCTCAATCTTTG-3' | 203 |
| TRAV24*01 | 5'-TACAGGAAGCCTCAGCA | ATACTGAACGTGGAACAAAGTCCTCAGTCAC-3' | 204 |
| TRAV25*01 | 5'-TACAGGAAGCCTCAGCA | GGACAACAGGTAATGCAAATTCCTCAGTACC-3' | 205 |
| TRAV26-1*01 | 5'-TACAGGAAGCCTCAGCA | GATGCTAAGACCACCCAGCCCCC-3' | 206 |
| TRAV26-1*02 | 5'-TACAGGAAGCCTCAGCA | GATGCTAAGACCACCCAGCCCACC-3' | 207 |
| TRAV26-2*01 | 5'-TACAGGAAGCCTCAGCA | GATGCTAAGACCACACAGCCAAATTCAATG-3' | 208 |
| TRAV27*01 | 5'-TACAGGAAGCCTCAGCA | ACCCAGCTGCTGGAGCAGAGCC-3' | 209 |
| TRAV29/DV5*01 | 5'-TACAGGAAGCCTCAGCA | GACCAGCAAGTTAAGCAAAATTCACCATC-3' | 210 |
| TRAV30*01 | 5'-TACAGGAAGCCTCAGCA | CAACAACCAGTGCAGAGTCCTCAAGC-3' | 211 |

TABLE 5-continued single cell TCRα cloning primers
Vα-gene-specific primers for cloning TCRα genes

| TRAV gene | Signal peptide sequence | TRAV gene-specific sequence | SEQ ID NO: |
|---|---|---|---|
| TRAV34*01 | 5'-TACAGGAAGCCTCAGCA | AGCCAAGAACTGGAGCAGAGTCCTCAG-3' | 212 |
| TRAV35*01 | 5'-TACAGGAAGCCTCAGCA | GGTCAACAGCTGAATCAGAGTCCTCAATC-3' | 213 |
| TRAV36/DV7*01 | 5'-TACAGGAAGCCTCAGCA | GAAGACAAGGTGGTACAAAGCCCTCTATCTC-3' | 214 |
| TRAV36/DV7*02 | 5'-TACAGGAAGCCTCAGCA | GAAGACAAGGTGGTACAAAGCCCTCAATC-3' | 215 |
| TRAV38-1*01 | 5'-TACAGGAAGCCTCAGCA | GCCCAGACAGTCACTCAGTCTCAACCAG-3' | 216 |
| TRAV38-1*04 | 5'-TACAGGAAGCCTCAGCA | GCCCAGACAGTCACTCAGTCCCAGC-3' | 217 |
| TRAV38-2/DV8*01 | 5'-TACAGGAAGCCTCAGCA | GCTCAGACAGTCACTCAGTCTCAACCAGAG-3' | 218 |
| TRAV39*01 | 5'-TACAGGAAGCCTCAGCA | GAGCTGAAAGTGGAACAAAACCCTCTGTTC-3' | 219 |
| TRAV40*01 | 5'-TACAGGAAGCCTCAGCA | AGCAATTCAGTCAAGCAGACGGGC-3' | 220 |
| TRAV41*01 | 5'-TACAGGAAGCCTCAGCA | AAAAATGAAGTGGAGCAGAGTCCTCAGAAC-3' | 221 |

TABLE 6 single cell TCRβ cloning primers.
Vβ-gene-specific primers for cloning TCRα genes

| TRBV gene | Signal peptide sequence | TRBV gene-specific sequence | SEQ ID NO: |
|---|---|---|---|
| TRBV1*01 | 5'-CAGGAGGGCTCGGCA | GATACTGGAATTACCCAGACACCAAAATACCTG-3 | 222 |
| TRBV2*01 | 5'-CAGGAGGGCTCGGCA | GAACCTGAAGTCACCCAGACTCCCAG-3' | 223 |
| TRBV3-1*01 | 5'-CAGGAGGGCTCGGCA | GACACAGCTGTTTCCCAGACTCCAAAATAC-3' | 224 |
| TRBV3-2*01 | 5'-CAGGAGGGCTCGGCA | GACACAGCCGTTTCCCAGACTCCA-3' | 225 |
| TRBV4-1*01 | 5'-CAGGAGGGCTCGGCA | GACACTGAAGTTACCCAGACACCAAAACAC-3' | 226 |
| TRBV4-1*02 | 5'-CAGGAGGGCTCGGCA | CACCTGGTCATGGGAATGACAAATAAGAAG-3' | 227 |
| TRBV4-2*01 | 5'-CAGGAGGGCTCGGCA | GAAACGGGAGTTACGCAGACACCAAG-3' | 228 |
| TRBV4-3*04 | 5'-CAGGAGGGCTCGGCA | AAGAAGTCTTTGAAATGTGAACAACATCTGGG-3' | 229 |
| TRBV5-1*01 | 5'-CAGGAGGGCTCGGCA | AAGGCTGGAGTCACTCAAACTCCAAGATATC-3' | 230 |
| TRBV5-1*02 | 5'-CAGGAGGGCTCGGCA | AGGGCTGGGGTCACTCAAACTCC-3' | 231 |
| TRBV5-3*01 | 5'-CAGGAGGGCTCGGCA | GAGGCTGGAGTCACCCAAAGTCCC-3' | 232 |
| TRBV5-4*01 | 5'-CAGGAGGGCTCGGCA | GAGACTGGAGTCACCCAAAGTCCCAC-3' | 233 |
| TRBV5-4*03 | 5'-CAGGAGGGCTCGGCA | CAGCAAGTGACACTGAGATGCTCTTCTCAG-3' | 234 |
| TRBV5-4*04 | 5'-CAGGAGGGCTCGGCA | ACTGTGTCCTGGTACCAACAGGCCCT-3' | 235 |
| TRBV5-5*01 | 5'-CAGGAGGGCTCGGCA | GACGCTGGAGTCACCCAAAGTCC-3' | 236 |
| TRBV5-8*01 | 5'-CAGGAGGGCTCGGCA | GAGGCTGGAGTCACACAAAGTCCCAC-3' | 237 |
| TRBV5-8*02 | 5'-CAGGAGGGCTCGGCA | AGGACAGCAAGCGACTCTGAGATGC-3' | 238 |
| TRBV6-1*01 | 5'-CAGGAGGGCTCGGCA | AATGCTGGTGTCACTCAGACCCCA-3' | 239 |
| TRBV6-4*01 | 5'-CAGGAGGGCTCGGCA | ATTGCTGGGATCACCCAGGCAC-3' | 240 |
| TRBV6-4*02 | 5'-CAGGAGGGCTCGGCA | ACTGCTGGGATCACCCAGGCAC-3' | 241 |
| TRBV7-1*01 | 5'-CAGGAGGGCTCGGCA | GGTGCTGGAGTCTCCCAGTCCCTG-3' | 242 |
| TRBV7-2*01 | 5'-CAGGAGGGCTCGGCA | GGAGCTGGAGTCTCCCAGTCCCC-3' | 243 |

TABLE 6-continued single cell TCRβ cloning primers.
Vβ-gene-specific primers for cloning TCRα genes

| TRBV gene | Signal peptide sequence | TRBV gene-specific sequence | SEQ ID NO: |
|---|---|---|---|
| TRBV7-2*04 | 5'-CAGGAGGGCTCGGCA | GGAGCTGGAGTTTCCCAGTCCCC-3' | 244 |
| TRBV7-3*01 | 5'-CAGGAGGGCTCGGCA | GGTGCTGGAGTCTCCCAGACCC-3' | 245 |
| TRBV7-3*05 | 5'-CAGGAGGGCTCGGCA | TGGGAGCTCAGGTGTGATCCAATTTC-3' | 246 |
| TRBV7-4*01 | 5'-CAGGAGGGCTCGGCA | GGTGCTGGAGTCTCCCAGTCCC-3' | 247 |
| TRBV7-6*01 | 5'-CAGGAGGGCTCGGCA | GGTGCTGGAGTCTCCCAGTCTCCC-3' | 248 |
| TRBV7-9*01 | 5'-CAGGAGGGCTCGGCA | GATACTGGAGTCTCCCAGAACCCCAG-3' | 249 |
| TRBV7-9*03 | 5'-CAGGAGGGCTCGGCA | GATACTGGAGTCTCCCAGGACCCCAG-3' | 250 |
| TRBV7-9*04 | 5'-CAGGAGGGCTCGGCA | ATATCTGGAGTCTCCCACAACCCCAGAC-3' | 251 |
| TRBV7-9*07 | 5'-CAGGAGGGCTCGGCA | CACAACCGCCTTTATTGGTACCGACAG-3' | 252 |
| TRBV9*01 | 5'-CAGGAGGGCTCGGCA | GATTCTGGAGTCACACAAACCCCAAAGC-3' | 253 |
| TRBV10-1*01 | 5'-CAGGAGGGCTCGGCA | GATGCTGAAATCACCCAGAGCCCAAG-3' | 254 |
| TRBV10-2*01 | 5'-CAGGAGGGCTCGGCA | GATGCTGGAATCACCCAGAGCCCA-3' | 255 |
| TRBV10-2*02 | 5'-CAGGAGGGCTCGGCA | AAGGCAGGTGACCTTGATGTGTCACC-3' | 256 |
| TRBV11-1*01 | 5'-CAGGAGGGCTCGGCA | GAAGCTGAAGTTGCCCAGTCCCC-3' | 257 |
| TRBV11-2*01 | 5'-CAGGAGGGCTCGGCA | GAAGCTGGAGTTGCCCAGTCTCCCAG-3' | 258 |
| TRBV11-3*01 | 5'-CAGGAGGGCTCGGCA | GAAGCTGGAGTGGTTCAGTCTCCCAGA-3 | 259 |
| TRBV11-3*03 | 5'-CAGGAGGGCTCGGCA | GGTCTCCCAGATATAAGATTATAGAGAAGAAACAGC-3' | 260 |
| TRBV12-1*01 | 5'-CAGGAGGGCTCGGCA | GATGCTGGTGTTATCCAGTCACCCAGG-3' | 261 |
| TRBV12-2*01 | 5'-CAGGAGGGCTCGGCA | GATGCTGGCATTATCCAGTCACCCAAG-3' | 262 |
| TRBV12-3*01 | 5'-CAGGAGGGCTCGGCA | GATGCTGGAGTTATCCAGTCACCCC-3' | 263 |
| TRBV12-5*01 | 5'-CAGGAGGGCTCGGCA | GATGCTAGAGTCACCCAGACACCAAGG-3' | 264 |
| TRBV13*01 | 5'-CAGGAGGGCTCGGCA | GCTGCTGGAGTCATCCAGTCCCC-3' | 265 |
| TRBV14*01 | 5'-CAGGAGGGCTCGGCA | GAAGCTGGAGTTACTCAGTTCCCCAGC-3' | 266 |
| TRBV15*01 | 5'-CAGGAGGGCTCGGCA | GATGCCATGGTCATCCAGAACCCAAG-3' | 267 |
| TRBV16*01 | 5'-CAGGAGGGCTCGGCA | GGTGAAGAAGTCGCCCAGACTCCA-3' | 268 |
| TRBV17*01 | 5'-CAGGAGGGCTCGGCA | GAGCCTGGAGTCAGCCAGACCC-3' | 269 |
| TRBV18*01 | 5'-CAGGAGGGCTCGGCA | AATGCCGGCGTCATGCAGAAC-3' | 270 |
| TRBV19*01 | 5'-CAGGAGGGCTCGGCA | GATGGTGGAATCACTCAGTCCCCAAAG-3' | 271 |
| TRBV20-1*01 | 5'-CAGGAGGGCTCGGCA | GGTGCTGTCGTCTCTCAACATCCGAG-3' | 272 |
| TRBV20/OR9-2*01 | 5'-CAGGAGGGCTCGGCA | AGTGCTGTCGTCTCTCAACATCCGAG-3' | 273 |
| TRBV21-1*01 | 5'-CAGGAGGGCTCGGCA | GACACCAAGGTCACCCAGAGACCTAGAC-3' | 274 |
| TRBV21/OR9-2*01 | 5'-CAGGAGGGCTCGGCA | GACACCAAGGTCACCCAGAGACCTAGATTTC-3' | 275 |
| TRBV23-1*01 | 5'-CAGGAGGGCTCGGCA | CATGCCAAAGTCACACAGACTCCAGG-3' | 276 |
| TRBV24-1*01 | 5'-CAGGAGGGCTCGGCA | GATGCTGATGTTACCCAGACCCCAAG-3' | 277 |
| TRBV25-1*01 | 5'-CAGGAGGGCTCGGCA | GAAGCTGACATCTACCAGACCCCAAGATAC-3' | 278 |
| TRBV26*01 | 5'-CAGGAGGGCTCGGCA | GATGCTGTAGTTACACAATTCCCAAGACACAG-3' | 279 |
| TRBV26/OR9-2*01 | 5'-CAGGAGGGCTCGGCA | GATGCTGTAGTTACACAATTCTCAAGACACAGAATC-3' | 280 |

TABLE 6-continued single cell TCRβ cloning primers.
Vβ-gene-specific primers for cloning TCRα genes

| TRBV gene | Signal peptide sequence | TRBV gene-specific sequence | SEQ ID NO: |
|---|---|---|---|
| TRBV27*01 | 5'-CAGGAGGGCTCGGCA | GAAGCCCAAGTGACCCAGAACCC-3' | 281 |
| TRBV28*01 | 5'-CAGGAGGGCTCGGCA | GATGTGAAAGTAACCCAGAGCTCGAGATATC-3' | 282 |
| TRBV29-1*01 | 5'-CAGGAGGGCTCGGCA | AGTGCTGTCATCTCTCAAAAGCCAAGC-3' | 283 |
| TRBV29-1*03 | 5'-CAGGAGGGCTCGGCA | ACGATCCAGTGTCAAGTCGATAGCCAAG-3' | 284 |
| TRBV30*01 | 5'-CAGGAGGGCTCGGCA | TCTCAGACTATTCATCAATGGCCAGCG-3' | 285 |
| TRBV30*04 | 5'-CAGGAGGGCTCGGCA | ACTATTCATCAATGGCCAGCGACCC-3' | 286 |

To produce retrovirus, HEK-293T/17 cells were transfected via calcium phosphate precipitation with the TCR vector, a packaging vector encoding gag-pol, and a pseudotyping vector encoding RD114 envelope glycoprotein. Media was replaced 24 hours following transfection and viral supernatant was collected 48 hours following transfection. An equal volume of viral supernatant was added to Jurkat T cells in RPMI-based medium (final density: 0.5×106 cells/mL) and polybrene was added to a final concentration of 5 μg/mL. Cells were spinfected at 1350×g for 90 minutes at 30° C., and then incubated with virus overnight at 37° C., 5% CO2. Half of the media was replaced 24 hours following infection and cells were assayed for TCR specificity 48 hours following infection via flow cytometry using cognate fluorescent peptide-MHC tetramers.

Example 19. MHC I HLA Subtypes

TABLE 7

MHC I HLA Allelic Subtypes

| | | | |
|---|---|---|---|
| A*02:01 | C*04:01 | A*02:01 | A*11:01 |
| C*07:01 | C*07:01 | C*04:01 | A*24:02 |
| A*01:01 | C*06:02 | A*24:02 | C*07:02 |
| A*03:01 | A*02:01 | C*07:02 | C*01:02 |
| C*07:02 | A*23:01 | C*07:01 | A*33:03 |
| C*04:01 | C*02:02 | C*03:04 | C*08:01 |
| B*44:02 | A*03:01 | A*03:01 | C*03:04 |

TABLE 7-continued

MHC I HLA Allelic Subtypes

| | | | |
|---|---|---|---|
| B*07:02 | C*07:02 | B*07:02 | A*02:01 |
| B*08:01 | B*53:01 | B*35:01 | B*40:01 |
| C*05:01 | B*07:02 | C*06:02 | C*04:01 |
| C*03:04 | C*16:01 | C*05:01 | B*58:01 |
| C*06:02 | B*15:03 | A*01:01 | B*46:01 |
| A*11:01 | B*58:01 | A*11:01 | B*51:01 |
| B*40:01 | A*68:02 | B*51:01 | C*03:02 |
| A*24:02 | C*17:01 | C*16:01 | B*38:02 |
| B*35:01 | B*45:01 | B*44:03 | A*02:07 |
| C*03:03 | B*42:01 | C*01:02 | B*15:01 |
| B*51:01 | A*30:01 | A*29:02 | A*02:06 |
| C*12:03 | B*35:01 | C*08:02 | C*03:03 |
| B*15:01 | A*01:01 | B*18:01 | B*15:02 |
| A*29:02 | C*03:04 | A*31:01 | A*02:03 |
| A*26:01 | A*30:02 | B*52:01 | B*44:03 |
| A*32:01 | B*08:01 | B*14:02 | C*14:02 |
| C*08:02 | A*34:02 | C*02:02 | B*35:01 |
| A*25:01 | A*74:01 | C*12:03 | C*06:02 |
| B*57:01 | A*33:03 | A*26:01 | B*54:01 |
| B*14:02 | C*18:01 | A*68:01 | B*13:01 |
| C*02:02 | A*29:02 | B*08:01 | B*40:02 |
| B*18:01 | B*44:03 | A*30:02 | B*55:02 |
| B*44:03 | B*49:01 | B*44:02 | A*26:01 |

While the present invention has been illustrated and described with reference to certain exemplary embodiments, those of ordinary skill in the art will understand that various modifications and changes may be made to the described embodiments without departing from the spirit and scope of the present invention, as defined in the following claims.

What is claimed is:

1. An antigen complex, comprising:
a nanoparticle sorting agent comprising:
  a nanoparticle;
  a polynucleotide detection tag having at least one coding region, the polynucleotide detection tag being conjugated to the nanoparticle; and
  a first polynucleotide hybridization domain conjugated to the polynucleotide detection tag; and
a peptide-loaded streptavidin major histocompatability complex (MHC) tetramer, comprising:
  a modified streptavidin protein;
  four biotin-modified MHC proteins each independently conjugated to the modified streptavidin protein;
  an antigen peptide bound to the biotin-modified MHC proteins; and
  a second polynucleotide hybridization domain different from the first polynucleotide hybridization domain and conjugated to the modified streptavidin protein,
the nanoparticle sorting agent being linked to the peptide-loaded streptavidin MHC tetramer by hybridization of the first polynucleotide hybridization domain to the second polynucleotide hybridization domain.

2. The antigen complex of claim 1, wherein the modified streptavidin protein is modified with a binding moiety selected from the group consisting of a cysteine, a thiol group, maleimide group, an adamantane group, a cyclodextrin group, an amine group, a carboxy group, an azide group, and an alkyne group.

3. The antigen complex of claim 1, wherein the modified streptavidin protein is modified with cysteine.

4. The antigen complex of claim 1, wherein the second polynucleotide hybridization domain is modified with a binding moiety selected from the group consisting of a cysteine, a thiol group, maleimide group, an adamantane group, a cyclodextrin group, an amine group, a carboxy group, an azide group, and an alkyne group.

5. The antigen complex of claim 1, wherein the second polynucleotide hybridization domain is modified with maleimide.

6. The antigen complex of claim 1, wherein the nanoparticle is a magnetic nanoparticle or a polystyrene nanoparticle.

7. The antigen complex of claim 1, wherein the at least one coding region of the polynucleotide detection tag comprises at least three different coding regions.

8. The antigen complex of claim 1, wherein the nanoparticle is modified with a binding moiety selected from the group consisting of streptavidin, biotin, a cysteine, a thiol group, maleimide group, an adamantane group, a cyclodextrin group, an amine group, a carboxy group, an azide group, and an alkyne group.

9. The antigen complex of claim 1, wherein the nanoparticle is modified with streptavidin and the polynucleotide detection tag is modified with biotin.

10. The antigen complex of claim 1, wherein the antigen peptide is selected from the group consisting of tumor antigens, tumor neoantigens, viral antigens, phosphoantigens, and combinations thereof.

11. A library of antigen complexes, comprising:
a plurality of antigen complexes of claim 1, each of the antigen complexes having a different antigen peptide and different polynucleotide detection tag than any other of the antigen complexes in the plurality of antigen complexes.

12. A kit for detecting neoantigen-specific T cells, comprising:
an antigen complex, comprising:
a nanoparticle sorting agent comprising:
  a nanoparticle;
  a polynucleotide detection tag having at least one coding region, the polynucleotide detection tag being conjugated to the nanoparticle; and
  a first polynucleotide hybridization domain conjugated to the polynucleotide detection tag; and
a peptide-loaded streptavidin major histocompatability complex (MHC) tetramer, comprising:
  a modified streptavidin protein;
  four biotin-modified MHC proteins each independently conjugated to the modified streptavidin protein;
  an antigen peptide bound to the biotin-modified MHC proteins; and
  a second polynucleotide hybridization domain different from the first polynucleotide hybridization domain and conjugated to the modified streptavidin protein,
the nanoparticle sorting agent being linked to the peptide-loaded streptavidin MEW tetramer by hybridization of the first polynucleotide hybridization domain to the second polynucleotide hybridization domain; and
a decoding polynucleotide that is capable of hybridizing to the at least one coding region of the polynucleotide detection tag.

13. The kit of claim 12, wherein the decoding polynucleotide is a labeled decoding polynucleotide, the kit further comprising:
a displacement polynucleotide capable of hybridizing to the decoding polynucleotide.

14. The kit of claim 13, wherein the labeled decoding polynucleotide comprises a nucleotide sequence conjugated to a distinguishable fluorescent dye.

15. A method for isolating neo-antigen-specific T cells for a tumor in a subject, comprising:
identifying candidate T cell epitopes for the tumor using a major histocompatiblity complex (MHC) binding algorithm;
synthesizing antigen peptides corresponding to the candidate T cell epitopes;
preparing a library of antigen complexes using the antigen peptides, the antigen complexes each comprising:
a nanoparticle sorting agent comprising:
  a nanoparticle;
  a polynucleotide detection tag having at least one coding region, the polynucleotide detection tag being conjugated to the nanoparticle; and a first polynucleotide hybridization domain conjugated to the polynucleotide detection tag; and a peptide-loaded streptavidin major histocompatability complex (MHC) tetramer, comprising:
  a modified streptavidin protein;
  four biotin-modified MHC proteins each independently conjugated to the modified streptavidin protein;
  the antigen peptide bound to the biotin-modified MHC proteins; and
  a second polynucleotide hybridization domain different from the first polynucleotide hybridization domain and conjugated to the modified streptavidin protein, the nanoparticle sorting agent being linked to the peptide-loaded streptavidin MHC tetramer by hybridization of the first polynucleotide hybridization domain to the second polynucleotide hybridization domain;

each of the antigen complexes having a different antigen peptide and different polynucleotide detection tag than any other of the antigen complexes in the plurality of antigen complexes;

incubating the library of antigen complexes with TILs or PBMCs from the subject; and separating paired T cells from unpaired T cells, the paired T cells comprising those T cells that have paired with any of the antigen peptides of any of the antigen complexes in the library of antigen complexes.

16. The method of claim 15, wherein identifying candidate T cell epitopes comprises acquiring the genome or exome sequence of the tumor.

17. The method of claim 15, further comprising:
  adding the paired T cells to a microfluidic device to separate the paired T cells into individual paired T cells; and
  detecting the sequence of the at least one coding region of the polynucleotide detection tag of the antigen complex of each individual paired T cell.

18. The method of claim 17, wherein the detecting the sequence of the at least one coding region of the polynucleotide detection tag of the antigen complex of each individual paired T cell comprises:
  Incubating the polynucleotide detection tag of each individual paired T cell with at least two labeled decoding polynucleotides; and
  detecting presence of a hybridized labeled decoding polynucleotide to thereby determine the sequence of the at least one coding region of the polynucleotide detection tag.

19. The method of claim 17, wherein the least one coding region of the polynucleotide detection tag of the antigen complex comprises at least two coding regions, and the detecting the sequence of the at least two coding regions of the polynucleotide detection tag of the antigen complex of each individual paired T cell comprises:
  incubating the polynucleotide detection tag of each individual paired T cell with at least two first labeled decoding polynucleotides;
  detecting presence of one or more first hybridized labeled decoding polynucleotides to thereby determine the sequence of a first one of the at least two coding regions of the polynucleotide detection tag;
  incubating the one or more first hybridized labeled decoding polynucleotides with one or more displacement polynucleotides to remove the first labeled decoding polynucleotides from the first hybridized labeled decoding polynucleotide to yield a partially decoded polynucleotide detection tag;
  incubating the partially decoded polynucleotide detection tag with one or more second labeled decoding polynucleotides; and
  detecting presence of a second hybridized labeled decoding polynucleotide to thereby determine the sequence of a second one of the at least two coding regions of the polynucleotide detection tag of the antigen complex of each individual paired T cell.

* * * * *